US009445730B2

(12) United States Patent
Snyder et al.

(10) Patent No.: US 9,445,730 B2
(45) Date of Patent: *Sep. 20, 2016

(54) IMPLANTABLE SYSTEMS AND METHODS FOR IDENTIFYING A CONTRA-ICTAL CONDITION IN A SUBJECT

(71) Applicant: CYBERONICS, INC., Houston, TX (US)

(72) Inventors: David Snyder, Bainbridge Island, WA (US); Kent W. Leyde, Sammamish, WA (US); John F. Harris, Medina, WA (US)

(73) Assignee: CYBERONICS, INC., Houston, TX (US)

( * ) Notice: Subject to any disclaimer, the term of this patent is extended or adjusted under 35 U.S.C. 154(b) by 237 days.

This patent is subject to a terminal disclaimer.

(21) Appl. No.: 14/021,651

(22) Filed: Sep. 9, 2013

(65) Prior Publication Data

US 2014/0012111 A1 Jan. 9, 2014

Related U.S. Application Data

(63) Continuation of application No. 13/225,241, filed on Sep. 2, 2011, now Pat. No. 8,543,199, which is a continuation of application No. 12/053,312, filed on Mar. 21, 2008, now Pat. No. 8,036,736.

(60) Provisional application No. 60/919,364, filed on Mar. 21, 2007.

(51) Int. Cl.
*A61B 5/04* (2006.01)
*A61B 5/0205* (2006.01)
(Continued)

(52) U.S. Cl.
CPC ......... *A61B 5/02055* (2013.01); *A61B 5/0006* (2013.01); *A61B 5/0031* (2013.01);
(Continued)

(58) Field of Classification Search
CPC .................................... A61B 5/0476–5/14847
See application file for complete search history.

(56) References Cited

U.S. PATENT DOCUMENTS

| | | |
|---|---|---|
| 3,218,638 A | 11/1965 | Honig |
| 3,498,287 A | 3/1970 | Ertl |

(Continued)

FOREIGN PATENT DOCUMENTS

| | | |
|---|---|---|
| CA | 2251852 | 4/1999 |
| CA | 2423840 | 2/2002 |

(Continued)

OTHER PUBLICATIONS

Adjouadi, et al. A new mathematical approach based on orthogonal operators for the detection of interictal spikes in epileptogenic data. Biomed. Sci. Instrum. 2004; 40: 175-80.

(Continued)

*Primary Examiner* — Christian Jang
(74) *Attorney, Agent, or Firm* — Foley & Lardner LLP

(57) ABSTRACT

Systems and methods of monitoring a subject's neurological condition are provided. In some embodiments, the method includes the steps of analyzing a physiological signal (such as an EEG) from a subject to determine if the subject is in a contra-ictal condition; and if the subject is in a contra-ictal condition, providing an indication (e.g., to the subject and/or to a caregiver) that the subject is in the contra-ictal condition. The systems and methods may utilize a minimally invasive, leadless device to monitor the subject's condition. In some embodiments, if the subject is in a pro-ictal condition, the method includes the step of providing an indication (such as a red light) that the subject is in the pro-ictal condition.

23 Claims, 23 Drawing Sheets

(51) Int. Cl.
  *A61B 5/00*    (2006.01)
  *A61B 5/01*    (2006.01)
  *A61B 5/021*   (2006.01)
  *A61B 5/026*   (2006.01)
  *A61B 5/0452*  (2006.01)
  *A61B 5/048*   (2006.01)
  *A61B 5/08*    (2006.01)
  *A61B 5/145*   (2006.01)
  *A61B 5/1455*  (2006.01)

(52) U.S. Cl.
  CPC .............. *A61B 5/01* (2013.01); *A61B 5/021* (2013.01); *A61B 5/0205* (2013.01); *A61B 5/026* (2013.01); *A61B 5/048* (2013.01); *A61B 5/0452* (2013.01); *A61B 5/08* (2013.01); *A61B 5/145* (2013.01); *A61B 5/14552* (2013.01); *A61B 5/4094* (2013.01); *A61B 5/7232* (2013.01); *A61B 2560/0219* (2013.01)

(56) References Cited

U.S. PATENT DOCUMENTS

| | | |
|---|---|---|
| 3,522,811 A | 8/1970 | Schwartz |
| 3,575,162 A | 4/1971 | Gaarder |
| 3,837,331 A | 9/1974 | Ross |
| 3,850,161 A | 11/1974 | Liss |
| 3,863,625 A | 2/1975 | Viglione et al. |
| 3,882,850 A | 5/1975 | Bailin et al. |
| 3,918,461 A | 11/1975 | Cooper |
| 3,967,616 A | 7/1976 | Ross |
| 3,993,046 A | 11/1976 | Fernandez |
| 4,201,224 A | 5/1980 | John |
| 4,214,591 A | 7/1980 | Sato et al. |
| 4,279,258 A | 7/1981 | John |
| 4,305,402 A | 12/1981 | Katims |
| 4,334,545 A | 6/1982 | Shiga |
| 4,407,299 A | 10/1983 | Culver |
| 4,408,616 A | 10/1983 | Duffy et al. |
| 4,421,122 A | 12/1983 | Duffy |
| 4,471,786 A | 9/1984 | Inagaki |
| 4,494,950 A | 1/1985 | Fischell |
| 4,505,275 A | 3/1985 | Chen |
| 4,545,388 A | 10/1985 | John |
| 4,556,061 A | 12/1985 | Barreras et al. |
| 4,566,464 A | 1/1986 | Piccone et al. |
| 4,573,481 A | 3/1986 | Bullara |
| 4,579,125 A | 4/1986 | Strobl et al. |
| 4,590,946 A | 5/1986 | Loeb |
| 4,612,934 A | 9/1986 | Borkan |
| 4,679,144 A | 7/1987 | Cox et al. |
| 4,686,999 A | 8/1987 | Snyder et al. |
| 4,702,254 A | 10/1987 | Zabara |
| 4,735,208 A | 4/1988 | Wyler et al. |
| 4,768,176 A | 8/1988 | Kehr et al. |
| 4,768,177 A | 8/1988 | Kehr et al. |
| 4,785,827 A | 11/1988 | Fischer |
| 4,793,353 A | 12/1988 | Borkan |
| 4,817,628 A | 4/1989 | Zealear |
| 4,838,272 A | 6/1989 | Lieber |
| 4,844,075 A | 7/1989 | Liss et al. |
| 4,852,573 A | 8/1989 | Kennedy |
| 4,873,981 A | 10/1989 | Abrams et al. |
| 4,878,498 A | 11/1989 | Abrams et al. |
| 4,903,702 A | 2/1990 | Putz |
| 4,920,979 A | 5/1990 | Bullara |
| 4,926,865 A | 5/1990 | Oman |
| 4,934,372 A | 6/1990 | Corenman et al. |
| 4,955,380 A | 9/1990 | Edell |
| 4,978,680 A | 12/1990 | Sofia |
| 4,979,511 A | 12/1990 | Terry |
| 4,991,582 A | 2/1991 | Byers et al. |
| 5,010,891 A | 4/1991 | Chamoun |
| 5,016,635 A | 5/1991 | Graupe |
| 5,025,807 A | 6/1991 | Zabara |
| 5,031,618 A | 7/1991 | Mullett |
| 5,070,873 A | 12/1991 | Graupe et al. |
| 5,082,861 A | 1/1992 | Sofia |
| 5,097,835 A | 3/1992 | Putz |
| RE34,015 E | 8/1992 | Duffy |
| 5,154,172 A | 10/1992 | Terry |
| 5,167,229 A | 12/1992 | Peckham et al. |
| 5,179,950 A | 1/1993 | Stanislaw |
| 5,181,520 A | 1/1993 | Wertheim et al. |
| 5,186,170 A | 2/1993 | Varichio |
| 5,188,104 A | 2/1993 | Wernicke |
| 5,190,029 A | 3/1993 | Byron et al. |
| 5,193,539 A | 3/1993 | Schulman et al. |
| 5,193,540 A | 3/1993 | Schulman et al. |
| 5,205,285 A | 4/1993 | Baker, Jr. |
| 5,215,086 A | 6/1993 | Terry, Jr. et al. |
| 5,215,088 A | 6/1993 | Normann |
| 5,215,089 A | 6/1993 | Baker, Jr. |
| 5,222,494 A | 6/1993 | Baker, Jr. |
| 5,222,503 A | 6/1993 | Ives |
| 5,231,988 A | 8/1993 | Wernicke et al. |
| 5,235,980 A | 8/1993 | Varichio et al. |
| 5,237,991 A | 8/1993 | Baker, Jr. |
| 5,251,634 A | 10/1993 | Weinberg |
| 5,263,480 A | 11/1993 | Wernicke et al. |
| 5,265,619 A | 11/1993 | Comby et al. |
| 5,269,302 A | 12/1993 | Swartz et al. |
| 5,269,303 A | 12/1993 | Wernicke et al. |
| 5,269,315 A | 12/1993 | Leuchter et al. |
| 5,292,772 A | 3/1994 | Sofia |
| 5,293,879 A | 3/1994 | Vonk |
| 5,299,118 A | 3/1994 | Martens et al. |
| 5,299,569 A | 4/1994 | Wernicke et al. |
| 5,300,094 A | 4/1994 | Kallok et al. |
| 5,304,206 A | 4/1994 | Baker, Jr. et al. |
| 5,311,876 A | 5/1994 | Olsen et al. |
| 5,312,439 A | 5/1994 | Loeb |
| 5,314,458 A | 5/1994 | Najafi et al. |
| 5,324,316 A | 6/1994 | Schulman et al. |
| 5,330,515 A | 7/1994 | Rutecki et al. |
| 5,335,657 A | 8/1994 | Terry et al. |
| 5,342,408 A | 8/1994 | deCoriolis et al. |
| 5,342,409 A | 8/1994 | Mullett |
| 5,343,064 A | 8/1994 | Spangler et al. |
| 5,349,962 A | 9/1994 | Lockard et al. |
| 5,351,394 A | 10/1994 | Weinberg |
| 5,361,760 A | 11/1994 | Normann |
| 5,365,939 A | 11/1994 | Ochs |
| 5,376,359 A | 12/1994 | Johnson |
| 5,392,788 A | 2/1995 | Hudspeth |
| 5,405,365 A | 4/1995 | Hoegnelid et al. |
| 5,405,367 A | 4/1995 | Schulman et al. |
| 5,411,540 A | 5/1995 | Edell et al. |
| 5,458,117 A | 10/1995 | Chamoun |
| 5,474,547 A | 12/1995 | Aebischer et al. |
| 5,476,494 A | 12/1995 | Edell et al. |
| 5,486,999 A | 1/1996 | Mebane |
| 5,513,649 A | 5/1996 | Gevins |
| 5,517,115 A | 5/1996 | Prammer |
| 5,531,778 A | 7/1996 | Maschino et al. |
| 5,540,730 A | 7/1996 | Terry |
| 5,540,734 A | 7/1996 | Zabara |
| 5,549,656 A | 8/1996 | Reiss |
| 5,555,191 A | 9/1996 | Hripcsak |
| 5,571,148 A | 11/1996 | Loeb et al. |
| 5,571,150 A | 11/1996 | Wernicke |
| 5,575,813 A | 11/1996 | Edell et al. |
| 5,578,036 A | 11/1996 | Stone et al. |
| 5,611,350 A | 3/1997 | John |
| 5,626,145 A | 5/1997 | Clapp et al. |
| 5,626,627 A | 5/1997 | Krystal et al. |
| 5,638,826 A | 6/1997 | Wolpaw |
| 5,649,068 A | 7/1997 | Boser et al. |
| 5,672,154 A | 9/1997 | Sillen et al. |
| 5,683,422 A | 11/1997 | Rise |
| 5,683,432 A | 11/1997 | Goedeke et al. |
| 5,690,681 A | 11/1997 | Geddes et al. |
| 5,690,691 A | 11/1997 | Chen et al. |
| 5,697,369 A | 12/1997 | Long |

(56) References Cited

U.S. PATENT DOCUMENTS

| | | |
|---|---|---|
| 5,700,282 A | 12/1997 | Zabara |
| 5,704,352 A | 1/1998 | Tremblay et al. |
| 5,707,400 A | 1/1998 | Terry et al. |
| 5,711,316 A | 1/1998 | Elsberry et al. |
| 5,713,923 A | 2/1998 | Ward et al. |
| 5,715,821 A | 2/1998 | Faupel |
| 5,716,377 A | 2/1998 | Rise et al. |
| 5,720,294 A | 2/1998 | Skinner |
| 5,735,814 A | 4/1998 | Elsberry et al. |
| 5,743,860 A | 4/1998 | Hively et al. |
| 5,752,979 A | 5/1998 | Benabid |
| 5,769,778 A | 6/1998 | Abrams et al. |
| 5,776,434 A | 7/1998 | Purewal et al. |
| 5,782,798 A | 7/1998 | Rise |
| 5,782,874 A | 7/1998 | Loos |
| 5,782,891 A | 7/1998 | Hassler et al. |
| 5,792,186 A | 8/1998 | Rise |
| 5,800,474 A | 9/1998 | Bernabid et al. |
| 5,813,993 A | 9/1998 | Kaplan |
| 5,814,014 A | 9/1998 | Elsberry et al. |
| 5,815,413 A | 9/1998 | Hively et al. |
| 5,816,247 A | 10/1998 | Maynard |
| 5,824,021 A | 10/1998 | Rise |
| 5,832,932 A | 11/1998 | Elsberry et al. |
| 5,833,709 A | 11/1998 | Rise et al. |
| 5,857,978 A | 1/1999 | Hively et al. |
| 5,862,803 A * | 1/1999 | Besson et al. ............... 600/508 |
| 5,876,424 A | 3/1999 | O'Phelan et al. |
| 5,899,922 A | 5/1999 | Loos |
| 5,913,881 A | 6/1999 | Benz et al. |
| 5,916,239 A | 6/1999 | Geddes et al. |
| 5,917,429 A | 6/1999 | Otis, Jr. et al. |
| 5,928,272 A | 7/1999 | Adkins |
| 5,931,791 A | 8/1999 | Saltzstein et al. |
| 5,938,689 A | 8/1999 | Fischell et al. |
| 5,941,906 A | 8/1999 | Barreras et al. |
| 5,950,632 A | 9/1999 | Reber et al. |
| 5,957,861 A | 9/1999 | Combs et al. |
| 5,971,594 A | 10/1999 | Sahai et al. |
| 5,975,085 A | 11/1999 | Rise |
| 5,978,702 A | 11/1999 | Ward et al. |
| 5,978,710 A | 11/1999 | Prutchi et al. |
| 5,995,868 A | 11/1999 | Dorfmeister et al. |
| 6,006,124 A | 12/1999 | Fischell et al. |
| 6,016,449 A | 1/2000 | Fischell et al. |
| 6,018,682 A | 1/2000 | Rise |
| 6,042,548 A | 3/2000 | Giuffre |
| 6,042,579 A | 3/2000 | Elsberry et al. |
| 6,051,017 A | 4/2000 | Loeb et al. |
| 6,052,619 A | 4/2000 | John |
| 6,061,593 A | 5/2000 | Fischell et al. |
| 6,066,163 A | 5/2000 | John |
| 6,081,744 A | 6/2000 | Loos |
| 6,094,598 A | 7/2000 | Elsberry et al. |
| 6,109,269 A | 8/2000 | Rise et al. |
| 6,117,066 A | 9/2000 | Abrams et al. |
| 6,128,537 A | 10/2000 | Rise et al. |
| 6,128,538 A | 10/2000 | Fischell et al. |
| 6,134,474 A | 10/2000 | Fischell et al. |
| 6,161,045 A | 12/2000 | Fischell et al. |
| 6,167,304 A | 12/2000 | Loos |
| 6,171,239 B1 | 1/2001 | Humphrey |
| 6,176,242 B1 | 1/2001 | Rise |
| 6,205,359 B1 | 3/2001 | Boveja |
| 6,208,893 B1 | 3/2001 | Hofmann |
| 6,221,011 B1 | 4/2001 | Bardy |
| 6,227,203 B1 | 5/2001 | Rise et al. |
| 6,230,049 B1 | 5/2001 | Fischell et al. |
| 6,248,126 B1 | 6/2001 | Lesser et al. |
| 6,249,703 B1 | 6/2001 | Stanton |
| 6,263,237 B1 | 7/2001 | Rise |
| 6,280,198 B1 | 8/2001 | Calhoun et al. |
| 6,304,775 B1 | 10/2001 | Iasemidis et al. |
| 6,309,406 B1 | 10/2001 | Jones et al. |
| 6,328,699 B1 | 12/2001 | Eigler |
| 6,337,997 B1 | 1/2002 | Rise |
| 6,339,725 B1 | 1/2002 | Naritoku |
| 6,341,236 B1 | 1/2002 | Osorio et al. |
| 6,343,226 B1 | 1/2002 | Sunde et al. |
| 6,353,754 B1 | 3/2002 | Fischell et al. |
| 6,354,299 B1 | 3/2002 | Fischell et al. |
| 6,356,784 B1 | 3/2002 | Lozano et al. |
| 6,356,788 B2 | 3/2002 | Boveja |
| 6,358,203 B2 | 3/2002 | Bardy |
| 6,358,281 B1 | 3/2002 | Berrang et al. |
| 6,360,122 B1 | 3/2002 | Fischell |
| 6,366,813 B1 | 4/2002 | DiLorenzo |
| 6,366,814 B1 | 4/2002 | Boveja |
| 6,374,140 B1 | 4/2002 | Rise |
| 6,386,882 B1 | 5/2002 | Linberg |
| 6,402,678 B1 | 6/2002 | Fischell et al. |
| 6,411,854 B1 | 6/2002 | Tziviskos et al. |
| 6,427,086 B1 | 7/2002 | Fischell et al. |
| 6,434,419 B1 | 8/2002 | Gevins et al. |
| 6,442,421 B1 | 8/2002 | Quyen et al. |
| 6,443,891 B1 | 9/2002 | Grevious |
| 6,453,198 B1 | 9/2002 | Torgerson |
| 6,463,328 B1 | 10/2002 | John |
| 6,466,822 B1 | 10/2002 | Pless |
| 6,471,645 B1 | 10/2002 | Warkentin et al. |
| 6,473,639 B1 | 10/2002 | Fischell et al. |
| 6,473,644 B1 | 10/2002 | Terry et al. |
| 6,480,743 B1 | 11/2002 | Kirkpatrick |
| 6,484,132 B1 | 11/2002 | Hively et al. |
| 6,488,617 B1 | 12/2002 | Katz |
| 6,496,724 B1 | 12/2002 | Levendowski et al. |
| 6,505,077 B1 | 1/2003 | Kast et al. |
| 6,510,340 B1 | 1/2003 | Jordan |
| 6,511,424 B1 | 1/2003 | Moore-Ede |
| 6,529,774 B1 | 3/2003 | Greene |
| 6,534,693 B2 | 3/2003 | Fischell et al. |
| 6,547,746 B1 | 4/2003 | Marino |
| 6,549,804 B1 * | 4/2003 | Osorio et al. ............... 600/544 |
| 6,553,262 B1 | 4/2003 | Lang et al. |
| 6,560,486 B1 | 5/2003 | Osorio et al. |
| 6,571,123 B2 | 5/2003 | Ives et al. |
| 6,571,125 B2 | 5/2003 | Thompson |
| 6,572,528 B2 | 6/2003 | Rohan et al. |
| 6,587,719 B1 | 7/2003 | Barrett et al. |
| 6,591,132 B2 | 7/2003 | Gotman et al. |
| 6,591,137 B1 | 7/2003 | Fischell et al. |
| 6,591,138 B1 | 7/2003 | Fischell et al. |
| 6,600,956 B2 | 7/2003 | Maschino |
| 6,609,025 B2 | 8/2003 | Barrett et al. |
| 6,618,623 B1 | 9/2003 | Pless et al. |
| 6,620,415 B2 | 9/2003 | Donovan |
| 6,622,036 B1 | 9/2003 | Suffin |
| 6,622,038 B2 | 9/2003 | Barrett et al. |
| 6,622,041 B2 | 9/2003 | Terry et al. |
| 6,622,047 B2 | 9/2003 | Barrett et al. |
| 6,658,287 B1 | 12/2003 | Litt et al. |
| 6,665,562 B2 | 12/2003 | Gluckman et al. |
| 6,668,191 B1 | 12/2003 | Boveja |
| 6,671,555 B2 | 12/2003 | Gielen |
| 6,678,548 B1 | 1/2004 | Echauz et al. |
| 6,684,105 B2 | 1/2004 | Cohen et al. |
| 6,687,538 B1 | 2/2004 | Hrdlicka et al. |
| 6,735,467 B2 | 5/2004 | Wilson |
| 6,760,626 B1 | 7/2004 | Boveja |
| 6,768,969 B1 | 7/2004 | Nikitin et al. |
| 6,778,854 B2 | 8/2004 | Puskas |
| 6,782,292 B2 | 8/2004 | Whitehurst |
| 6,819,956 B2 | 11/2004 | DiLorenzo |
| 6,879,859 B1 | 4/2005 | Boveja |
| 6,893,395 B1 | 5/2005 | Kraus et al. |
| 6,901,294 B1 | 5/2005 | Whitehurst et al. |
| 6,901,296 B1 | 5/2005 | Whitehurst et al. |
| 6,912,419 B2 | 6/2005 | Hill |
| 6,921,538 B2 | 7/2005 | Donovan |
| 6,921,541 B2 | 7/2005 | Chasin et al. |
| 6,923,784 B2 | 8/2005 | Stein |
| 6,931,274 B2 | 8/2005 | Williams |
| 6,934,580 B1 | 8/2005 | Osorio |
| 6,937,891 B2 | 8/2005 | Leinders et al. |

(56) References Cited

U.S. PATENT DOCUMENTS

| | | |
|---|---|---|
| 6,944,501 B1 | 9/2005 | Pless |
| 6,950,706 B2 | 9/2005 | Rodriguez |
| 6,973,342 B1 | 12/2005 | Swanson |
| 6,990,372 B2 | 1/2006 | Perron et al. |
| 7,010,351 B2 | 3/2006 | Firlik et al. |
| 7,089,059 B1 | 8/2006 | Pless |
| 7,117,108 B2 | 10/2006 | Rapp et al. |
| 7,174,212 B1 | 2/2007 | Klehn et al. |
| 7,177,701 B1 | 2/2007 | Pianca |
| 7,209,787 B2 | 4/2007 | DiLorenzo |
| 7,212,851 B2 | 5/2007 | Donoghue et al. |
| 7,231,254 B2 | 6/2007 | DiLorenzo |
| 7,242,984 B2 | 7/2007 | DiLorenzo |
| 7,277,758 B2 | 10/2007 | DiLorenzo |
| 7,324,851 B1 | 1/2008 | DiLorenzo |
| 7,373,198 B2 | 5/2008 | Bibian et al. |
| 7,403,820 B2 | 7/2008 | DiLorenzo |
| 7,463,917 B2 | 12/2008 | Martinez |
| 7,623,928 B2 | 11/2009 | Dilorenzo |
| 7,631,015 B2 | 12/2009 | Gupta et al. |
| 7,747,325 B2 | 6/2010 | DiLorenzo |
| 7,805,196 B2 | 9/2010 | Miesel et al. |
| 7,853,329 B2 | 12/2010 | DiLorenzo |
| 7,881,798 B2 | 2/2011 | Miesel et al. |
| 8,036,736 B2 | 10/2011 | Snyder et al. |
| 8,055,348 B2 | 11/2011 | Heruth et al. |
| 2001/0051819 A1 | 12/2001 | Fischell et al. |
| 2001/0056290 A1 | 12/2001 | Fischell et al. |
| 2002/0002390 A1 | 1/2002 | Fischell et al. |
| 2002/0035338 A1 | 3/2002 | Dear et al. |
| 2002/0054694 A1 | 5/2002 | Vachtsevanos et al. |
| 2002/0072770 A1 | 6/2002 | Pless |
| 2002/0072776 A1 | 6/2002 | Osorio et al. |
| 2002/0072782 A1 | 6/2002 | Osorio et al. |
| 2002/0077670 A1 | 6/2002 | Archer et al. |
| 2002/0095099 A1 | 7/2002 | Quyen et al. |
| 2002/0099412 A1 | 7/2002 | Fischell et al. |
| 2002/0103512 A1 | 8/2002 | Echauz et al. |
| 2002/0109621 A1 | 8/2002 | Khair et al. |
| 2002/0111542 A1 | 8/2002 | Warkentin et al. |
| 2002/0116042 A1 | 8/2002 | Boling |
| 2002/0126036 A1 | 9/2002 | Flaherty et al. |
| 2002/0147388 A1 | 10/2002 | Mass et al. |
| 2002/0169485 A1 | 11/2002 | Pless et al. |
| 2003/0004428 A1 | 1/2003 | Pless |
| 2003/0009207 A1 | 1/2003 | Paspa et al. |
| 2003/0013981 A1 | 1/2003 | Gevins et al. |
| 2003/0018367 A1 | 1/2003 | DiLorenzo |
| 2003/0028072 A1 | 2/2003 | Fischell et al. |
| 2003/0050549 A1 | 3/2003 | Sochor |
| 2003/0050730 A1 | 3/2003 | Greeven et al. |
| 2003/0073917 A1 | 4/2003 | Echauz et al. |
| 2003/0074033 A1 | 4/2003 | Pless et al. |
| 2003/0083716 A1 | 5/2003 | Nicolelis et al. |
| 2003/0114886 A1 | 6/2003 | Gluckman et al. |
| 2003/0144709 A1 | 7/2003 | Zabara et al. |
| 2003/0144711 A1 | 7/2003 | Pless et al. |
| 2003/0144829 A1 | 7/2003 | Geatz et al. |
| 2003/0149457 A1 | 8/2003 | Tcheng et al. |
| 2003/0158587 A1 | 8/2003 | Esteller et al. |
| 2003/0167078 A1 | 9/2003 | Weisner et al. |
| 2003/0174554 A1 | 9/2003 | Dunstone et al. |
| 2003/0176806 A1 | 9/2003 | Pineda et al. |
| 2003/0187621 A1 | 10/2003 | Nikitin et al. |
| 2003/0195574 A1 | 10/2003 | Osorio et al. |
| 2003/0195588 A1 | 10/2003 | Fischell et al. |
| 2003/0195602 A1 | 10/2003 | Boling |
| 2004/0034368 A1 | 2/2004 | Pless et al. |
| 2004/0039427 A1 | 2/2004 | Barrett et al. |
| 2004/0039981 A1 | 2/2004 | Riedl et al. |
| 2004/0054297 A1 | 3/2004 | Wingeier et al. |
| 2004/0059761 A1 | 3/2004 | Hively |
| 2004/0068199 A1* | 4/2004 | Echauz ............ A61B 5/0476 600/544 |
| 2004/0073273 A1 | 4/2004 | Gluckman et al. |
| 2004/0077995 A1 | 4/2004 | Ferek-Petric |
| 2004/0078160 A1 | 4/2004 | Frei et al. |
| 2004/0082984 A1 | 4/2004 | Osorio et al. |
| 2004/0087835 A1 | 5/2004 | Hively |
| 2004/0097802 A1 | 5/2004 | Cohen |
| 2004/0122281 A1 | 6/2004 | Fischell et al. |
| 2004/0122335 A1 | 6/2004 | Sackellares et al. |
| 2004/0127810 A1 | 7/2004 | Sackellares et al. |
| 2004/0133119 A1 | 7/2004 | Osorio et al. |
| 2004/0133248 A1 | 7/2004 | Frei et al. |
| 2004/0133390 A1 | 7/2004 | Osorio et al. |
| 2004/0138516 A1 | 7/2004 | Osorio et al. |
| 2004/0138517 A1 | 7/2004 | Osorio et al. |
| 2004/0138536 A1 | 7/2004 | Frei et al. |
| 2004/0138578 A1 | 7/2004 | Pineda et al. |
| 2004/0138579 A1 | 7/2004 | Deadwyler et al. |
| 2004/0138580 A1 | 7/2004 | Frei et al. |
| 2004/0138581 A1 | 7/2004 | Frei et al. |
| 2004/0138647 A1 | 7/2004 | Osorio et al. |
| 2004/0138711 A1 | 7/2004 | Osorio et al. |
| 2004/0138721 A1 | 7/2004 | Osorio et al. |
| 2004/0147969 A1 | 7/2004 | Mann et al. |
| 2004/0152958 A1 | 8/2004 | Frei et al. |
| 2004/0153129 A1 | 8/2004 | Pless et al. |
| 2004/0158119 A1 | 8/2004 | Osorio et al. |
| 2004/0172089 A1 | 9/2004 | Whitehurst et al. |
| 2004/0176359 A1 | 9/2004 | Wermeling |
| 2004/0181263 A1 | 9/2004 | Balzer et al. |
| 2004/0199212 A1 | 10/2004 | Fischell |
| 2004/0210269 A1 | 10/2004 | Shalev et al. |
| 2004/0243146 A1 | 12/2004 | Chesbrough et al. |
| 2004/0267152 A1 | 12/2004 | Pineda et al. |
| 2005/0004621 A1 | 1/2005 | Boveja et al. |
| 2005/0010113 A1 | 1/2005 | Hall et al. |
| 2005/0010261 A1 | 1/2005 | Luders et al. |
| 2005/0015128 A1 | 1/2005 | Rezai et al. |
| 2005/0015129 A1 | 1/2005 | Mische |
| 2005/0021105 A1 | 1/2005 | Firlik et al. |
| 2005/0021108 A1 | 1/2005 | Klosterman et al. |
| 2005/0021313 A1 | 1/2005 | Nititin et al. |
| 2005/0027328 A1 | 2/2005 | Greenstein |
| 2005/0033369 A1 | 2/2005 | Badelt |
| 2005/0043772 A1 | 2/2005 | Stahmann et al. |
| 2005/0043774 A1 | 2/2005 | Devlin et al. |
| 2005/0049649 A1 | 3/2005 | Luders et al. |
| 2005/0059867 A1 | 3/2005 | Cheng |
| 2005/0070970 A1 | 3/2005 | Knudson et al. |
| 2005/0075067 A1 | 4/2005 | Lawson et al. |
| 2005/0096710 A1 | 5/2005 | Kieval |
| 2005/0113885 A1 | 5/2005 | Haubrich et al. |
| 2005/0124863 A1 | 6/2005 | Cook |
| 2005/0131493 A1 | 6/2005 | Boveja et al. |
| 2005/0137640 A1 | 6/2005 | Freeberg et al. |
| 2005/0143786 A1 | 6/2005 | Boveja |
| 2005/0143787 A1 | 6/2005 | Boveja et al. |
| 2005/0149123 A1 | 7/2005 | Lesser et al. |
| 2005/0182308 A1 | 8/2005 | Bardy |
| 2005/0182464 A1 | 8/2005 | Schulte et al. |
| 2005/0187789 A1 | 8/2005 | Hatlestad et al. |
| 2005/0197590 A1 | 9/2005 | Osorio et al. |
| 2005/0203366 A1 | 9/2005 | Donoghue et al. |
| 2005/0203584 A1 | 9/2005 | Twetan et al. |
| 2005/0209218 A1 | 9/2005 | Meyerson et al. |
| 2005/0222503 A1 | 10/2005 | Dunlop et al. |
| 2005/0222641 A1 | 10/2005 | Pless |
| 2005/0228249 A1 | 10/2005 | Boling |
| 2005/0228461 A1 | 10/2005 | Osorio et al. |
| 2005/0231374 A1 | 10/2005 | Diem et al. |
| 2005/0234355 A1 | 10/2005 | Rowlandson |
| 2005/0240245 A1 | 10/2005 | Bange et al. |
| 2005/0245970 A1 | 11/2005 | Erickson et al. |
| 2005/0245971 A1 | 11/2005 | Brockway et al. |
| 2005/0245984 A1 | 11/2005 | Singhal et al. |
| 2005/0266301 A1 | 12/2005 | Smith et al. |
| 2005/0277844 A1 | 12/2005 | Strother |
| 2006/0015034 A1 | 1/2006 | Martinerie et al. |
| 2006/0015153 A1 | 1/2006 | Gliner et al. |
| 2006/0094970 A1 | 5/2006 | Drew |
| 2006/0111644 A1 | 5/2006 | Guttag et al. |

(56) References Cited

U.S. PATENT DOCUMENTS

| | | |
|---|---|---|
| 2006/0122469 A1 | 6/2006 | Martel |
| 2006/0129056 A1 | 6/2006 | Leuthardt et al. |
| 2006/0142822 A1 | 6/2006 | Tulgar |
| 2006/0167371 A1* | 7/2006 | Flaherty et al. ............... 600/545 |
| 2006/0173259 A1 | 8/2006 | Flaherty et al. |
| 2006/0173510 A1 | 8/2006 | Besio et al. |
| 2006/0200038 A1 | 9/2006 | Savit et al. |
| 2006/0212092 A1 | 9/2006 | Pless et al. |
| 2006/0212093 A1 | 9/2006 | Pless et al. |
| 2006/0212096 A1 | 9/2006 | Stevenson |
| 2006/0217792 A1 | 9/2006 | Hussein et al. |
| 2006/0224191 A1 | 10/2006 | Dilorenzo |
| 2006/0253096 A1 | 11/2006 | Blakley et al. |
| 2006/0293578 A1 | 12/2006 | Rennaker, II |
| 2006/0293720 A1 | 12/2006 | DiLorenzo et al. |
| 2007/0027367 A1 | 2/2007 | Oliver et al. |
| 2007/0027514 A1 | 2/2007 | Gerber |
| 2007/0035910 A1 | 2/2007 | Stevenson |
| 2007/0043459 A1 | 2/2007 | Abbott, II et al. |
| 2007/0055320 A1 | 3/2007 | Weinand |
| 2007/0060973 A1 | 3/2007 | Ludvig et al. |
| 2007/0073355 A1 | 3/2007 | DiLorenzo |
| 2007/0073357 A1 | 3/2007 | Rooney et al. |
| 2007/0100398 A1 | 5/2007 | Sloan |
| 2007/0149952 A1 | 6/2007 | Bland et al. |
| 2007/0150024 A1 | 6/2007 | Leyde et al. |
| 2007/0150025 A1 | 6/2007 | DiLorenzo et al. |
| 2007/0161919 A1 | 7/2007 | DiLorenzo |
| 2007/0167991 A1 | 7/2007 | DiLorenzo |
| 2007/0185890 A1 | 8/2007 | VanEpps et al. |
| 2007/0197878 A1 | 8/2007 | Sklarski |
| 2007/0213629 A1 | 9/2007 | Greene |
| 2007/0213785 A1 | 9/2007 | Osorio et al. |
| 2007/0217121 A1 | 9/2007 | Fu et al. |
| 2007/0238939 A1 | 10/2007 | Giftakis et al. |
| 2007/0244407 A1 | 10/2007 | Osorio |
| 2007/0250077 A1 | 10/2007 | Skakoon et al. |
| 2007/0250901 A1 | 10/2007 | McIntire et al. |
| 2007/0287931 A1 | 12/2007 | DiLorenzo |
| 2008/0021341 A1 | 1/2008 | Harris et al. |
| 2008/0027347 A1 | 1/2008 | Harris et al. |
| 2008/0027348 A1 | 1/2008 | Harris et al. |
| 2008/0027515 A1 | 1/2008 | Harris et al. |
| 2008/0033502 A1 | 2/2008 | Harris et al. |
| 2008/0082019 A1 | 4/2008 | Ludving et al. |
| 2008/0091090 A1* | 4/2008 | Guillory et al. ............... 600/301 |
| 2008/0103556 A1 | 5/2008 | Li et al. |
| 2008/0114417 A1 | 5/2008 | Leyde |
| 2008/0119900 A1 | 5/2008 | DiLorenzo |
| 2008/0161712 A1 | 7/2008 | Leyde |
| 2008/0161713 A1 | 7/2008 | Leyde et al. |
| 2008/0183096 A1 | 7/2008 | Snyder et al. |
| 2008/0183097 A1 | 7/2008 | Leyde et al. |
| 2008/0208074 A1 | 8/2008 | Snyder et al. |
| 2008/0221876 A1 | 9/2008 | Holdrich |
| 2008/0255582 A1 | 10/2008 | Harris |
| 2008/0273287 A1 | 11/2008 | Marinkov et al. |
| 2008/0319281 A1 | 12/2008 | Aarts |
| 2009/0018609 A1 | 1/2009 | DiLorenzo |
| 2009/0062682 A1 | 3/2009 | Bland et al. |
| 2009/0062696 A1 | 3/2009 | Nathan et al. |
| 2009/0171168 A1 | 7/2009 | Leyde et al. |
| 2009/0171420 A1 | 7/2009 | Brown et al. |
| 2009/0264952 A1 | 10/2009 | Jassemidis et al. |
| 2010/0023089 A1 | 1/2010 | DiLorenzo |
| 2010/0125219 A1 | 5/2010 | Harris et al. |
| 2010/0145176 A1 | 6/2010 | Himes |
| 2010/0168603 A1 | 7/2010 | Himes et al. |
| 2010/0168604 A1 | 7/2010 | Echauz et al. |
| 2010/0179627 A1 | 7/2010 | Floyd et al. |
| 2010/0217348 A1 | 8/2010 | DiLorenzo |
| 2010/0292602 A1 | 11/2010 | Worrell et al. |
| 2010/0302270 A1 | 12/2010 | Echauz et al. |
| 2011/0166430 A1 | 7/2011 | Harris et al. |
| 2011/0172554 A1 | 7/2011 | Leyde et al. |
| 2011/0201944 A1 | 8/2011 | Higgins et al. |
| 2011/0213222 A1 | 9/2011 | Leyde et al. |
| 2011/0218820 A1 | 9/2011 | Himes et al. |
| 2011/0219325 A1 | 9/2011 | Himes et al. |
| 2011/0260855 A1 | 10/2011 | John et al. |
| 2011/0319785 A1 | 12/2011 | Snyder et al. |

FOREIGN PATENT DOCUMENTS

| | | |
|---|---|---|
| CA | 2428116 | 5/2002 |
| CA | 2428383 | 5/2002 |
| CA | 2425122 | 6/2002 |
| CA | 2425004 | 8/2002 |
| CA | 2456443 | 1/2003 |
| CA | 2491987 | 1/2004 |
| EP | 0124663 | 11/1984 |
| EP | 0898460 | 3/1999 |
| EP | 1145735 | 10/2001 |
| EP | 1145736 | 10/2001 |
| EP | 1307260 | 5/2003 |
| EP | 1335668 | 8/2003 |
| EP | 1525551 | 4/2005 |
| EP | 0911061 | 10/2005 |
| EP | 1609414 | 12/2005 |
| JP | 24033673 | 2/2004 |
| SU | 1074484 | 2/1984 |
| WO | 8501213 | 3/1985 |
| WO | 9200119 | 1/1992 |
| WO | 9726823 | 7/1997 |
| WO | 9734522 | 9/1997 |
| WO | 9734524 | 9/1997 |
| WO | 9734525 | 9/1997 |
| WO | 9739797 | 10/1997 |
| WO | 9742990 | 11/1997 |
| WO | 9745160 | 12/1997 |
| WO | 9849935 | 11/1998 |
| WO | 9920342 | 4/1999 |
| WO | 9956821 | 11/1999 |
| WO | 9956822 | 11/1999 |
| WO | 0007494 | 2/2000 |
| WO | 0010455 | 3/2000 |
| WO | 0141867 | 6/2001 |
| WO | 0148676 | 7/2001 |
| WO | 0149364 | 7/2001 |
| WO | 0167288 | 9/2001 |
| WO | 0175660 | 10/2001 |
| WO | 0209610 | 2/2002 |
| WO | 0209811 | 2/2002 |
| WO | 0236003 | 5/2002 |
| WO | 0238031 | 5/2002 |
| WO | 0238217 | 5/2002 |
| WO | 0249500 | 6/2002 |
| WO | 02058536 | 8/2002 |
| WO | 02067122 | 8/2002 |
| WO | 03001996 | 1/2003 |
| WO | 03009207 | 1/2003 |
| WO | 03030734 | 4/2003 |
| WO | 03035165 | 5/2003 |
| WO | 03084605 | 10/2003 |
| WO | 2004008373 | 1/2004 |
| WO | 2004032720 | 4/2004 |
| WO | 2004034231 | 4/2004 |
| WO | 2004034879 | 4/2004 |
| WO | 2004034880 | 4/2004 |
| WO | 2004034881 | 4/2004 |
| WO | 2004034882 | 4/2004 |
| WO | 2004034883 | 4/2004 |
| WO | 2004034885 | 4/2004 |
| WO | 2004034982 | 4/2004 |
| WO | 2004034997 | 4/2004 |
| WO | 2004034998 | 4/2004 |
| WO | 2004035130 | 4/2004 |
| WO | 2004036370 | 4/2004 |
| WO | 2004036372 | 4/2004 |
| WO | 2004036376 | 4/2004 |
| WO | 2004036377 | 4/2004 |
| WO | 2004037342 | 5/2004 |
| WO | 2004043536 | 5/2004 |
| WO | 2004091718 | 10/2004 |

(56) References Cited

FOREIGN PATENT DOCUMENTS

| WO | 2005007236 | 1/2005 |
|---|---|---|
| WO | 2005028026 | 3/2005 |
| WO | 2005028028 | 3/2005 |
| WO | 2005031630 | 4/2005 |
| WO | 2005051167 | 6/2005 |
| WO | 2005051306 A2 | 6/2005 |
| WO | 2005117693 | 12/2005 |
| WO | 2006014971 | 2/2006 |
| WO | 2006014972 | 2/2006 |
| WO | 2006020794 | 2/2006 |
| WO | 2006035392 | 4/2006 |

OTHER PUBLICATIONS

Adjouadi, et al. Detection of interictal spikes and artifactual data through orthogonal transformations. J. Clin. Neuorophysiol. 2005; 22(1):53-64.

Adjouadi, et al. Interictal spike detection using the Walsh transform. IEEE Trans. Biomed. Eng. 2004; 51(5):868-72.

Aksenova, et al. On-line disharmony detection for early prediction of epilepsy seizure onset. $5^{th}$ International Workshop Neural Coding 2003. Aulla (Italy) Sep. 20-25, 2003, (Abstract).

Aksevnova, et al. Nonparametric on-line detection of changes in signal spectral characteristics for early prediction of epilepsy seizure onset. J. Automation and Information Sciences. 2004; 36(8): 35-45.

Andrzejak, et al. Testing the null hypothesis of the nonexistence of a preseizure state. Physical Review E. 2003; 67: 010901-1-010901-4.

Andrzejak, et al. Bivariate surrogate techniques: necessity, strengths, and caveats. Physical Review E. 2003; 68: 066202-1-066202-15.

Aschenbrenner-Scheibe, et al. How well can epileptic seizures be predicted? An evaluation of a nonlinear method. Brain. 2003; 126: 2616-26.

Bangham et al. Diffusion of univalent ions across the lamellae of swollen phospholipids. 1965. J Mol. Biol. 13: 238-252.

Baruchi, et al. Functional holography of complex networks activity—From cultures to the human brain. Complexity. 2005; 10(3): 38 R 51.

Baruchi, et al. Functional holography of recorded neuronal networks activity. Neuroinformatics. 2004; 2(3): 333-51.

Ben-Hur, et al. Detecting stable clusters using principal component analysis. Methods Mol. Biol. 2003; 224: 159-82.

Bergey, et al. Epileptic seizures are characterized by changing signal complexity. Clin. Neurophysiol. 2001; 112(2): 241-9.

Betterton, et al. Determining State of Consciousness from the Intracranial Electroencephalogram (IEEG) for Seizure Prediction. From Proceeding (377) Modeling, Identification, and Control. 2003; 377-201: 313-317.

Bhattacharya, et al. Enhanced phase synchrony in the electroencephalograph gamma band for musicians while listing to music. Phys. Rev. E. 2001; 64:012902-1-4.

Boley, et al. Training Support Vector Machine using Adaptive Clustering. 2004 SIAM International Conference on Data Mining, Apr. 22-Apr. 24, 2004. Lake Buena Vista, FL, USA. 12 pages.

Burges, C. A Tutorial on Support Vector Machines for Pattern Recognition. Data Mining and Knowledge Discovery. 1998; 2: 121-167.

Cao, et al. Detecting dynamical changes in time series using the permutation entropy. Physical Review E. 2004; 70:046217-1-046217-7.

Carretero-Gonzalez, et al. Scaling and interleaving of subsystem Lyapunov exponents for spatio-temporal systems. Chaos. 1999; 9(2): 466-482.

Casdagli, et al. Characterizing nonlinearity in invasive EEG recordings from temporal lobe epilepsy. Physica D. 1996; 99 (2/3): 381-399.

Casdagli, et al. Nonlinear Analysis of Mesial Temporal Lobe Seizures Using a Surrogate Data Technique. Epilepsia. 1995; 36, suppl. 4, pp. 142.

Casdagli, et al. Non-linearity in invasive EEG recordings from patients with temporary lobe epilepsy. Electroencephalogr. Clin Neurophysiol. 1997; 102(2): 98-105.

Cerf, et al. Critically and synchrony of fluctuations in rhythmical brain activity: pretransitional effects in epileptic patients. Biol. Cybern. 2004; 90(4): 239-55.

Chaovalitwongse et al.; Reply to comments on "Performance of a seizure warning based on the dynamics of intracranial EEG"; Epilepsy Research, Elsevier Science Publishers, Amsterdam, NL; vol. 72; No. 1; pp. 82-84; Nov. 1, 2006.

Chaovalitwongse, et al. EEG Classification in Epilepsy. Annals. 2004; 2(37): 1-31.

Chaovalitwongse, et al. Performance of a seizure warning algorithm based on the dynamics of intracranial EEG. Epilepsy Res. 2005; 64(3): 93-113.

Chavez, et al Spatio-temporal dynamics prior to neocortical seizures: amplitude versphase couplings. IEEE Trans. Biomed. Eng. 2003; 50(5):571-83.

Chen et al.; Clinical utility of video-EEG monitoring; Perdiatric Neurology; vol. 12; No. 3; pp. 220-224; 1995.

Crichton, Michael, "Terminal Man", 1972, Ballantine Books, NY, NY, pp. 21-24, 3233, 70-71, and 74-81.

D'Alessandro, et al. A multi-feature and multi-channel univariate selection process for seizure prediction. Clin. Neurophysiol. 2005; 116(3): 506-16.

D'Alessandro, et al. Epileptic seizure prediction using hybrid feature selection over multiple intracranial EEG electrode contacts: a report of four patients. IEEE Trans. Biomed. Eng. 2003; 50(5): 603-15.

DiLorenzo, Daniel, U.S. Appl. No. 11/282,317 entitled "Closed-loop vag nerve stimulation," filed Nov. 17, 2005.

Drury, et al. Seizure prediction using scalp electroencephalogram. Exp. Neurol. 2003; 184 Suppl 1: S9-18.

Ebersole, J.S. In search of seizure prediction: a critique. Clin. Neurophysiol. 2005; 116(3); 489-92.

Elbert et al. Chaos and Physiology: Deterministic Chaos in Excitable Cell Assemblies. Physiological Reviews. 1994; 74(1):1-47.

Elger, et al. Nonlinear EEG analysis and its potential role in epileptology. Epilepsia. 2000; 41 Suppl 3: S34-8.

Elger, et al. Seizure prediction by non-linear time series analysis of brain electrical activity. Eur. J. Neurosci. 1998; 10(2): 786-789.

Esteller, et al. A Comparison of Waveform Fractal Dimension Algorithms. IEEE Transactions on Circuits and Systems. 2001; vol. 48(2): 177-183.

Esteller, et al. Continuoenergy variation during the seizure cycle: towards an on-line accumulated energy. Clin. Neurophysiol. 2005; 116(3): 517-26.

Esteller, et al. Feature Parameter Optimization for Seizure Detection/prediction. Proceedings of the $23^{rd}$ Annual International Conference of the IEEE Engineering in Medicine and Biology Society, Istanbul, Turkey. Oct. 2001.

Faul, et al. An evaluation of automated neonatal seizure detection methods. Clin. Neurophysiol. 2005; 116(7): 1533-41.

Fein, et al. Common reference coherence data are confounded by power and phase effects. Electroencephalogr. Clin. Neurophysiol. 1988; 69:581-584.

Fell, et al. Linear inverse filtering improves spatial separation of nonlinear brain dynamics: a simulation study. J. Neurosci. Methods. 2000; 98(1): 49-56.

Firpi, et al. Epileptic seizure detection by means of genetically programmed artificial features. GECCO 2005: Proceedings of the 2005 conference on Genetic and evolutionary computation, vol. 1, pp. 461-466, Washington DC, USA, 2005. ACM Press.

Fisher et al. 1999. Reassessment: Vagnerve stimulation for epilepsy, A report of the therapeutics and technology assessment subcommittee of the American Academy of Neurology. Neurology.53: 666-669.

Franaszczuk et al.; An autoregressive method for the measurement of synchronization of interictal and ictal EEG signals; Biological Cybernetics, vol. 81; No. 1; pp. 3-9; 1999.

(56) References Cited

OTHER PUBLICATIONS

Gardner, A. B. A Novelty Detection Approach to Seizure Analysis from Intracranial EEG. Georgia Institute of Technology. Apr. 2004. A dissertation available at http://etd.gatech.edu/theses/available/etd-04122004-132404/unrestricted/gardner_andrew_b_200405.

Geva, et al. Forecasting generalized epileptic seizures from the EEG signal by wavelet analysis and dynamic unsupervised fuzzy clustering. IEEE Trans. Biomed. Eng. 1998; 45(10): 1205-16.

Gigola, et al. Prediction of epileptic seizures using accumulated energy in a multiresolution framework. J. Neurosci. Methods. 2004; 138(1-2): 107-111.

Guyon, I. An introduction to variable and feature selection. Journal of Machine Learning Research. 2003; 3:1157-1182.

Guyon, I. Multivariate Non-Linear Feature Selection with Kernel Multiplicative Updates and Gram-Schmidt Relief. BISC FLINT-CIBI 2003 Workshop. Berkeley. 2003; p. 1-11.

Harrison, et al. Accumulated energy revised. Clin. Neurophysiol. 2005; 116(3):527-31.

Harrison, et al. Correlation dimension and integral do not predict epileptic seizures. Chaos. 2005; 15(3): 33106-1-15.

Hearst M. Trends & Controversies: Support Vector Machines. IEEE Intelligent Systems. 1998; 13: 18-28.

Hively, et al. Channel-consistent forewarning of epileptic events from scalp EEG. IEEE Trans. Biomed. Eng. 2003; 50(5): 584-93.

Hively, et al. Detecting dynamical changes in nonlinear time series. Physics Letters A. 1999; 258: 103-114.

Hively, et al. Epileptic Seizure Forewarning by Nonlinear Techniques. ORNL/TM-2000/333 Oak Ridge National Laboratory. Nov. 2000. Available at http://computing.ornl.gov/cse_home/staff/hively/NBICradaAnnualRpt_FY00.pdf. Accessed Feb. 28, 2006.

Hjorth, B. Source derivation simplifies topographical EEG interpretation. Am. J. EEG Technol. 1980; 20:121-132.

Hsu, et al. A practical guide to support vector classification. Technical report, Department of Computer Science and information Technology, National Taiwan University, 2003. Available at http://www.csie.ntu.edu.tw/~cjin/papers/guide/guide.pdf. Accessed Feb. 28, 2006.

Huynh, J. A. Evaluation of Gene Selection Using Support Vector Machine Recursive Feature Elimination. Presentation slides. (41 pages) (May 26, 2004).

Huynh, J. A. Evaluation of Gene Selection Using Support Vector Machine Recursive Feature Elimination. Arizona State University. May 26, 2004. (28 pages).

Iasemidis, et al. Adaptive epileptic seizure prediction system. IEEE Trans. Biomed. Eng. 2003; 50(5):616-27.

Iasemidis, et al. Automated Seizure Prediction Paradigm. Epilepsia. 1998; vol. 39, pp. 56.

Iasemidis, et al. Chaos Theory and Epilepsy. The Neuroscientist. 1996; 2:118-126.

Iasemidis, et al. Comment on "Inability of Lyapunov exponents to predict epileptic seizures." Physical Review Letters. 2005; 94(1):019801-1.

Iasemidis, et al. Detection of the Preictal Transition State in Scalp-Sphenoidal EEG Recordings. American Clinical Neurophysiology Society Annual Meeting, Sep. 1996. pp. C206.

Iasemidis, et al. Dynamical Interaction of the Epileptogenic Focwith Extrafocal Sites in Temporal Lobe Epilepsy (TLE). Ann. Neurol. 1997; 42, pp. 429. pp. M146.

Iasemidis, et al. Epileptogenic FocLocalization by Dynamical Analysis of Interictal Periods of EEG in Patients with Temporal Lobe Epilepsy. Epilepsia. 1997; 38, suppl. 8, pp. 213.

Iasemidis, et al. Localizing Preictal Temporal Lobe Spike Foci Using Phase Space Analysis. Electroencephalography and Clinical Neurophysiology. 1990; 75, pp. S63-S64.

Iasemidis, et al. Long-term prospective on-line real-time seizure prediction. Clin. Neurophysiol. 2005; 116(3): 532-44.

Iasemidis, et al. Long-Time-Scale Temporo-spatial Patterns of Entertainment of Preictal Electrocorticographic Data in Human Temporal Lobe Epilepsy. Epilepsia. 1990; 31(5):621.

Iasemidis, et al. Measurement and Quantification of Spatio-Temporal Dynamics of Human Epileptic Seizures. In: Nonlinear Signal Processing in Medicine, Ed. M. Akay, IEEE Press. 1999; pp. 1-27.

Iasemidis, et al. Modelling of ECoG in temporal lobe epilepsy. Biomed. Sci. Instrum. 1988; 24: 187-93.

Iasemidis, et al. Nonlinear Dynamics of EcoG Data in Temporal Lobe Epilepsy. Electroencephalography and Clinical Neurophysiology. 1998; 5, pp. 339.

Iasemidis, et al. Phase space topography and the Lyapunov exponent of electrocorticograms in partial seizures. Brain Topogr. 1990; 2(3): 187-201.

Iasemidis, et al. Preictal Entrainment of a Critical Cortical Mass is a Necessary Condition for Seizure Occurrence. Epilepsia. 1996; 37, suppl. 5. pp. 90.

Iasemidis, et al. Preictal-Postictal Vers Postictal Analysis for Epileptogenic Foc Localization. J. Clin. Neurophysiol. 1997; 14, pp. 144.

Iasemidis, et al. Quadratic binary programming and dynamic system approach to determine the predictability of epileptic seizures. Journal of Combinatorial Optimization. 2001; 5: 9-26.

Iasemidis, et al. Quantification of Hidden Time Dependencies in the EEG within the Framework of Non-Linear Dynamics. World Scientific. 1993; pp. 30-47.

Iasemidis, et al. Spatiotemporal dynamics of human epileptic seizures. World Scientific. 1996; pp. 26-30.

Iasemidis, et al. Spatiotemporal Evolution of Dynamical Measures Precedes Onset of Mesial Temporal Lobe Seizures. Epilepsia. 1994; 358, pp. 133.

Iasemidis, et al. Spatiotemporal Transition to Epileptic Seizures: A Nonlinear Dynamical Analysis of Scalp and Intracranial EEG Recordings. (In Silva, F.L. Spatiotemporal Models in Biological and Artificial Systems. Ohmsha IOS Press. 1997; 37, pp. 81-88.).

Iasemidis, et al. The evolution with time of the spatial distribution of the largest Lyapunov exponent on the human epileptic cortex. World Scientific. 1991; pp. 49-82.

Iasemidis, et al. The Use of Dynamical Analysis of EEG Frequency Content in Seizure Prediction. American Electroencephalographic Society Annual Meeting, Oct. 1993.

Iasemidis, et al. Time Dependencies in Partial Epilepsy. 1993; 34, pp. 130-131.

Iasemidis, et al. Time dependencies in the occurrences of epileptic seizures. Epilepsy Res. 1994; 17(1): 81-94.

Iasemidis, L. D. Epileptic seizure prediction and control. IEEE Trans. Biomed. Eng. 2003; 50(5):549-58.

Jerger, et al. Early seizure detection. Journal of Clin. Neurophysiol. 2001; 18(3):259-68.

Jerger, et al. Multivariate linear discrimination of seizures. Clin. Neurophysiol. 2005; 116(3):545-51.

Jouny, et al. Characterization of epileptic seizure dynamics using Gabor atom density. Clin. Neurophysiol. 2003; 114(3):426-37.

Jouny, et al. Signal complexity and synchrony of epileptic seizures: is there an identifiable preictal period? Clin. Neurophysiol. 2005; 116(3):552-8.

Kapiris, et al. Similarities in precursory features in seismic shocks and epileptic seizures. Europhys. Lett. 2005; 69(4);657-663.

Katz, et al. Does interictal spiking change prior to seizures? Electroencephalogr. Clin. Neurophysiol. 1991; 79(2):153-6.

Kerem, et al. Forecasting epilepsy from the heart rate signal. Med. Biol. Eng. Comput. 2005; 43(2):230-9.

Khalilov, et al. Epileptogenic actions of GABA and fast oscillations in the developing hippocampus. Neuron. 2005; 48(5):787-96.

Korn, et al. Is there chaos in the brain? II. Experimental evidence and related models. C. R. Biol. 2003; 326(9):787-840.

Kraskov, A. Synchronization and Interdependence Measures and Their Application to the Electroencephalogram of Epilepsy Patients and Clustering of Data. Available at http://www.kfa-juelich.de/nic-series/volume24/nic-series-brand24.pdf. Accessed Apr. 17, 2006 (106 pp.).

Kreuz, et al. Measure profile surrogates: a method to validate the performance of epileptic seizure prediction algorithms. Phys. Rev. E. 2004; 69(6 Pt 1):061915-1-9.

Lachaux, et al. Measuring phase synchrony in brain signals. Hum. Brain Mapp. 1999; 8(4):194-208.

(56) References Cited

OTHER PUBLICATIONS

Lai, et al. Controlled test for predictive power of Lyapunov exponents: their inability to predict epileptic seizures. Chaos. 2004; 14(3):630-42.

Lai, et al. Inability of Lyapunov exponents to predict epileptic seizures. Phys. Rev. Lett. 2003; 91(6):068102-1-4.

Latka, et al. Wavelet analysis of epileptic spikes. Phys. Rev. E. 2003; 67(5 Pt 1):052902 (6 pages).

Le Van Quyen, et al. Anticipating epileptic seizures in real time by a non-linear analysis of similarity between EEG recordings. Neuroreport. 1999; 10(10):2149-55.

Le Van Quyen, et al. Author's second reply. The Lancet. 2003; 361:971.

Le Van Quyen, et al. Comparison of Hilbert transform and wavelet methods for the analysis of neuronal synchrony. J. Neurosci. Methods. 2001; 111(2):83-98.

Le Van Quyen, et al. Nonlinear analyses of interictal EEG map the brain interdependences in human focal epilepsy. Physicia D. 1999; 127:250-266.

Le Van Quyen, et al. Preictal state identification by synchronization changes in long-term intracranial EEG recordings. Clin. Neurophysiol. 2005; 116(3):559-68.

Le Van Quyen, M. Anticipating epileptic seizures: from mathematics to clinical applications. C. R. Biol. 2005; 328(2):187-98.

Lehnertz, et al. Nonlinear EEG analysis in epilepsy: its possible use for interictal foc localization, seizure anticipation, and prevention. J. Clin. Neurophysiol. 2001; 18(3):209-22.

Lehnertz, et al. Seizure prediction by nonlinear EEG analysis. IEEE Eng. Med. Biol. Mag. 2003; 22(1):57-63.

Lehnertz, et al. The First International Collaborative Workshop on Seizure Prediction: summary and data description. Clin. Neurophysiol. 2005; 116(3):493-505.

Lehnertz, K. Non-linear time series analysis of intracranial EEG recordings in patients with epilepsy—and overview. Int. J. Psychophysiol. 1999; 34(1):45-52.

Lemos, et al. The weighted average reference montage. Electroencephalogr. Clin. Neurophysiol. 1991; 70(5):361-70.

Leyde et al.; U.S. Appl. No. 13/441,609 entitled "Multi-Channel Amplifier Techniques," filed Apr. 6, 2012.

Li, et al. Fractal spectral analysis of pre-epileptic seizures in terms of critically. J. Neural Eng. 2005; 2(2):11-16.

Li, et al. Linear and nonlinear measures and seizure anticipation in temporal lobe epilepsy. J. Comput. Neurosci. 2003; 15(3):335-45.

Li, et al. Non-linear, non-invasive method for seizure anticipation in focal epilepsy. Math. Biosci. 2003; 186(1):63-77.

Litt, et al. Prediction of epileptic seizures. Lancet Neurol. 2002; 1(1):22-30.

Litt, et al. Seizure prediction and the preseizure period. Curr. Opin. Neurol. 2002; 15(2):173-7.

Maiwald, et al. Comparison of three nonlinear seizure prediction methods by means of the seizure prediction characteristic. Physica D. 2004; 194:357-368.

Mangasarian, et al. Lagrangian Support Vector Machines. Journal of Machine Learning Research. 2001; 1:161-177.

Martinerie, et al. Epileptic seizures can be anticipated by non-linear analysis. Nat. Med. 1998; 4(10):1173-6.

McSharry, et al. Comparison of predictability of epileptic seizures by linear and a nonlinear method. IEEE Trans. Biomed. Eng. 2003; 50(5):628.33.

McSharry, et al. Linear and non-linear methods for automatic seizure detection in scalp electro-encephalogram recordings. Med. Biol. Eng. Comput. 2002; 40(4):447-61.

McSharry, P. E. Detection of dynamical transitions in biomedical signals using nonlinear methods. Lecture Notes in Computer Science 2004; 3215:483-490.

Meng, et al. Gaussian mixture models of ECoG signal features for improved detection of epileptic seizures. Med. Eng. Phys. 2004; 26(5):379-93.

Mizuno-Matsumoto, et al. Wavelet-crosscorrelation analysis can help predict whether bursts of pulse stimulation will terminate after discharges. Clin. Neurophysiol. 2002; 113(1):33-42.

Mormann et al.; Seizure prediction: the long and winding road; BRAIN; vol. 130; No. 2; pp. 314-333; Sep. 28, 2006.

Mormann, et al. Automated detection of a preseizure based on a decrease in synchronization in intracranial electroencephalogram recordings from epilepsy patients. Phys. Rev. E. 2003; 67(2 Pt 1):021912-1-10.

Mormann, et al. Epileptic seizures are preceded by a decrease in synchronization. Epilepsy Res. 2003; 53(3):173-85.

Mormann, et al. Mean phase coherence as a measure for phase synchronization and its application to the EEG of epilepsy patients. Physica D. 2000; 144:358-369.

Mormann, et al. On the predictability of epileptic seizures. Clin. Neurophysiol. 2005; 116(3):569-87.

Mormann, et al. Seizure anticipation: from algorithms to clinical practice. Curr. Opin. Neurol. 2006; 19(2):187-93.

Navarro, et al. Seizure anticipation in human neocortical partial epilepsy. Brain. 2002; 125:640-55.

Navarro, et al. Seizure anticipation: do mathematical measures correlate with video-EEG evaluation? Epilepsia. 2005; 46(3):385-96.

Niederhauser, et al. Detection of seizure precursors from depth-EEG using a sign periodogram transform. IEEE Trans. Biomed. Eng. 2003; 50(4):449-58.

Nigam, et al. A neural-network-based detection of epilepsy. Neurological Research. 2004; 26(1):55-60.

Osorio, et al. Automated seizure abatement in humans using electrical stimulation. Ann. Neurol. 2005; 57(2):258-68.

Osorio, et al. Performance reassessment of a real-time seizure-detection algorithm on long ECoG series. Epilepsia. 2002; 43(12):1522-35.

Osorio, et al. Real-time automated detection and quantitative analysis of seizures and short-term prediction of clinical onset. Epilepsia. 1998; 39(6):615-27.

Ossadtchi, et al. Hidden Markov modeling of spike propagation from interictal MEG data. Phys. Med. Biol. 2005; 50(14):3447-69.

Pflieger, et al. A noninvasive method for analysis of epileptogenic brain connectivity. Presented at the American Epilepsy Society 2004 Annual meeting, New Orleans. Dec. 6, 2004. Epilepsia. 2004; 45(Suppl. 7):70-71.

Pittman, V. Flexible Drug Dosing Produces Less Side-effects in People With Epilepsy. Dec. 29, 2005. Available at http://www.medicalnewstoday.com/medicalnews.php?newsid=35478. Accessed on Apr. 17, 2006.

Platt, et al. Large Margin DAGs for Multiclass Classification. S.A. Solla. T.K. Leen and K.R. Muller (eds.). 2000; pp. 547-553.

Platt, J. C. Using Analytic QP and Sparseness to Speed Training of Support Vector Machines. Advances in Neural Information Processing Systems. 1999; 11:557-563.

Protopopescu, et al. Epileptic event forewarning from scalp EEG. J. Clin. Neurophysiol. 2001; 18(3):223-45.

Rahimi, et al. On the Effectiveness of Aluminum Foil Helmets; An empirical Study Available at http://people.csail.mit.edu/rahimi/helmet/. Accessed Mar. 2, 2006.

Robinson, et al. Steady States and Global Dynamics of Electrical Activity in the Cerebral Coretex. Phys. Rev. E. 1998; (58):3557-3571.

Rothman et al.; Local Cooling: a therapy for intractable neocortical epilepsy; Epilepsy Currents; vol. 3; No. 5; pp. 153-156; Sep./Oct. 2003.

Rudrauf, et al. Frequency flows and the time-frequency dynamics of multivariate phase synchronization in brain signals. NeuroImage. 2005. (19 pages).

Saab, et al. A system to detect the onset of epileptic seizures in scalp EEG. Clin. Neurophysiol. 2005; 116:427-442.

Sackellares et al. Computer-Assisted Seizure Detection Based on Quantitative Dynamical Measures. American Electroencephalographic Society Annual Meeting, Sep. 1994.

Sackellares et al. Dynamical Studies of Human Hippocampin Limbic Epilepsy. Neurology. 1995; 45, Suppl. 4, pp. A 404.

(56) References Cited

OTHER PUBLICATIONS

Sackellares et al. Epileptic Seizures as Neural Resetting Mechanisms. Epilepsia. 1997; vol. 38, Sup. 3.
Sackellares et al. Measurement of Chaos to Localize Seizure Onset. Epilepsia. 1989; 30(5):663.
Sackellares et al. Predictability Analysis for an Automated Seizure Prediction algorrithim; Journal of Clinical Neurophysiology; vol. 23; No. 6; pp. 509-520; Dec. 2006.
Sackellares et al. Relationship Between Hippocampal Atrophy and Dynamical Measures of EEG in Depth Electrode Recordings. American Electroencephalographic Society Annual Meeting, Sep. 1995. pp. A105.
Sackellares, J. C. Epilepsy—when chaos fails. In: chaos in the brain? Eds. K. Lehnertz & C.E. Elger. World Scientific. 2000 (22 pages).
Salant, et al. Prediction of epileptic seizures from two-channel EEG. Med. Biol. Eng. Comput. 1998; 36(5):549-56.
Schelter et al.; Testing statistical significance of multivariate time series analysis techniques for epileptic seizure prediction; Chaos;: An Interdisciplinary Journal of Nonlinear Science; vol. 16; No. 013108; pp. 1-10; Jan. 2006.
Schelter, et al. Testing for directed influences among neural signals using partial directed coherence. J. Neurosci. Methods. 2006; 152-(1-2):210-9.
Schindler, et al. EEG analysis with simulated neuronal cell models helps to detect pre-seizure changes. Clin. Neurophysiol. 2002; 113(4):604-14.
Schwartzkroin, P. Origins of the Epileptic State. Epilepsia. 1997; 38, supply. 8, pp. 853-858.
Sheridan, T. Humans and Automation. NY: John Wiley. 2002.
Shoeb et al. Patient-specific seizure detection. MIT Computer Science and Artificial Intelligence Laboratory. 2004; pp. 193-194.
Snyder et al; The statistics of a practical seizure warning system; Journal of Neural Engineering; vol. 5; pp. 392-401; 2008.
Spector et al.; High and Low Perceived Self-Control of Epileptic Seizures; Epilepsia, vol. 42(4), Apr. 2001; pp. 556-564.
Staba, et al. Quantitative analysis of high-frequency oscillations (80-500 Hz) recorded in human epileptic hippocampand entorhinal cortex. J. Neurophysiol. 2002; 88(4): 1743-52.
Stefanski, et al. Using chaos synchronization to estimate the largest Lyapunov exponent of nonsmooth systems. discrete Dynamics in Nature and Society. 2000; 4:207-215.
Subasi, et al. Classification of EEG signals using neural network and logistic regression. Computer Methods Programs Biomed. 2005; 78(2):87-99.
Szoka et al. Procedure for preparation of liposomes with large internal aqueospace and high capture volume by reverse phase evaporation. 1978 Proc. Natl Acad. Sci. USA. 75: 4194-4198.
Tass, et al. Detection of n: m Phase Locking from Noisy Data: Application to Magnetoencephalography. Physical Review Letters. 1998; 81(15):3291-3294.
Terry, et al. An improved algorithm for the detection of dynamical interdependence in bivariate time-series. Biol. Cybern. 2003; 88(2):129-36.
Tetzlaff, et al. Cellular neural networks (CNN) with linear weight functions for a prediction of epileptic seizures. Int'l J. of Neural Systems. 2003; 13(6):489-498.
Theiler, et al. Testing for non-linearity in time series: the method of surrogate data. Physica D. 1992; 58:77-94.

Van Drongelen, et al. Seizure anticipation in pediatric epilepsy: use of Kolmogorov entropy. Pediatr. Neurol. 2003; 29(3): 207-13.
Van Putten, M. Nearest neighbor phase synchronization as a measure to detect seizure activity from scalp EEG recordings. J. Clin. Neurophysiol. 2003; 20(5):320-5.
Venugopal, et al. A new approach towards predictability of epileptic seizures: KLT dimension. Biomed Sci. Instrum. 2003; 39:123-8.
Vonck, et al. Long-term amygdalohippocampal stimulation for refractory temporal lobe epilepsy. Ann. Neurol. 2002; 52(5):556-65.
Vonck, et al. Long-term deep brain stimulation for refractory temporal lobe epilepsy. Epilepsia. 2005; 46 (Suppl 5):98-9.
Vonck, et al. Neurostimulation for refractory epilepsy. Acta. Neurol. Belg. 2003; 103(4):213-7.
Weiss, P. Seizure prelude found by chaos calculation. Science News. 1998; 153(20):326.
Wells, R. B. Spatio-Temporal Binding and Dynamic Cortical Organization: Research Issues. Mar. 2005. Available at http://www.mrc.uidaho.edu/~rwells/techdocs/Functional%20Column%20Research%20Issues.pdf. Accessed Mar. 2, 2006.
Widman, et al. Reduced signal complexity of intracellular recordings: a precursor for epileptiform activity? Brain Res. 1999; 836(1-2):156-63.
Winterhalder, et al. Sensitivity and specificity of coherence and phase synchronization analysis. (In Press) Phys. Lett. A. 2006.
Winterhalder, et al. The seizure prediction characteristic: a general framework to assess and compare seizure prediction methods. Epilepsy Behay. 2003; 4(3):318-25.
Wong et al.; A stochastic framework for evaluating seizure prediction algorithms using hidden markov models; Journal of Neurophysiology; vol. 97, No. 3; pp. 2525-2532; Oct. 4, 2006.
Yang et al.; Testing whether a prediction scheme is better than guess; Ch. 14 in Quantitative Neuroscience: Models, Algorithms, Diagnostics, and Therapeutic Applications; pp. 252-262; 2004.
Yang, et al. A supervised feature subset selection technique for multivariate time series. Available at http://infolab.usc.edu/DocsDemos/fsdm05.pdf. Accessed Mar. 2, 2006.
Yang, et al. CLe Ver: A feature subset selection technique for multivariate time series. T.B. Ho, D. Cheung, and H. Liu (Eds.): PAKDD. 2005; LNAI 3518: 516-522.
Yang, et al. Relation between Responsiveness to Neurotransmitters and Complexity of Epileptiform Activity in Rat Hippocampal CA1 Neurons. Epilepsia. 2002; 43(11):1330-1336.
Yatsenko, et al. Geometric Models, Fiber Bundles, and Biomedical Applications. Proceedings of Institute of Mathematics of NAS of Ukraine. 2004; 50 (Part 3):1518R1525.
Zaveri et al. Time-Frequency Analyses of Nonstationary Brain Signals. Electroencephalography and Clinical Neurophysiology. 1991; 79, pp. 28P-29P).
Zhang, et al. High-resolution EEG: cortical potential imaging of interictal spikes. Clin. Neurophysiol. 2003; 114(10):1963-73.
Ebersole, J.S. Functional neuroimaging with EEG source models to localize epileptogenic foci noninvasively. Neurology. Available at http://www.uchospitals.edu/pd/uch_0014471, Accessed Feb. 28, 2006.
Tsakalis, K. S. Prediction and control of epileptic seizures: Coupled oscillator models. Arizona State University. (Slide: 53 pages) (No date).

\* cited by examiner

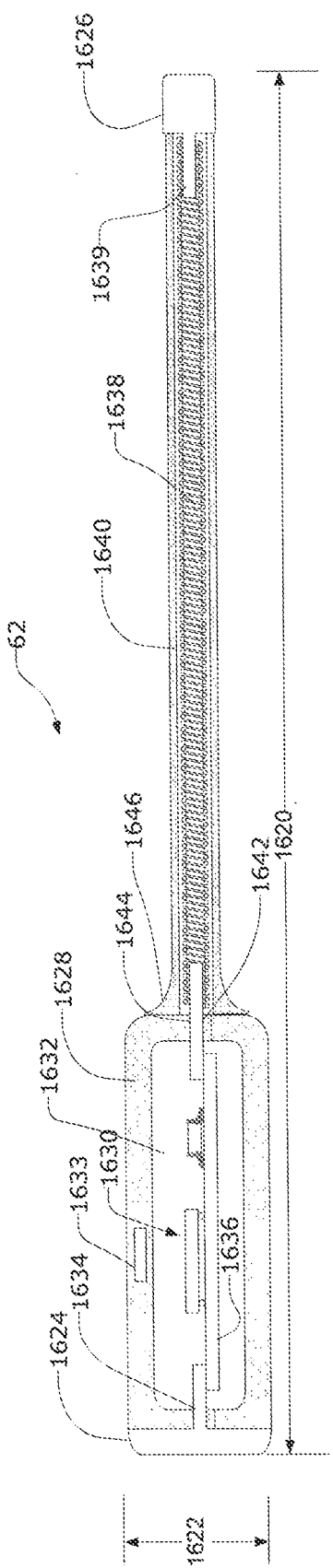
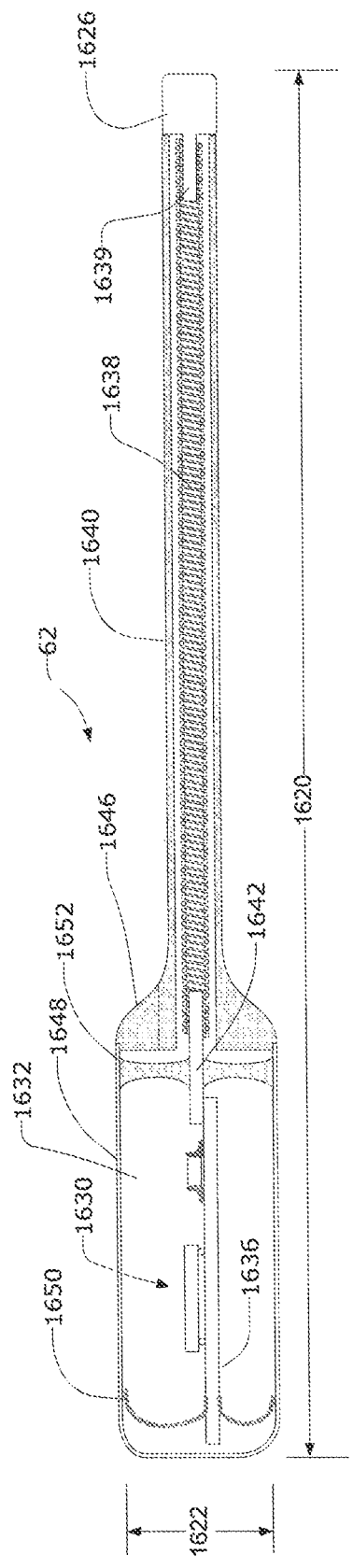

IMPLANTABLE SYSTEMS AND METHODS FOR IDENTIFYING A CONTRA-ICTAL CONDITION IN A SUBJECT

CROSS-REFERENCE TO RELATED APPLICATIONS

This application is a continuation of U.S. patent application Ser. No. 13/225,241, filed Sep. 2, 2011, which is a continuation of U.S. patent application Ser. No. 12/053,312, filed Mar. 21, 2008, now U.S. Pat. No. 8,036,736, which claims the benefit of priority to U.S. Provisional Patent Application No. 60/919,364, filed Mar. 21, 2007, the disclosures of which are incorporated by reference herein in their entirety.

BACKGROUND OF THE INVENTION

The present invention relates generally to systems and methods for monitoring a subject's neurological condition. More specifically, the present invention is related to minimally invasive methods and systems for monitoring a subject who has epilepsy and determining if the subject is in a contra-ictal condition in which the subject is at low susceptibility for a seizure and is unlikely to transition into a pre-seizure condition within a computed or predetermined time period.

Epilepsy is a disorder of the brain characterized by chronic, recurring seizures. Seizures are a result of uncontrolled discharges of electrical activity in the brain. A seizure typically manifests itself as sudden, involuntary, disruptive, and often destructive sensory, motor, and cognitive phenomena. Seizures are frequently associated with physical harm to the body (e.g., tongue biting, limb breakage, and burns), a complete loss of consciousness, and incontinence. A typical seizure, for example, might begin as spontaneous shaking of an arm or leg and progress over seconds or minutes to rhythmic movement of the entire body, loss of consciousness, and voiding of urine or stool.

A single seizure most often does not cause significant morbidity or mortality, but severe or recurring seizures (epilepsy) results in major medical, social, and economic consequences. Epilepsy is most often diagnosed in children and young adults, making the long-term medical and societal burden severe for this population of subjects. People with uncontrolled epilepsy are often significantly limited in their ability to work in many industries. An uncommon, but potentially lethal form of seizure is called status epilepticus, in which a seizure continues for more than 30 minutes. This continuous seizure activity may lead to permanent brain damage, and can be lethal if untreated.

While the exact cause of epilepsy is often uncertain, epilepsy can result from head trauma (such as from a car accident or a fall), infection (such as meningitis), or from neoplastic, vascular, or developmental abnormalities of the brain. Most epilepsy, especially most forms that are resistant to treatment (i.e., refractory), are idiopathic or of unknown causes, and are generally presumed to be an inherited genetic disorder. Demographic studies have estimated the prevalence of epilepsy at approximately 1% of the population, or roughly 2.5 million individuals in the United States alone. Approximately 60% of these subjects have focal epilepsy where a defined point of onset can be identified in the brain and are therefore candidates for some form of a focal treatment approach.

If it is assumed that an "average" subject with focal epilepsy has between 3 and 4 seizures per month, in which each of the seizures last for several seconds or minutes, the cumulative time the subject would be seizing is only about one hour per year. The other 99.98% of the year, the epileptic subject is free from seizures. The debilitating aspect of epilepsy is the constant uncertainty of when the next seizure is going to strike. It is this constant state of uncertainty which causes epileptic subjects to remove themselves from society. It is the constant fear and uncertainty of when the next seizure will strike that prevents the person from performing activities that most non-epileptic subjects take for granted.

To that end, there have been a number of proposals from groups around the world for predicting seizures and warning the subject of the impending seizure. Most of such proposals attempt to analyze the subject's electroencephalogram or electrocorticograms (referred to collectively as "EEGs"), to differentiate between a "pre-ictal condition" (i.e., pre-seizure condition) and an "inter-ictal condition" (i.e., between seizures). To date, however, none of the proposed systems have proven to be effective in predicting seizures. Some researchers have proposed that seizures develop minutes to hours before the clinical onset of the seizure. These researchers therefore classify the pre-ictal condition as the beginning of the ictal or seizure event which begins with a cascade of events. Under this definition, a seizure is imminent and will occur if a pre-ictal condition is observed. Others believe that a pre-ictal condition represents a state which only has a high susceptibility for a seizure and does not always lead to a seizure, and that seizures occur either due to chance (e.g., noise) or via a triggering event during this high susceptibility time period. For clarity, the term "pro-ictal" is introduced here to represent a state or condition that represents a high susceptibility for seizure; in other words, a seizure can happen at any time. Ictal activity, within the scope of epilepsy, refers to seizure activity. Ictal activity may have other meanings in other contexts.

SUMMARY OF THE INVENTION

Prior art seizure detection and warning systems focused only on the identification of ictal or pro-ictal physiological data from the subject. See, e.g., Litt U.S. Pat. No. 6,658,287. While being able to determine that the subject is in a "pro-ictal" condition is highly desirable, identifying when the subject has entered or is likely to enter a pro-ictal condition is only part of the solution for these subjects. An equally important aspect of any seizure advisory system is the ability to be able to inform the subject when they are unlikely to have a seizure for a predetermined period of time (e.g., low susceptibility or "contra-ictal"). Simply knowing that the subject is not pro-ictal does not provide the subject with the assurance that they will not quickly transition into a pro-ictal or ictal condition. Knowing that they are in a contra-ictal state can allow the subject to engage in normal daily activities, such as walking down a set of stairs, without fearing that they will have a seizure. Knowing when a seizure is unlikely to occur can be even more important for the subject's sense of freedom than being alerted when a seizure is likely to occur.

Furthermore, for one reason or another, it may not be possible to accurately predict the seizures in a portion of the subject population. However, for that same portion of the subject population, it may be possible to let the subject know when they are unlikely to have a seizure for a period of time.

Accordingly, it would be desirable to provide methods and systems that are able to inform the subject that they are highly unlikely to transition into a pro-ictal or ictal condition in a period of time. It would further be desirable if such systems and methods could substantially continuously provide an output to the subject in a minimally invasive fashion to differentiate when the subject is at a low susceptibility to seizure, raised susceptibility to seizure, and/or a high susceptibility to seizure.

Systems and methods are described herein for identifying a state or condition in which the subject is unlikely to transition to an ictal state or condition within a time period. Such a state is described herein as a "contra-ictal" condition or state. If it is determined that the subject is in the contra-ictal state, a communication is output to the subject that is indicative of the subject being in the contra-ictal state.

In some embodiments, the present invention may provide a substantially continuous output to the subject that indicates the subject's real-time susceptibility to a seizure for a time period. The output may provide an indication that the subject is at a high susceptibility to a seizure (e.g., seizure prediction or determination of being in a pre-ictal condition), a mild or normal susceptibility to a seizure (e.g., the subject is in an inter-ictal state), or a low susceptibility to a seizure (e.g., the subject appears to be highly unlikely to have a seizure within a time period).

The term "state" is used herein to generally refer to calculation results or indices that are reflective of the state of the subject's neural system, but does not necessarily constitute a complete or comprehensive accounting of the subject's total neurological condition. The estimation and characterization of "state" may be based on one or more subject dependent parameters from the brain, such as electrical signals from the brain, including but not limited to electroencephalogram signals "EEG" and electrocorticogram signals "ECoG" (referred to herein collectively as "EEG"), brain temperature, blood flow in the brain, concentration of anti-epileptic drugs (AEDs) in the brain, or other physiological signals.

The term "pro-ictal" is used herein to refer to a neurological state or condition characterized by an increased likelihood of transition to an ictal state. A pro-ictal state may transition to either an ictal or inter-ictal state. A pro-ictal state that transitions to an ictal state is also referred to as pre-ictal.

Minimally-invasive systems that provide for the long-term, ambulatory monitoring of subject's brain activity are described. These systems will typically include one or more implantable devices that may be minimally invasively implanted in the subject. The implantable device may be adapted to sample a physiological signal from a subject. A processing assembly processes a data signal from the implantable device to determine if the subject is in a contra-ictal condition. If the subject is determined to be in a contra-ictal condition, a user interface provides an output to the subject that indicates that the subject is in the contra-ictal condition.

The data signal can be indicative of the physiological signal and can be substantially continuously transmitted substantially in real-time from the implanted minimally invasive leadless device to the processing assembly. The data signal can comprise a compressed EEG signal or an encrypted EEG signal, or it may comprise an extracted feature from a physiological signal from the subject. The user interface can provide a substantially continuous output to the subject regarding the subject's condition.

The minimally invasive leadless device can be in wireless communication with the processing assembly. The processing assembly and the user interface can both be part of a patient handheld device.

The contra-ictal condition can include a condition in which the subject is at a low susceptibility to having a seizure within a time period.

The output to the subject that indicates that the subject is in the contra-ictal condition can comprise an audible output, a tactile output, a visual output on a display, or a combination thereof. The output to the subject can comprise, e.g., a green light.

In another embodiment, a seizure advisory system is provided comprising an implanted leadless device that is configured to sample an EEG signal (or other physiological signal) from a subject and transmit a wireless signal from the subject's body to a subject advisory device that is external to the subject's body. The subject advisory device comprises a processing assembly that processes the wireless signal to determine if the subject is in a contra-ictal condition. If the user is determined to be in a contra-ictal condition, a user interface of the subject advisory device provides an output to the subject that indicates that the subject is in the contra-ictal condition.

The subject advisory device can comprise a memory for storing the wireless signal. The contra-ictal condition can be a neurological state in which the subject is unlikely to transition into an ictal condition within a time period. The time period can be a predetermined time period.

The leadless device can be adapted to be implanted between the subject's dura and scalp, and preferably between the subject's skull and scalp.

In yet another embodiment, a method of monitoring a subject's neurological condition is provided. The method comprises implanting a device in the subject. In one embodiment, the device is implanted in a minimally invasive fashion. Typically, the devices are leadless and are implanted between a subject's skull and scalp. A physiological signal sampled by the implanted devices is analyzed to determine if the subject is in a contra-ictal condition. If the subject is in a contra-ictal condition, an output is provided to the subject that is indicative of the subject being in the contra-ictal condition.

The physiological signal can be an EEG signal. The contra-ictal condition can be a neurological state in which the subject is unlikely to transition into an ictal condition within a time period. The time period can be a predetermined time period.

Analyzing the physiological signal can comprise extracting N features from the physiological signal, generating a N-dimensional feature vector of the extracted N features for time points of the physiological signal, and determining if the N-dimensional feature vector is within a contra-ictal cluster or region in the N-dimensional space.

For a further understanding of the nature and advantages of the present invention, reference should be made to the following description taken in conjunction with the accompanying drawings.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 16A is a cross-sectional view of another embodiment of an implantable device that is encompassed by the present invention.

FIG. 16B is a cross-sectional view of another embodiment of the implantable device in which a conductive can forms a housing around the electronic components and acts as an electrode.

DETAILED DESCRIPTION OF THE INVENTION

Figure 1A:
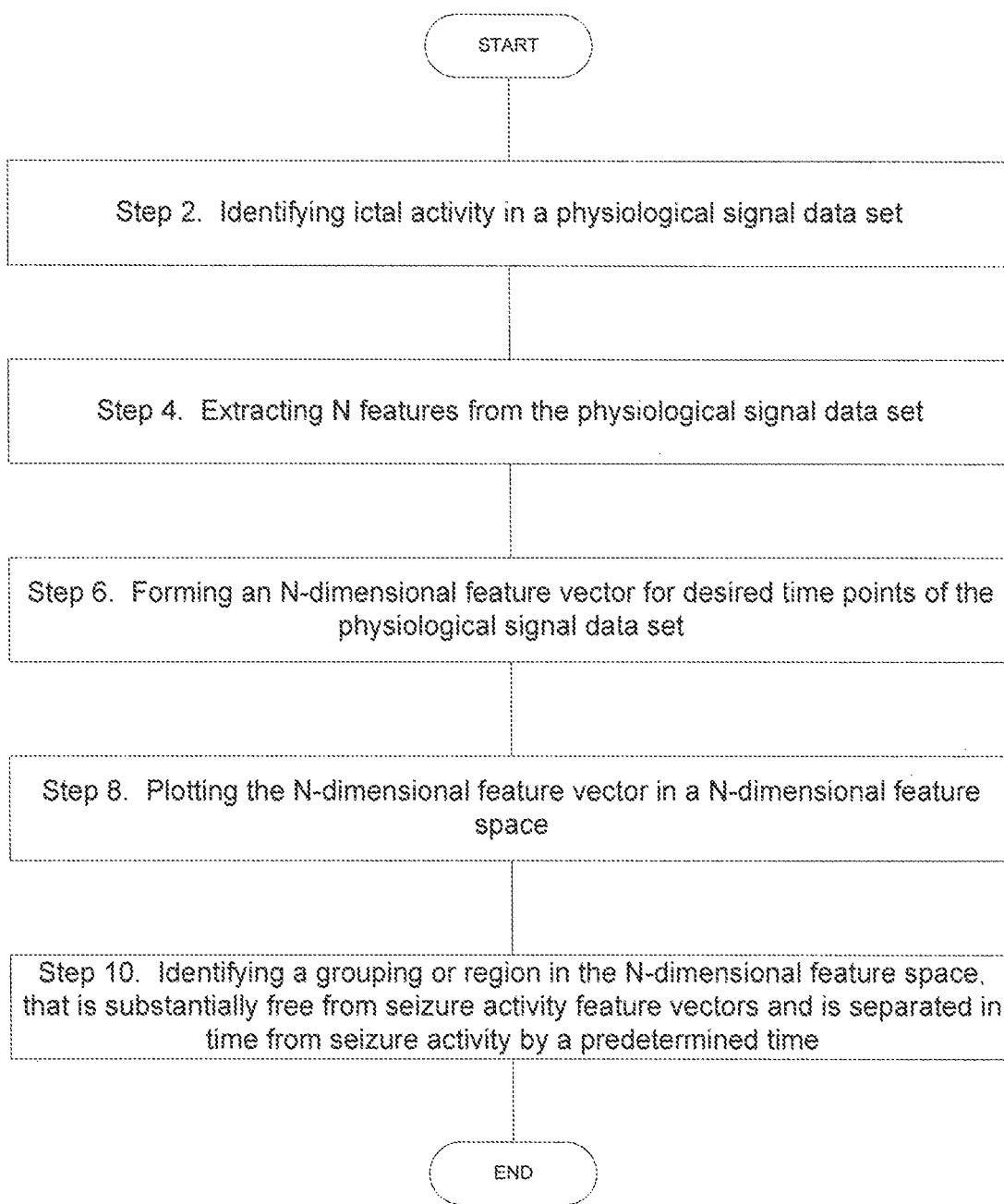
FIG. 1A is a simplified method of identifying a contra-ictal condition in a subject data set according to one embodiment of the invention.

Certain specific details are set forth in the following description and figures to provide an understanding of various embodiments of the invention. Certain well-known details, associated electronics and devices are not set forth in the following disclosure to avoid unnecessarily obscuring the various embodiments of the invention. Further, those of ordinary skill in the relevant art will understand that they can practice other embodiments of the invention without one or more of the details described below. Finally, while various processes are described with reference to steps and sequences in the following disclosure, the description is for providing a clear implementation of particular embodiments of the invention, and the steps and sequences of steps should not be taken as required to practice this invention.

While the discussion below focuses on measuring electrical signals generated by electrodes placed near, on, or within the brain or nervous system (EEG signals) of subjects and subject populations for the determination of when an epileptic subject is in a contra-ictal condition, it should be appreciated that the invention is not limited to measuring EEG signals or to determining when the subject is in a contra-ictal state. For example, the invention could also be used in systems that measure one or more of a blood pressure, blood oxygenation (e.g., via pulse oximetry), temperature of the brain or of portions of the subject, blood flow measurements, ECG/EKG, heart rate signals, respiratory signals, chemical concentrations of neurotransmitters, chemical concentrations of medications, pH in the blood, or other physiological or biochemical parameters of a subject.

Furthermore, while the remaining discussion focuses on identifying a contra-ictal condition for epileptic subjects, the present invention may also be applicable to monitoring other neurological or psychiatric disorders and identifying a condition or state for such disorders in which the subject is unlikely to experience some adverse effect. For example, the present invention may also be applicable to monitoring and management of sleep apnea, Parkinson's disease, essential tremor, Alzheimer's disease, migraine headaches, depression, eating disorders, cardiac arrhythmias, bipolar spectrum disorders, or the like. As can be appreciated, the features extracted from the signals and used by the algorithms will be specific to the underlying disorder that is being managed. While certain features may be relevant to epilepsy, such features may or may not be relevant to the state measurement for other disorders.

One embodiment of the present invention identifies and uses a contra-ictal classification for each subject in which the subject is highly unlikely to transition to the ictal state within a specified time period. The contra-ictal condition can be considered to be a subset of the inter-ictal class or it can be considered to be a completely new neurological classification. While it is beneficial to the subject to know if the subject is in the inter-ictal condition, being in the inter-ictal condition does not necessarily inform the subject that they will not quickly transition from the inter-ictal condition to the ictal condition. Being able to inform a subject that they are in a contra-ictal state can allow the subject to engage in normal daily activities, such as walking down a set up stairs, without fearing that they will have a seizure or without fearing that they may quickly transition into a pro-ictal state. Knowing when a seizure is unlikely to occur can be even more important to the subject's freedom than being alerted when a seizure is likely to occur.

The period of time associated with the contra-ictal state will vary depending on the implementation of the algorithm. The period of time could be a predetermined time period as determined from the training data and programmed into the algorithm, such as 10 minutes, 20 minutes, 30 minutes, 60 minutes, 90 minutes or more. In other implementations, the algorithm could compute the period, which may be different from episode to episode for a single subject. Thus, for some subjects, the period of time could span many hours or even days or weeks.

Proposed seizure prediction systems only attempt to differentiate between a pre-ictal state and an inter-ictal state for purposes of seizure prediction. Advantageously, embodiments of the present invention may further identify the contra-ictal condition or state for the particular subject.

FIG. 1A illustrates a simplified method of identifying a contra-ictal state for the subject. The method of FIG. 1A is typically performed in a computer system in a physician's office, but it could also be performed in a central processing computer workstation remote from the physician, or even in a subject's external data device or implanted communication unit (shown in FIG. 9).

At step 2, a training dataset of the subject is obtained and annotated to identify the ictal activity. The training data could span days or weeks, and is preferably a substantially continuous monitoring of the subject's EEG signals using an array of scalp or intracranial electrodes. Preferably the training data comprises a plurality of ictal events separated by inter-ictal intervals. For epilepsy, the training set of physiological signals typically includes a training set of intracranial EEG recordings from the subject's long term visit to an epilepsy monitoring unit (EMU). However, the EEG training sets could be obtained from the ambulatory system utilizing an implantable device and external device as described below.

While EEG signals are currently the desirable physiological signals that are analyzed, any of the aforementioned physiological signals could be used to train the algorithms. As is known in the art, the training set may be overlaid with comments from a physician and/or a marking algorithm may automatically identify some or all of the ictal activity in the training set—such as epileptiform spikes, earliest electrographic change (EEC), unequivocal electrical onset of seizure (UEO), unequivocal clinical onset (UCO), end of electrographic seizure (EES), etc. The following Steps 4-10 which are described in the subsequent paragraphs are directed towards EEG signals, however, such analysis may also be applied to the aforementioned other physiological signals.

At step 4, N feature extractors may be applied to the training set to quantify relevant aspects of the EEG training dataset. Any number of features can be extracted from the EEG signals in order to assess the subject's condition. At step 6, for each desired point in time in the EEG training dataset, an N-dimensional feature vector will be formed for each of the N features that are extracted. At step 8, if desired, the extracted N-dimensional feature vectors may then be allocated or plotted in an N-dimensional feature space. While not shown in FIG. 1A, the invention may also be used with lower dimension spaces created through application of data transformations to the N-dimensional feature vector, including but not limited to, principle components analysis, factor analysis, or linear discriminant analysis. For ease of reference, FIGS. 3 to 8 illustrate a plot of feature vectors across a two dimensional space (N=2), but it should be appreciated that any dimensional space could be used with the present invention.

Since it is not likely for the physician or training system to identify a contra-ictal period a priori, one aspect of the present invention utilizes an unsupervised learning protocol to identify a contra-ictal condition for the subject by utilizing an algorithm or other means to identify a region of the feature space or clusters or groupings of feature vectors in the N-dimensional feature space that are substantially devoid of feature vectors that are in an ictal condition and for which all feature vectors in the grouping or region are separated from an ictal event (e.g., seizure) by a predetermined time period (step 10). For example, the N-dimensional feature space may be partitioned into a collection of N-dimensional hypercubes. A hypercube that is substantially devoid of training vectors that occur within a predetermined time period prior to the next seizure may be labeled contra-ictal. In another implementation, a binary space partitioning algorithm can be used to partition the N-dimensional feature space into a collection of N-dimensional hyperprisms. A hyperprism that is substantially devoid of training vectors that occur within a predetermined time period prior to the next seizure may be labeled contra-ictal. In another implementation, the structure of the training data may be approximated by an expansion of radial basis function, e.g. a Gaussian mixture model. Each feature vector in the training data may be assigned to one component of the radial basis function expansion using, e.g., Bayesian posterior probability or decision risk criteria. A component that is substantially devoid of training vectors that occur within a predetermined time period prior to the next seizure may be labeled contra-ictal. The algorithm may also identify other classes of interest from the EEG training dataset (e.g., inter-ictal that is not part of the contra-ictal class, pro-ictal, ictal, post-ictal, or the like), and the classes of interest (or groupings of feature vectors) for the subject and/or mathematical representations thereof are stored in memory for later use in the subject system implanted or otherwise used by the subject.

It is further noted that each identified partition in the N-dimensional feature space can be assigned an identifier that may be used to represent states in a Markov chain, or symbols emitted by hidden states in a hidden Markov model. These identifiers, or sequences of identifiers may be used to make inferences about future states, and thereby the likelihood of seizure occurrence.

Similar approaches may be used to derive and train a pro-ictal algorithm. For example, an algorithm or other means may be used to identify a region of the feature space or clusters or groupings of feature vectors in the N-dimensional feature space that frequently precede an ictal state by a predetermined period of time but occur infrequently in inter-ictal intervals. Alternatively, a prior art seizure prediction algorithm may be used.

Figure 1B:
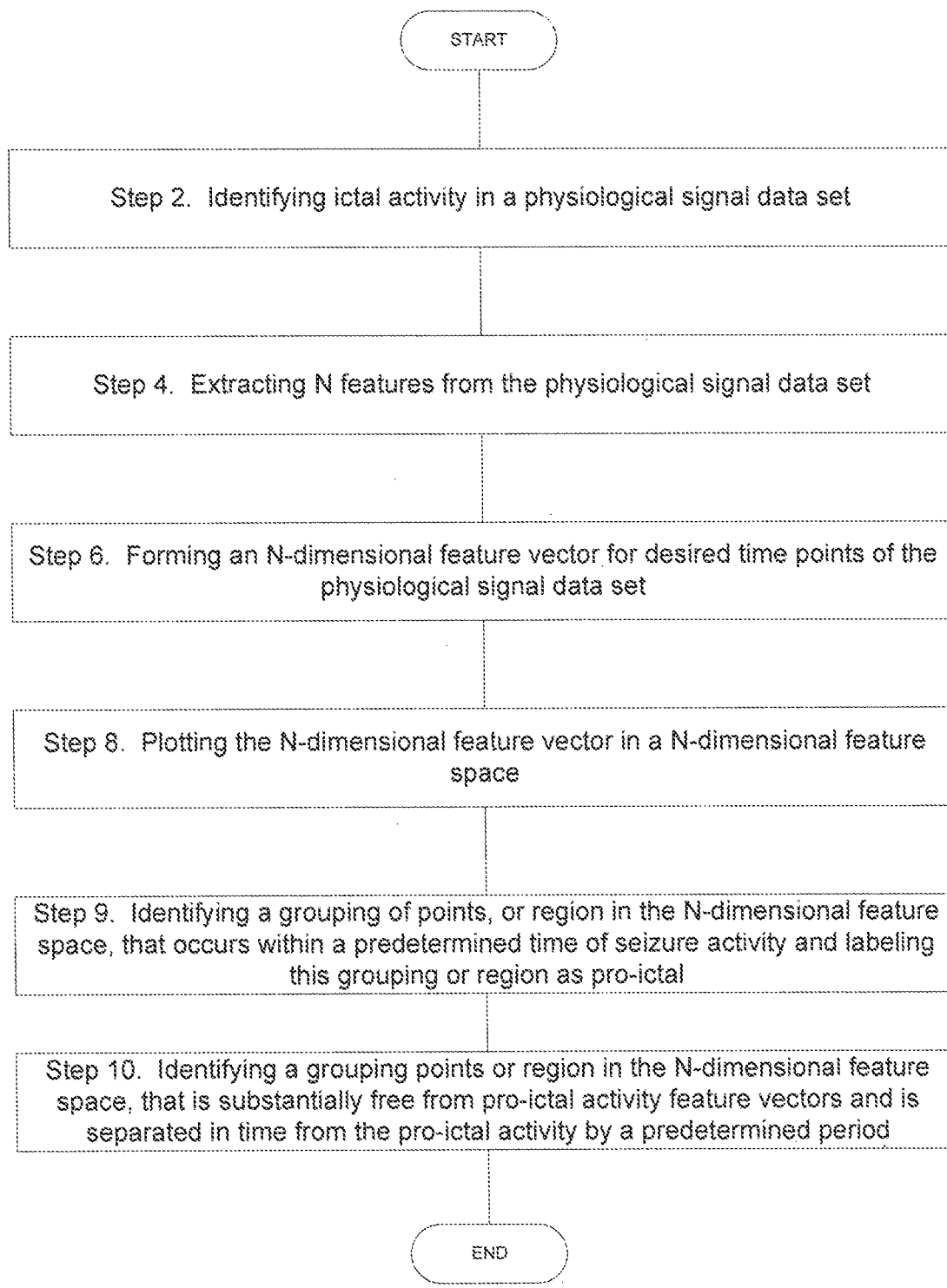
FIG. 1B is a simplified method of identifying a contra-ictal condition in a subject data set according to another embodiment of the invention.

FIG. 1B shows another embodiment of a method of identifying a contra-ictal state for a subject. This method tracks the method of FIG. 1A for steps 2, 4, 6 and 8. FIG. 1B adds a step 9, however, that involves identifying a grouping of points or a region in the N-dimensional feature space that occurs within a predetermined time of seizure activity. This group or region is labeled "pro-ictal." In step 10 of this method, the method then identifies a grouping of points or a region in the N-dimensional feature space that is substantially free from pro-ictal activity feature vectors and is separated in time from the pro-ictal activity by a predetermined time period using, e.g., the techniques discussed above with respect to step 10 of FIG. 1A.

Figure 1C:
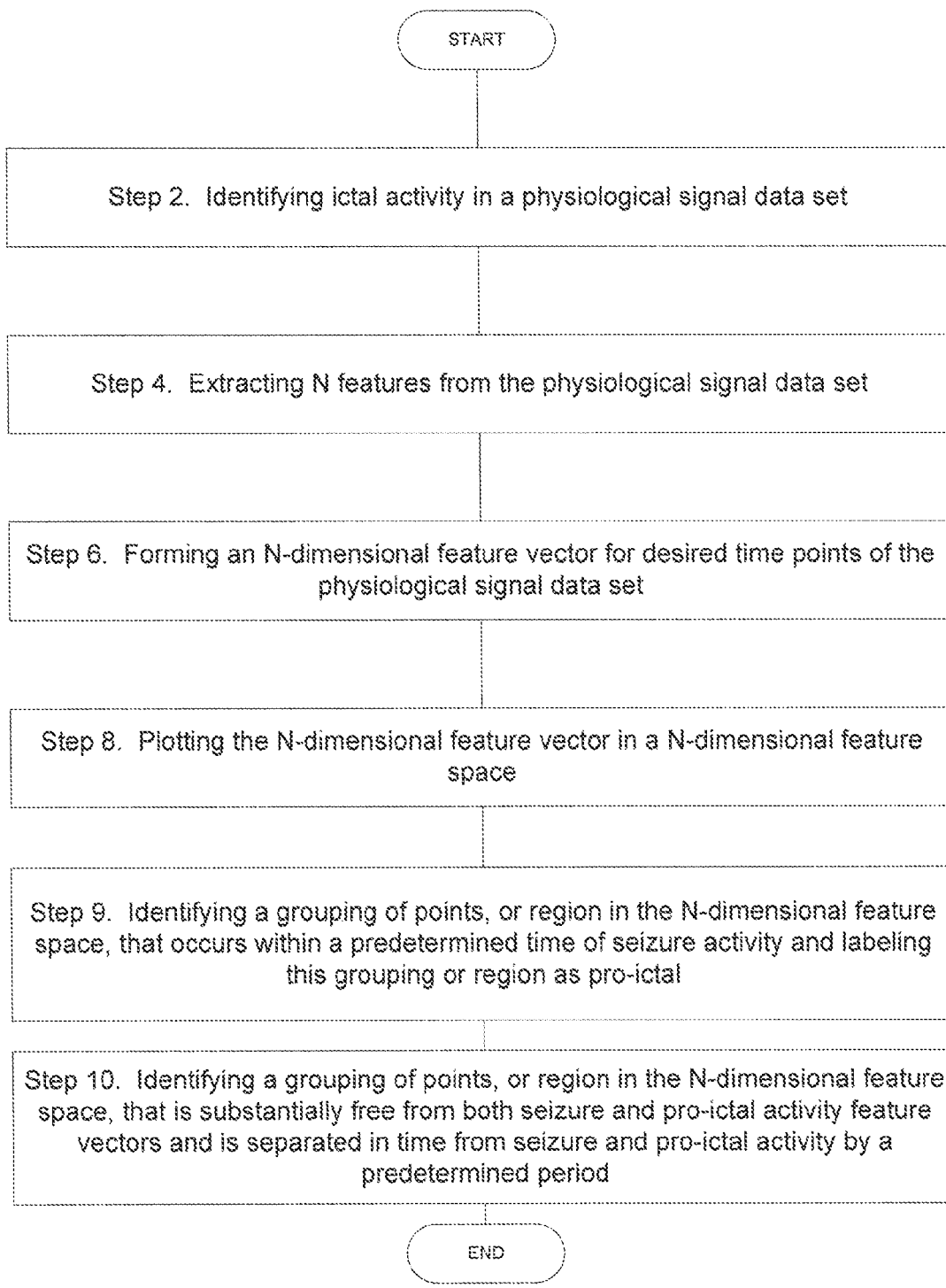
FIG. 1C is a simplified method of identifying a contra-ictal condition in a subject data set according to yet another embodiment of the invention.

FIG. 1C shows yet another embodiment of a method of identifying a contra-ictal state for a subject. Once again, this method tracks the method of FIG. 1A for steps 2, 4, 6 and 8. Like the method of FIG. 1B, FIG. 1C adds a step 9 that involves identifying a grouping of points or a region in the N-dimensional feature space that occurs within a predetermined time of seizure activity. This group or region is labeled "pro-ictal." In step 10 of this method, the method then identifies a grouping of points or a region in the N-dimensional feature space that is substantially free from both pro-ictal activity feature vectors and seizure feature vectors, and is separated in time from the seizure and pro-ictal activity by a predetermined time period using, e.g., the techniques discussed above with respect to step 10 of FIG. 1A.

Figure 2:
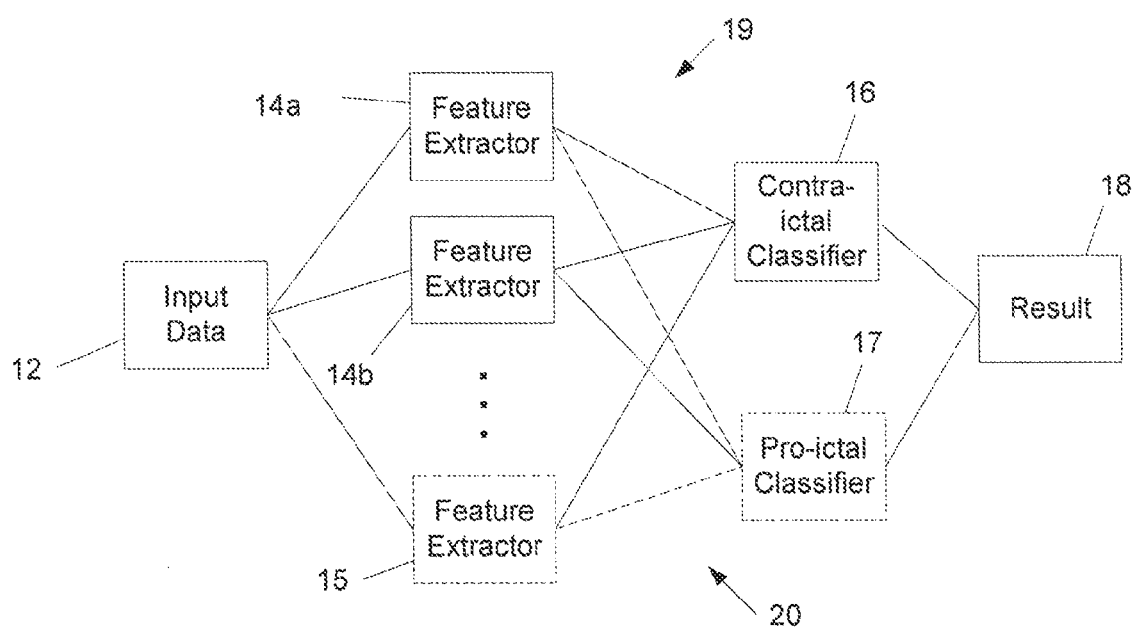
FIG. 2 schematically illustrates a plurality of algorithms that may be embodied by the present invention.

Once the algorithm has been trained to identify the different classes for the subject, the algorithm may be embodied or otherwise uploaded into a subject system for performing substantially real-time monitoring and assessment of the subject's brain activity. FIG. 2 depicts an example of the overall structure of a system for performing substantially real-time assessment of the subject's brain activity and for determining the communication output that is provided to the subject. The system may comprise one or more algorithms or modules that process input data 12. The algorithms may take a variety of different forms, but typically comprises one or more feature extractors 14a, 14b, 15 and at least one classifier 16, 17. The embodiment illustrated in FIG. 2 shows a contra-ictal algorithm 19 and a pro-ictal algorithm 20 which share at least some of the same feature extractors 14a, 14b. In alternative embodiments, however, the algorithms used in the system may use exactly the same feature extractors or completely different feature extractors (not shown).

The input data 12 is typically EEG, but may comprise representations of physiological signals obtained from monitoring a subject and may comprise any one or combination of the aforementioned physiological signals from the subject. The input data may be in the form of analog signal data or digital signal data that has been converted by way of an analog to digital converter (not shown). The signals may also be amplified, preprocessed, and/or conditioned to filter out spurious signals or noise. For purposes of simplicity the input data of all of the preceding forms is referred to herein as input data 12. In one preferred embodiment, the input data comprises between about 1 channel and about 64 channels of EEG from the subject.

The input data 12 from the selected physiological signals is supplied to the one or more feature extractors 14a, 14b, 15. Feature extractor 14a, 14b, 15 may be, for example, a set of computer executable instructions stored on a computer readable medium, or a corresponding instantiated object or process that executes on a computing device. Certain feature extractors may also be implemented as programmable logic or in a fixed logic device. In general, feature extractors 14a, 14b, 15 can process data 12 and identify some characteristic of interest in the data 12. Feature extractors used in the subject system are typically the same feature extractors used in the method described in the method of FIG. 1. Such a characteristic of the data is referred to herein as an extracted feature.

Each feature extractor 14a, 14b, 15 may be univariate (operating on a single input data channel), bivariate (operating on two data channels), or multivariate (operating on multiple data channels). Some examples of potentially useful characteristics to extract from signals for use in determining the subject's propensity for a neurological event include but are not limited to bandwidth limited power (alpha band [8-13 Hz], beta band [13-18 Hz], delta band [0.1-4 Hz], theta band [4-8 Hz], low beta band [12-15 Hz], mid-beta band [15-18 Hz], high beta band [18-30 Hz], gamma band [30-48 Hz], high frequency power [>48 Hz], bands with octave or half-octave spacings, wavelets, etc.), second, third and fourth (and higher) statistical moments of the EEG amplitudes or other features, spectral edge frequency, decorrelation time, Hjorth mobility (HM), Hjorth complexity (HC), the largest Lyapunov exponent L(max), effective correlation dimension, local flow, entropy, loss of recurrence LR as a measure of non-stationarity, mean phase coherence, conditional probability, brain dynamics (synchronization or desynchronization of neural activity, STL-max, T-index, angular frequency, and entropy), line length calculations, first, second and higher derivatives of amplitude or other features, integrals, and mathematical linear and non-linear operations including but not limited to addition, subtraction, division, multiplication and logarithmic operations. Of course, for other neurological conditions, additional or alternative characteristic extractors may be used with the systems described herein.

The extracted characteristics can be supplied to the one or more classifiers 16, 17. Like the feature extractors 14a, 14b, 15, each classifier 16, 17 may be, for example, a set of computer executable instructions stored on a computer readable medium or a corresponding instantiated object or process that executes on a computing device. Certain classifiers may also be implemented as programmable logic or in a fixed logic device.

The classifiers 16, 17 analyze one or more of the extracted characteristics, and either alone or in combination with each other (and possibly other subject dependent parameters), provide a result 18 that may characterize, for example, a subject's condition. The output from the classifiers may then be used to determine the output communication that is provided to the subject regarding their condition. As described above, the classifiers 16, 17 are trained by exposing them to training measurement vectors, typically using supervised methods for known classes, e.g. ictal, and unsupervised methods as described above for classes that can't be identified a priori, e.g. contra-ictal. Some examples of classifiers include k-nearest neighbor ("KNN"), binary and higher order space partitions, linear or non-linear regression, Bayesian, mixture models based on Gaussians or other basis functions, neural networks, and support vector machines ("SVM"). Each classifier 16, 17 may provide a variety of output results, such as a logical result or a weighted result. The classifiers 16, 17 may be customized for the individual subject and may be adapted to use only a subset of the characteristics that are most useful for the specific subject. Additionally, over time, the classifiers 16, 17 may be further adapted to the subject, based, for example, in part on the result of previous analyses and may reselect extracted characteristics that are used for the specific subject.

For the embodiment of FIG. 2, the pro-ictal classifier 17 may classify the outputs from feature extractors 14a, 14b to detect characteristics that indicate that the subject is at an elevated susceptibility for a neurological event, while the contra-ictal classifier 16 may classify the outputs from feature extractors 14a, 14b, 15 to detect characteristics that occur when the subject is unlikely to transition into an ictal condition for a specified period of time. The combined output of the classifiers 16, 17 may be used to determine the output communication provided to the subject. In embodiments which comprise only the contra-ictal algorithm, the output from the contra-ictal classifier 16 alone may be used to determine the output communication to the subject.

Figure 3:
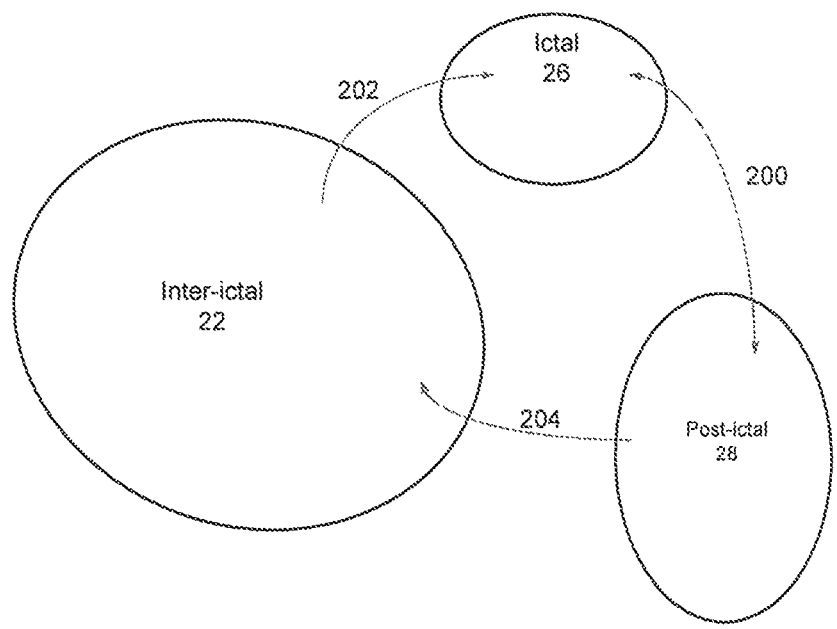
FIG. 3 is a diagram illustrating three neurological states of epilepsy (ictal, post-ictal and inter-ictal).

FIG. 3 illustrates a Venn diagram illustrating a simplified approximation of the relationship of the neurological states or conditions of subjects diagnosed with epilepsy. The ictal state 26 is the actual period in which the subject is experiencing a seizure. As previously mentioned, the "average" subject is in the ictal state approximately 0.02% of the overall time. Therefore, the associated sizes of the Venn diagram set areas are not meant to be representative of the overall time the subject is in the various states, otherwise, the ictal period would be approximately 5,000 times smaller than the inter-ictal period. The inter-ictal state 22 is sometimes termed the "normal" neurological state and represents the neurological state between seizures. The post-ictal state 28 is the neurological state immediately following a seizure or ictal 26 state. Also depicted in this three state model are the transitions. During the onset of a seizure the neurological state transitions 202 from the inter-ictal state to the ictal state. Upon termination of the seizure the neurological state transitions 200 to the post-ictal state and then transitions 204 to the inter-ictal state. During seizure clustering it is also possible for the subject to transition 200 from the post-ictal state to the ictal state.

Figure 4:
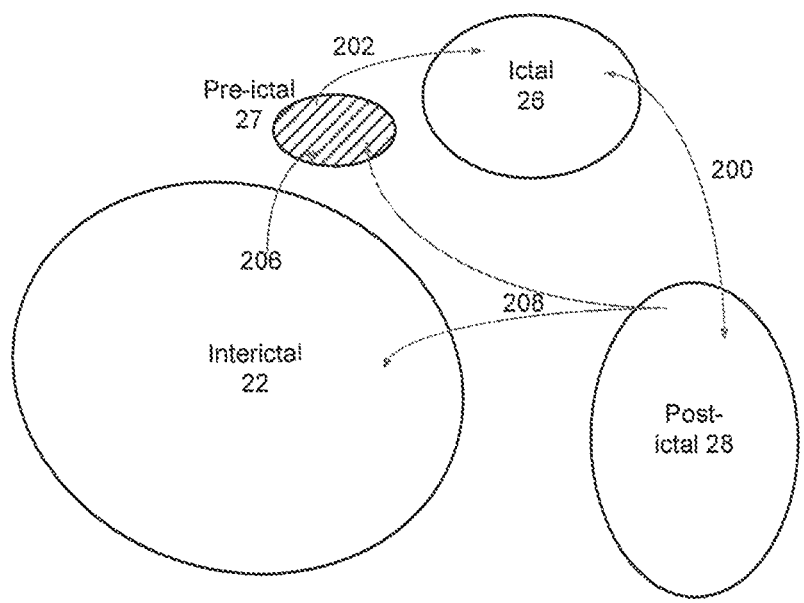
FIG. 4 is a diagram illustrating the three neurological states as well as a pre-ictal period.

FIG. 4 illustrates an additional state, pre-ictal 27, which occurs between the inter-ictal state and the seizure or ictal state. Some researchers have proposed that seizures develop minutes to hours before the clinical onset of the seizure. These researchers therefore classify the "pre-ictal" condition as the beginning of the ictal or seizure event which begins with a cascade of events. Under this definition, a seizure is imminent and will occur (e.g. transition 203 from pre-ictal to ictal) if a pre-ictal condition is observed. There have been a number of proposals from groups around the world for predicting seizures and warning the subject of the impending seizure. Most of such proposals attempt to analyze the subject's electroencephalogram or electrocorticograms (referred to collectively as "EEGs"), to differentiate between a "pre-ictal condition" (i.e., pre-seizure condition) and an "inter-ictal condition" (i.e., between seizures). To date, however, none of the proposed systems have proven to be effective in predicting seizures. With this additional state in the state diagram of FIG. 4, we see that it is possible to transition from the post-ictal state either to pre-ictal, inter-ictal or ictal.

Figure 5:
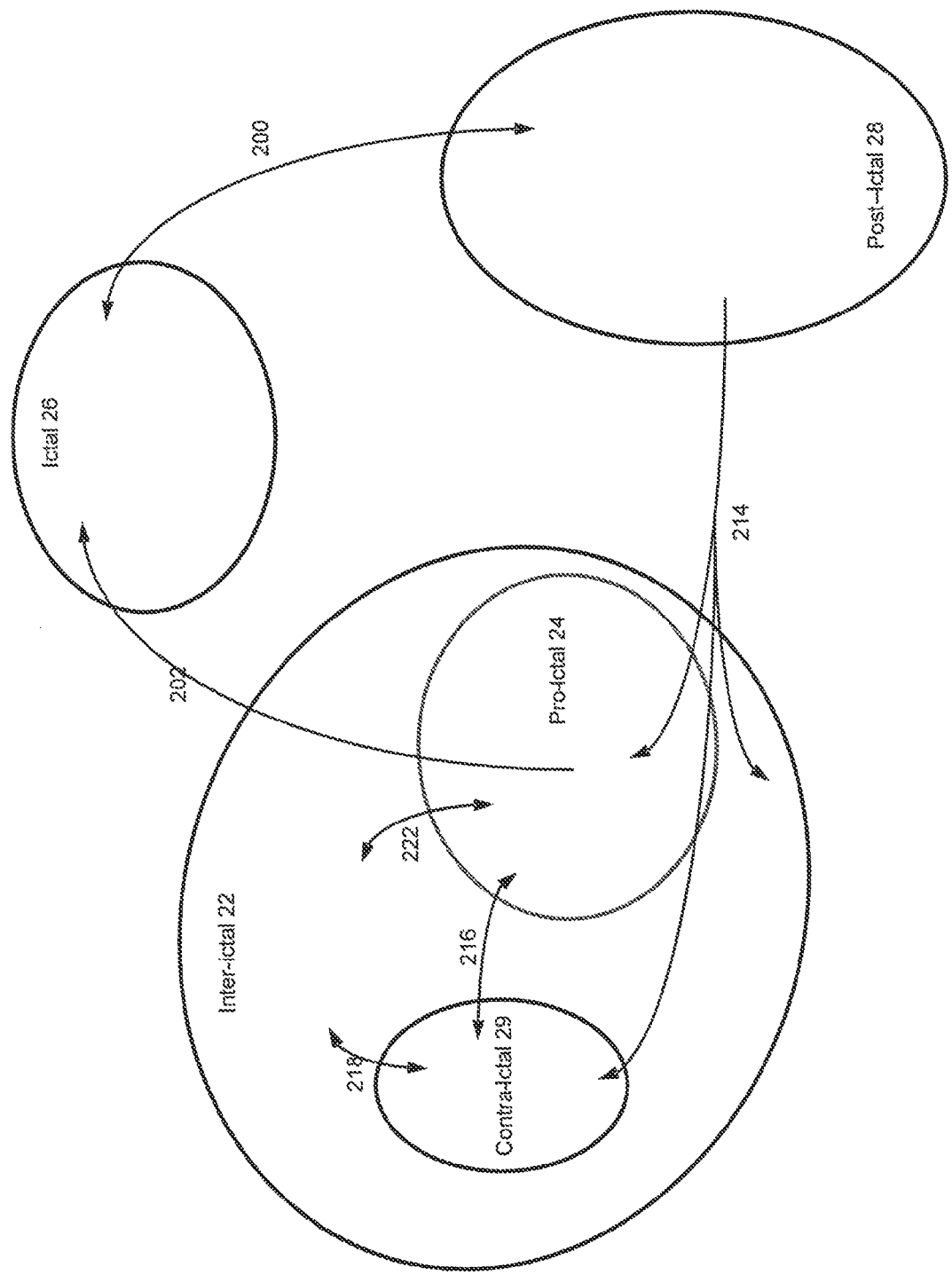
FIG. 5 is a diagram illustrating the three neurological states as well as contra-ictal and pro-ictal states.

FIG. 5 illustrates two additional neurological states. These states, contra-ictal and pro-ictal, are shown as subsets within the inter-ictal state. The contra-ictal state 29 is referred to as a "low susceptibility to seizure" condition for a time period. The pro-ictal state 24 represents a neurological state having a high susceptibility for a seizure. As shown it is possible for the neurological contra-ictal state to transition back into the general inter-ictal state (transition 218) or into a pro-ictal state (transition 216). As shown by transitions 216, 222 and 202, it is possible for the neurological pro-ictal state to transition to the contra-ictal state, the inter-ictal state or the ictal state. The subject may also go from an inter-ictal state to an ictal state.

Figure 6:
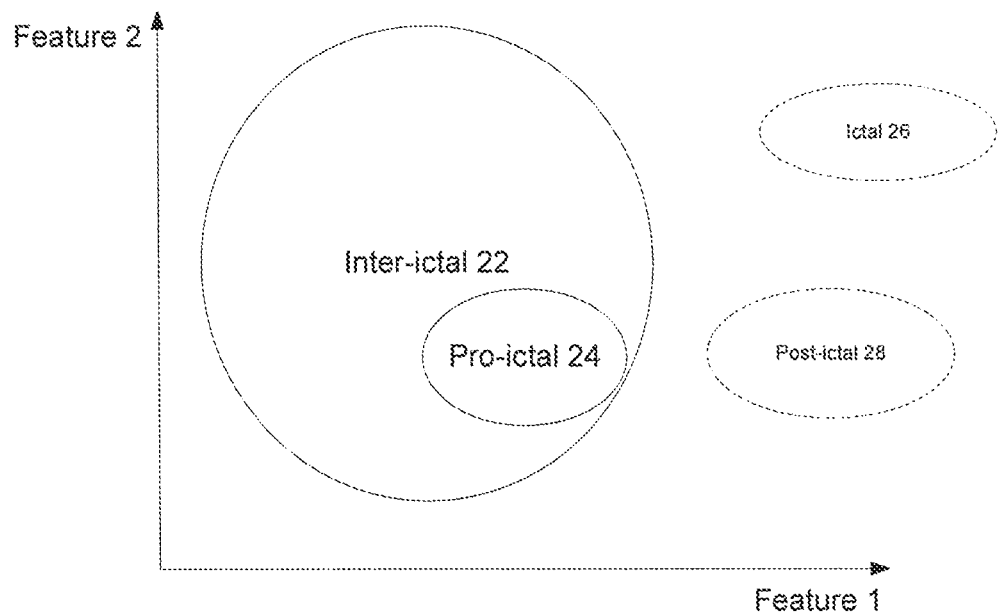
FIG. 6 illustrates one example of a classification method in 2D feature space.

FIGS. 6-12 illustrate different aspects of the systems encompassed by the present invention. The classifiers may have multiple classes (e.g., two or more), may provide a weighted answer, or they may provide an output that is expressed as a continuum between the contra-ictal and pro-ictal conditions, with a scalar or vector of parameters describing the actual condition and its variations. For example, as shown in FIG. 6, a multiple class classifier may have labels such as 'inter-ictal' 22, 'pro-ictal' 24, 'ictal' 26, or 'post-ictal' 28. In other embodiments shown in FIG. 11, the classifiers 16, 17 are one-class classifiers that calculate probability of class membership (probability of pro-ictal, probability of contra-ictal).

Figure 7:
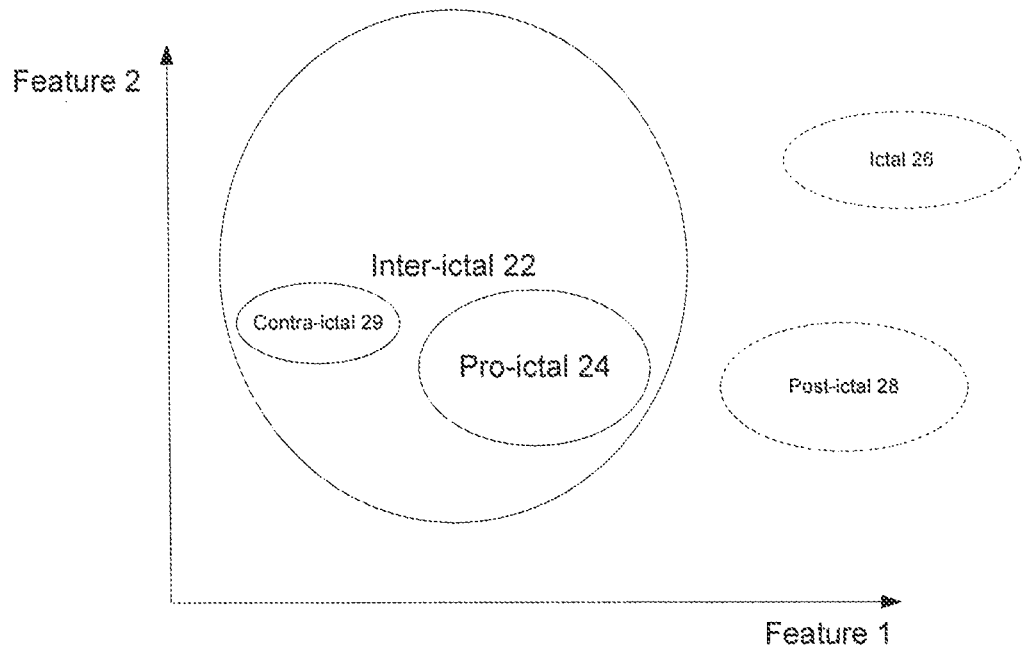
FIGS. 7 and 8 illustrate various classification methods encompassed by the present invention which include a contra-ictal class in 2D feature space.
Figure 8:
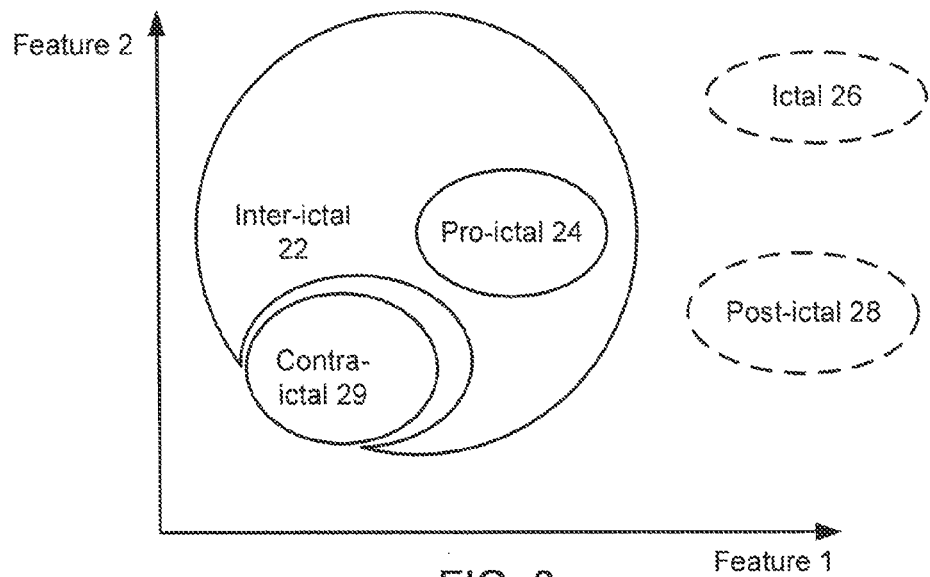

Referring now to FIGS. 7 and 8, as they relate to the seizure advisory system, one implementation of a classification of conditions defined by the classifiers 16, 17 includes (1) an inter-ictal class 22 (sometimes referred to as a "normal" condition), (2) a pro-ictal class 24 (sometimes referred to as an "abnormal" or "high-susceptibility to seizure" condition), (3) an ictal class 26 (sometimes referred to as a "seizure" condition), (4) a post-ictal class 28 (sometimes referred to as a "post-seizure" condition), and (5) a contra-ictal condition 29 (sometimes referred to as a "low susceptibility to seizure for a time period" condition). FIG. 7 illustrates the contra-ictal class 29 as a sub-set of the inter-ictal class 28 while FIG. 8 illustrates the contra-ictal class 29 as a separate class from the inter-ictal class 28.

Figure 9:
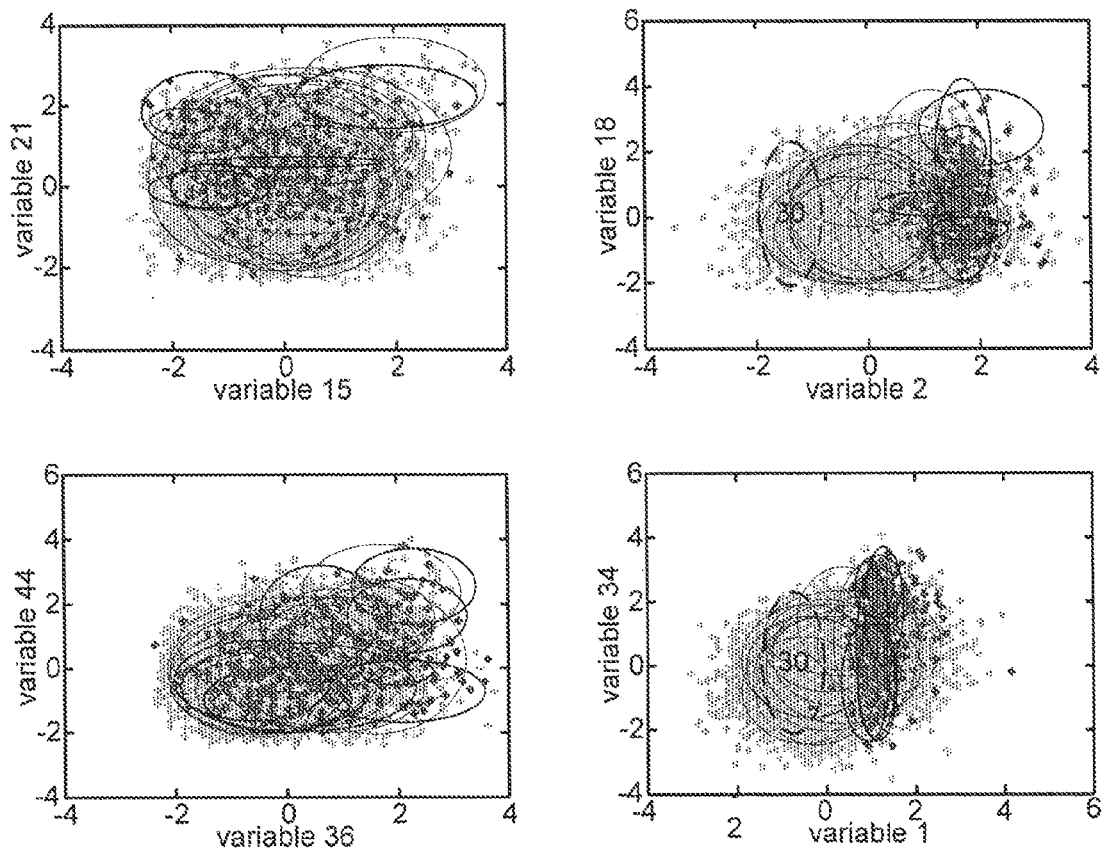
FIG. 9 illustrates a plotting of two-dimensional feature vectors in a two-dimensional feature space with different combination of variables (features).

FIG. 9 illustrates an example of 2-dimensional projections of an N-dimensional feature space extracted from subject physiological data, such as EEG data. The dark data points are feature vectors that occur within 20 minutes of a subsequent seizure. These data points are therefore labeled pro-ictal. The lighter points are inter-ictal feature vectors that occur more than 3 hours prior to a seizure. As shown in the projection onto variables 15 and 21 and variables 36 and 44 in the left column of FIG. 9, there does not appear to be any differentiable clusters or groupings between the two groups. However, for the projection onto variable 2 and 18 and variable 1 and 34 in the right column of FIG. 9, there is a more defined separation between the two classes. While the pro-ictal class is included in the inter-ictal class, there are areas outlined by the dotted lines 30 in both two-dimensional projections that are substantially free of pro-ictal feature vectors.

Figure 10:
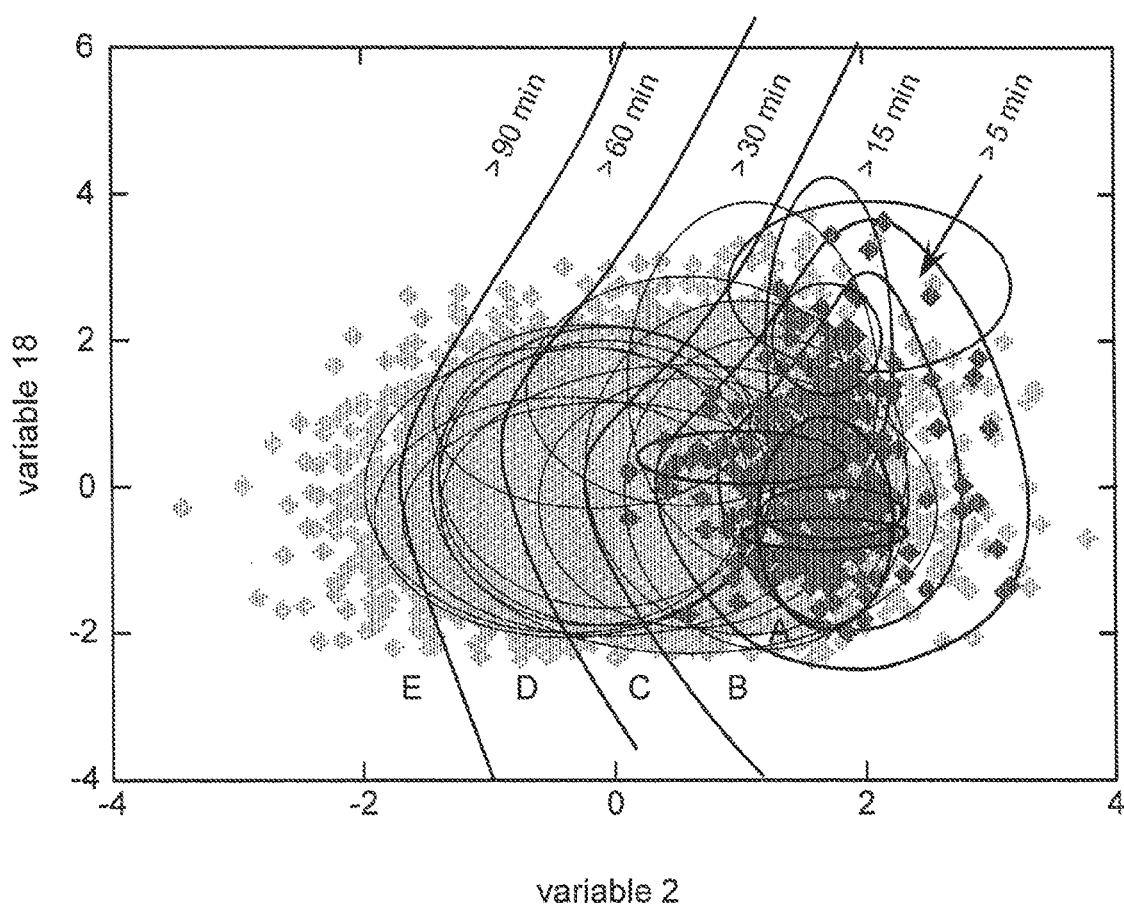
FIG. 10 illustrates a plotting of two-dimensional feature vectors in a two dimensional feature space with contours indicating minimum time to seizure.

The feature classification approach of FIG. 9 can be adapted to develop contra-ictal state detection algorithms for predetermined time periods of other lengths during which a seizure is unlikely. FIG. 10 illustrates one of the 2-dimensional projections of an N-dimensional features space of FIG. 9 for variable 2 versus 18. Added to this 2D projection are contour lines regarding the time elapsed prior to a seizure. For the area marked by "A" all the feature vectors occur more than 5 minutes prior to a seizure. For the area marked by "B" all the feature vectors occur more than 15 minutes prior to the seizure. For areas marked by "C", "D", "E" all of the feature vectors occur more than 30, 60 and 90 minutes prior to the seizure, respectively. Using this 2-dimensional projection one may also adjust/customize the green light for indicating the "contra-ictal" state by selecting the time to seizure contour line (e.g. 15, 30, 60, 90, etc.).

Figures 11, 12:
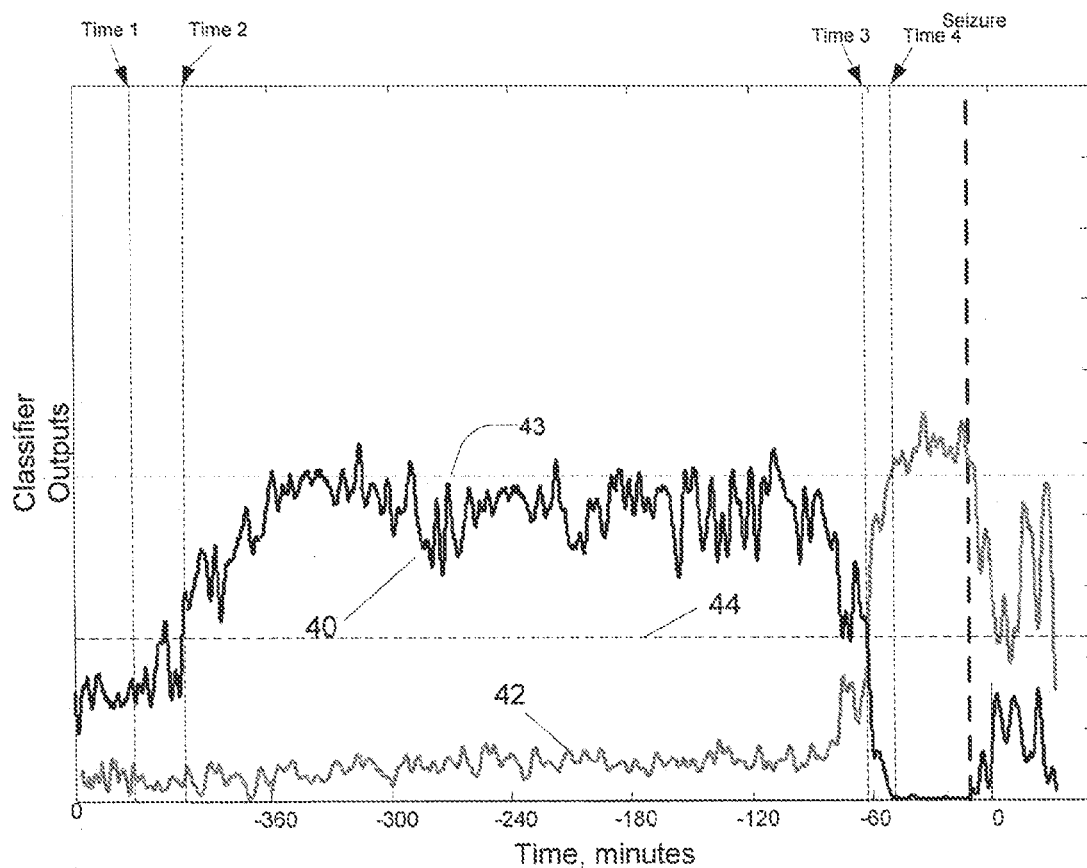
FIG. 11 is an overlay of an output from a contra-ictal classifier over an output of a pro-ictal classifier.
FIG. 12 is a sample truth chart that may be used to determine a communication output provided to the subject.

After deriving the feature vectors that may be used to classify subject physiological signals as being contra-ictal, pro-ictal, etc., these feature vectors may be used to train or form an algorithm for use in a patient monitoring device. FIGS. 11 and 12 illustrate how the outputs from two one-state classifiers within a trained analysis algorithm in a patient monitoring device may be used to determine the output communication provided to the subject. FIG. 11 illustrates an example of the output from the contra-ictal classifier 40 overlaid on an output from the pro-ictal classifier 42. Unlike prior art seizure monitoring devices that looked only for features corresponding to ictal or pre-ictal activity, these classifiers classify extracted features against earlier-derived features to determine whether the extracted features correspond to pro-ictal activity and whether the extracted features correspond to contra-ictal activity. The right-most dotted line indicates where the seizure started. FIG. 12 is a truth table 50 that processes the outputs from the classifiers to determine the output communication provided to the subject.

The truth table 50 of FIG. 12 shows the different possible combinations of outputs from the each of the classifiers and the associated output communication provided to the subject. In one simplified embodiment, the potential output to the subject includes a green light, a yellow light and a red light. A green light may indicate to the subject that they are at a low susceptibility to a seizure for a time period. A yellow light (or some other indication) may indicate to the subject to proceed with caution. Such an indication does not necessarily mean that the subject is at a high susceptibility to have a seizure, but it does mean that it is possible to have a seizure within a predetermined time (such as 90 minutes, etc.). Finally, a red light (or some other indication) may indicate to the subject that they are at an elevated susceptibility for a seizure.

It should be appreciated however, that while FIGS. 11 and 12 describe providing an output to the subject in the form of yellow lights, green lights and red lights, the present invention embodies any number of different type of outputs may be provided to the subject to indicate their condition. The subject's condition could, alternatively, be indicated by the absence of an output. For example, the system could comprise a yellow light and a red light, and the lack of either the red light or yellow light being illuminated would indicate the subject is in a contra-ictal state. The outputs may be different displays on a screen to the subject, different tactile outputs (e.g., vibrations), different sounds, different lights, or any combination thereof. Additionally, such outputs are not limited to the patient/subject, rather the output may be provided to a caregiver. Caregivers may include a physician, nurse or relative, or the like. Furthermore, such output may also provide the inputs to either a closed loop or open loop therapeutic response which attempts to minimize and/or prevent a seizure occurrence. Such therapeutic approaches may include, without limitation, vagus nerve stimulation, deep brain stimulation, neurostimulation, automated/semi-automated or manual dispensing of antiepileptic drugs, and biofeedback techniques.

Referring again to FIG. 11, at Time 1, both classifier outputs 40, 42 are considered to be below an artificially specified threshold 44 and are both considered to be "low." In this embodiment, anything below the threshold 44 indicates that there is a low likelihood that the subject is in a pro-ictal state and/or a low likelihood that the subject is in a contra-ictal state. Since such outputs 40, 42 from the classifiers are inconclusive and appear to conflict with each other, the output communication provided to the subject may indicate that that the subject should proceed with caution. One example of such an output communication is a yellow light. This output corresponds to the first row 52 of the truth table 50 of FIG. 12.

At Time 2, the output 40 from the contra-ictal classifier is high (H) and the output from the pro-ictal classifier 42 is low (L). Such a classification indicates that there is a low likelihood that the subject has an increased susceptibility for a seizure and a high likelihood of being in a contra-ictal state. These classifiers appear to be consistent with each other; consequently, the output communication provided to the subject may indicate that the subject is in a contra-ictal state. One example of such an output communication is the display of a green light. This scenario corresponds to the second row 54 of FIG. 12.

As shown in FIG. 11, the green light would stay on until Time 3 where the output 40 from the contra-ictal classifier is trending lower but is still above threshold 44 (is high (H)) and the output 42 from the pro-ictal classifiers transitions to high (H). As shown in the third row 56 of the truth table of FIG. 12, when both classifier outputs are high (H)—which indicates a high likelihood that the subject is at an increased susceptibility to a seizure and a high likelihood that the subject is in a contra-ictal condition (inconsistent outputs)—an output communication is output to the patent to indicate that they should proceed with caution (e.g., yellow light).

Finally, at Time 4 in FIG. 11, the output 40 from the contra-ictal classifier has fully transitioned to low (L) (e.g., low likelihood that the subject is in a contra-ictal state) and the output 42 from the pro-ictal classifier is above threshold 44 and is high (H) (e.g., high likelihood that the subject is at an increased susceptibility to a seizure). This scenario corresponds with the fourth row 58 of FIG. 12 and the red light would be output to the subject—which indicates that the subject has a high susceptibility to a seizure and should take an appropriate action.

In another embodiment shown in FIG. 11, different thresholds are used for the contra-ictal and pro-ictal classifiers. For example, the contra-ictal classifier output 40 could be compared to a higher threshold 43, while the pro-ictal classifier output 42 could be compared to the lower threshold 44. In this example, the contra-ictal indication (e.g., green light) might be provided if the contra-ictal classifier output 40 exceeds the threshold 43 and if the pro-ictal classifier output 42 does not exceed the threshold 44; the pro-ictal indication (e.g., red light) might be provided if the contra-ictal classifier output 40 does not exceed threshold 43 and if the pro-ictal classifier output 42 exceeds threshold 44; and an indication that the outputs are inconclusive (e.g., a yellow light) if neither classifier output exceeds its threshold.

While FIGS. 11 and 12 illustrate the use of two one-class classifiers, any number and type of classifier may be used by the systems of the present invention. For example, in other embodiments it may be desirable to have a single classifier classify the subject as being in one of three conditions—an inter-ictal class, a pro-ictal class, and a contra-ictal class—which could correspond, respectively, to a normal propensity for a future seizure, an elevated or high propensity for a future seizure, and a low propensity for a future seizure.

In other embodiments, the output of the classification algorithm would indicate the existence of a contra-ictal condition (e.g., a green light) so long as the extracted feature vector corresponds only with training points that almost never preceded a seizure by less than the predetermined time period, such as 90 minutes. The output of the classification algorithm would indicate the existence of a pro-ictal condition (e.g., a red light) if the extracted feature corresponds to a region of the feature space indicative of pro-ictal state. This indication is not a seizure prediction; a pro-ictal condition might resolve without a seizure ever occurring. The end of a contra-ictal indication does indicate, however, that it is no longer unlikely that a seizure will occur within 90 minutes (or other predetermined time). In addition, in these embodiments, while the contra-ictal indication has a predetermined time associate with it, the pro-ictal indication does not. The subject may stay in a pro-ictal state for a prolonged period of time, or the subject might leave the pro-ictal state immediately after entering it.

In still other embodiments, the classification algorithm for a contra-ictal indication can be derived by determining the kinds of feature vectors that never preceded a pro-ictal condition by less than a predetermined time. When trained using this kind of subject data, this contra-ictal classification algorithm would indicate a contra-ictal condition (such as be lighting a green light) when a feature vector extracted from a subject's physiological signal (such as an EEG) corresponds to one of such feature vectors, thereby indicating that the subject is unlikely to transition to a pro-ictal state within that predetermined time period.

In yet other embodiments, the contra-ictal indication classification algorithm can be derived by determining the kinds of feature vectors that never preceded a pro-ictal condition by less than a predetermined time and never preceded a seizure by less than the predetermined time. When trained using this kind of subject data, this contra-ictal classification algorithm would indicate a contra-ictal condition (such as be lighting a green light) when a feature vector extracted from a subject's physiological signal (such as an EEG) corresponds to one of such feature vectors, thereby indicating that the subject is unlikely to transition to either a pro-ictal state or to a seizure within that predetermined time period.

Figure 13:
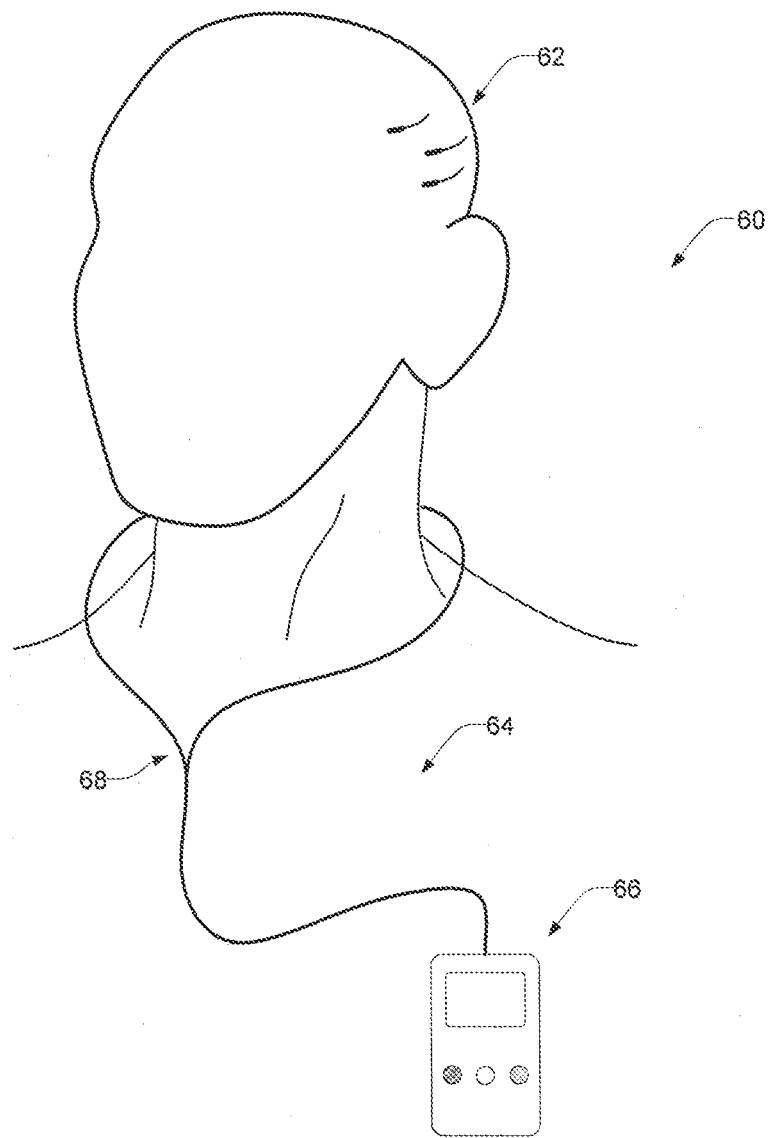
FIG. 13 illustrates a simplified system embodied by the present invention which comprises one or more implantable devices in communication with an external device.

FIG. 13 illustrates one example of a system in which the algorithms 19, 20 (FIG. 2) of the present invention may be embodied. System 60 includes one or more implantable devices 62 that are configured to sample electrical activity from the subject's brain (e.g., EEG signals). Suitable systems including minimally-invasive implantable devices are described in commonly-owned U.S. patent application Ser. No. 11/766,742, filed Jun. 21, 2007, to Harris et al., the complete disclosure of which is incorporated herein by reference. The implantable devices 62 may be active (with internal power source), passive (no internal power source), or semi-passive (internal power source to power components, but not to transmit data signal). The implantable devices 62 may be implanted anywhere in the subject, but typically one or more of the devices 62 may be implanted adjacent a previously identified epileptic focus or a portion of the brain where the focus is believed to be located. It may also be desirable to position one or more of the implantable devices distal to the epileptic focus. The system 60 is used to monitor a neurological condition of subject 62 for purposes of estimating a subject's susceptibility for a neurological event. The system 60 of the illustrated embodiment provides for substantially continuous sampling and analysis of brain wave electrical signals. Alternatively, the devices 62 themselves may be used to help determine the location of the epileptic focus.

The physician may implant any desired number of devices in the subject. In some embodiments between about 1 and about 32 channels are provided, and preferably between about 8 and about 16 channels are provided. As noted above, in addition to monitoring brain signals, one or more additional implanted devices 62 may be implanted to measure other physiological signals from the subject.

While it may be possible to implant the implantable devices 62 under the skull and in or on the brain, it is preferred to implant the implantable devices 62 in a minimally invasive fashion under at least one layer of the subject's scalp and above the skull. Implantable devices 62 may be implanted between any of the layers of the scalp (sometimes referred to herein as "sub-galeal"). For example, the implantable devices may be positioned between the skin and the connective tissue, between the connective tissue and the epicranial aponeurosis/galea aponeurotica, between the epicranial aponeurosis/galea aponeurotica and the loose areolar tissue, between the loose areolar tissue and the pericranium, and/or between the pericranium and the calvarium. In some configurations, it may be useful to implant different implantable devices 62 between different layers of the scalp.

Implantable devices 62 will typically be configured to substantially continuously sample the brain activity of the groups of neurons in the immediate vicinity of the implanted device. In some embodiments, if placed below the skull and in contact with the cortical surface of the brain, the electrodes may be sized to be able to sample activity of a single neuron in the immediate vicinity of the electrode (e.g., a microelectrode). Typically, the implantable device 62 will be interrogated and powered by a signal from the external device to facilitate the substantially continuous sampling of the brain activity signals. Sampling of the brain activity is typically carried out at a rate above about 200 Hz, and preferably between about 200 Hz and about 1000 Hz, and most preferably at about 400 Hz, but it could be higher or lower, depending on the specific condition being monitored, the subject, and other factors. Each sample of the subject's brain activity will typically contain between about 8 bits per sample and about 32 bits per sample, and preferably between about 12 bits per sample and about 16 bits per sample. Thus, if each return communication transmission to the external device includes one EEG sample per transmission, and the sample rate is 400 Hz and there are 16 bits/sample, the data transfer rate from the implantable devices 62 to the external device 64 is at least about 6.4 Kbits/second. If there are 32 implantable devices, the total data transfer rate for the system 60 would be about 205 Kbits/second. In alternative embodiments, it may be desirable to have the implantable devices sample the brain activity of the subject in a non-continuous basis. In such embodiments, the implantable devices 62 may be configured to sample the brain activity signals periodically (e.g., once every 10 seconds) or aperiodically.

Implantable device 62 may comprise a separate memory module for storing the recorded brain activity signals, a unique identification code for the device, algorithms, other programming, or the like.

A subject instrumented with the implanted devices 62 will typically carry a data collection device 64 that is external to the subject's body. The external device 64 would receive and store the signal from the implanted device 62 with the encoded EEG data (or other physiological signals). The external device is typically of a size so as to be portable and carried by the subject in a pocket or bag that is maintained in close proximity to the subject. In alternative embodiments, the device may be configured to be used in a hospital setting and placed alongside a subject's bed. Communication between the data collection device 64 and the implantable device 62 typically takes place through wireless communication. The wireless communication link between implantable device 62 and external device 64 may provide a communication link for transmitting data and/or power. External device 64 may include a control module 66 that communicates with the implanted device through an antenna 68. In the illustrated embodiment, antenna 68 is in the form of a necklace that is in communication range with the implantable devices 62. It should be appreciated however, that the configuration of antenna 68 and control module 66 may be in a variety of other conventional or proprietary forms. For example, in another embodiment control module 66 may be attached around an arm or belt of the subject, integrated into a hat, integrated into a chair or pillow, and/or the antenna may be integrated into control module 66.

In order to facilitate the transmission of power and data, the antenna of the external device and the implantable devices must be in communication range of each other. The frequency used for the wireless communication link has a direct bearing on the communication range. Typically, the communication range is between at least one foot, preferably between about one foot and about twenty feet, and more preferably between about six feet and sixteen feet. As can be appreciated, however, the present invention is not limited to such communication ranges, and larger or smaller communication ranges may be used. For example, if an inductive communication link is used, the communication range will be smaller than the aforementioned range.

In some situations, it may be desirable to have a wire directly connecting the subject-worn data collection device 64 to an interface (not shown) that could directly link up to the implanted devices 62 that are positioned below the subject's skin. For example, the interface may take the form of a magnetically attached transducer, as with cochlear implants. This could enable power to be continuously delivered to the implanted devices 62 and provide for higher rates of data transmission.

In some configurations, system 60 may include one or more intermediate transponders (not shown) that facilitates data transmission and power transmission between implantable device 62 and external device 64. The intermediate transponder may be implanted in the subject or it may be external to the subject. If implanted, the intermediate transponder will typically be implanted between the implantable device 62 and the expected position of the external device 64 (e.g., in the neck, chest, or head). If external, the transponder may be attached to the subject's skin, positioned on the subject's clothing or other body-worn assembly (e.g., eyeglasses, cellular phone, belt, hat, etc.) or in a device that is positioned adjacent the subject (e.g., a pillow, chair headrest, etc.). The intermediate transponder may be configured to only transmit power, only transmit data, or it may be configured to transmit both data and power. By having such intermediate transponders, the external device 64 may be placed outside of its normal communication range from the implanted devices 62 (e.g., on a subject's belt or in a subject's bag), and still be able to substantially continuously receive data from the implantable device 62 and/or transmit power to the implantable device 62.

Transmission of data and power between implantable device 62 and external device 64 is typically carried out through a radiofrequency link, but may also be carried out through magnetic induction, electromagnetic link, Bluetooth® link, Zigbee link, sonic link, optical link, other types of wireless links, or combinations thereof.

Figure 14:
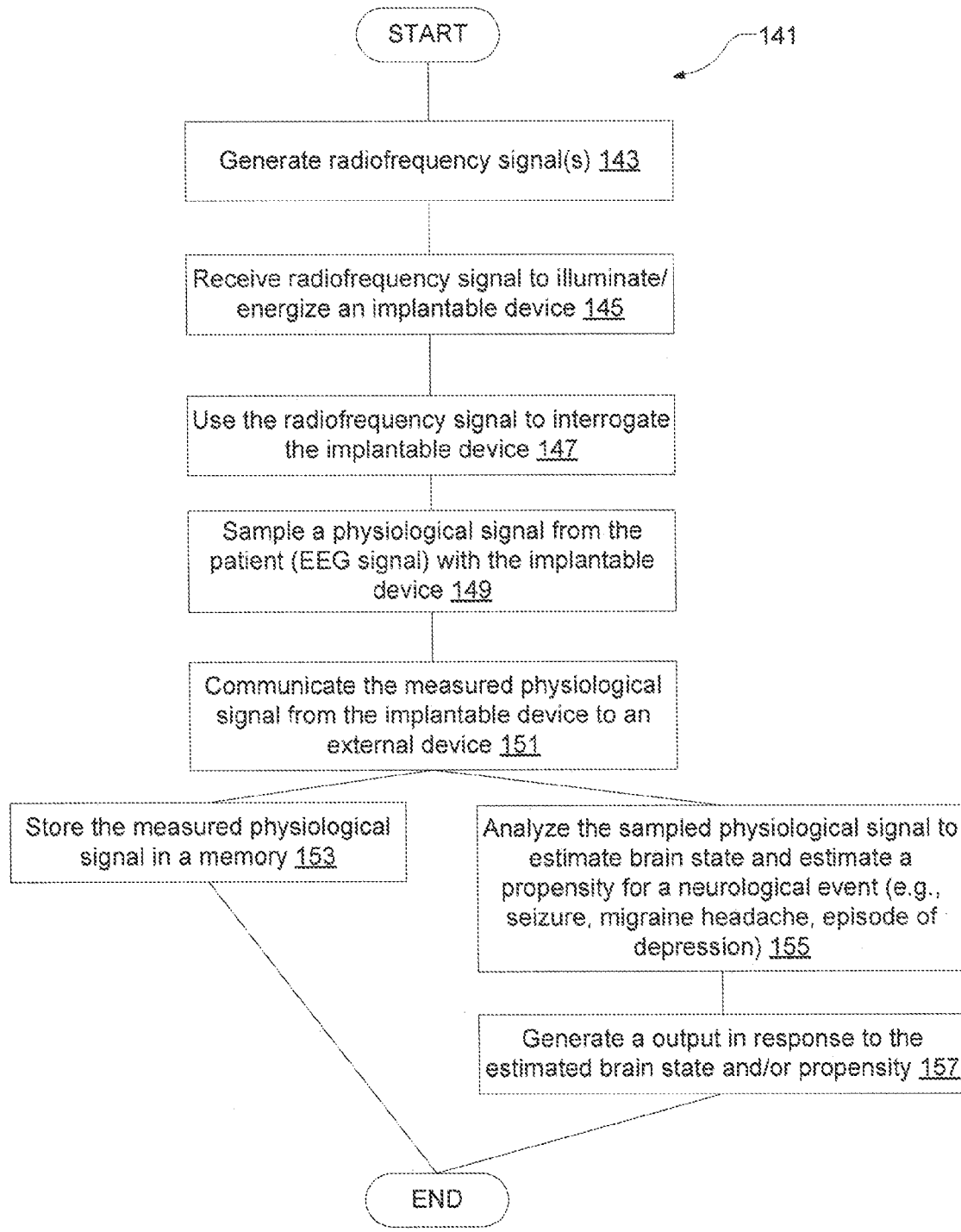
FIG. 14 illustrates simplified methods of operating the system of the present invention.

One preferred method 61 of wirelessly transmitting data and power is carried out with a radiofrequency link, similar to the link used with radiofrequency identification (RFID) tags. As illustrated in FIGS. 13 and 14, in such embodiments, one or more radio frequency signals are emitted from the external device 64 through antenna 68 (step 143). If the external device 64 is in communication range of the implantable devices, at step 145 the radiofrequency (RF) energy signal illuminates the passive, implantable devices 62.

At step 147 the same RF signal interrogates the energized implantable device 62 to allow the implantable device to sample the desired physiological signal from the subject (such as an EEG signal). At step 149, the implantable device samples the instantaneous EEG signal (or other physiological signal) from the subject.

At step 151, the implantable device 62 then communicates a return RF signal to the external device 64 that is encoded with data that is indicative of the sampled EEG signal. Typically, the return RF signal is a based on the RF signal generated by the external device and includes detectable modifications which indicate the sampled EEG signal. For example, the return signal is typically a backscattering of the RF signal from the external device with the detectable modifications that indicate the sampled EEG signal. Advantageously, such backscattering does not require generation of a separate radiating signal and would not require an internal power source. The return RF signals may also include the identification code of the implanted device so as to identify which device the data is coming from. At step 153, the return RF signal emitted by the internal device 62 is received by the antenna 68, and the RF signal is decoded to extract the sampled EEG signal. The sampled EEG signal may thereafter be stored in a memory of the external device 64. For embodiments in which the method is used to collect data, such data will be stored until accessed by the subject. Typically, such data will be analyzed on a separate device (e.g., physician's computer workstation).

In alternative embodiments, however, in which the external device may comprise software to analyze the data in substantially real-time, the received RF signal with the sampled EEG may be analyzed by the EEG analysis algorithms to estimate the subject's brain state which is typically indicative of the subject's propensity for a neurological event (step 155). The neurological event may be a seizure, migraine headache, episode of depression, tremor, or the like. The estimation of the subject's brain state may cause generation of an output (step 157). The output may be in the form of a control signal to activate a therapeutic device (e.g., implanted in the subject, such as a vagus nerve stimulator, deep brain or cortical stimulator, implanted drug pump, etc.). In other embodiments, the output may be used to activate a user interface on the external device to produce an output communication to the subject. For example, the external device may be used to provide a substantially continuous output or periodic output communication to the subject that indicates their brain state and/or propensity for the neurological event. Such a communication could allow the subject to manually initiate therapy (e.g., wave wand over implanted vagus nerve stimulator, cortical, or deep brain stimulator, take a fast acting AED, etc.) or to make themselves safe.

In preferred embodiments, the return RF signal is transmitted (e.g., backscattered) immediately after sampling of the EEG signal to allow for substantially real-time transfer (and analysis) of the subject's EEG signals. In alternate embodiments, however, the return RF signal may be buffered in an internal memory and the communication transmission to the external device 64 may be delayed by any desired time period and may include the buffered EEG signal and/or a real-time sampled EEG signal. The return RF signal may use the same frequency as the illumination RF signal or it may be a different frequency as the illumination RF signal.

Unlike conventional digital implantable devices that send large packets of stored data with each return RF communication transmission, some embodiments of the methods and devices of the present invention substantially continuously sample physiological signals from the subject and communicate in real-time small amounts of data during each return RF signal communication. Because only small amounts of data (one or a small number of sampled EEG signals from each implantable device 62) are transmitted during each communication, a lower amount of power is consumed and the illumination of the implanted device from the incoming high-frequency RF signal will be sufficient to power the implantable device 62 for a time that is sufficient to allow for sampling of the subject's EEG signal. Consequently, in most embodiments no internal power source, such as a battery, is needed in the implantable device 62—which further reduces the package size of the implantable device 62.

The implantable devices 62 and the external devices 64 of the present invention typically use an electromagnetic field/high frequency communication link to both illuminate the implantable device and enable high data transfer rates. Conventional systems typically have an internally powered implantable device and use a slower communication link (e.g., that is designed for long link access delays) and transmit data out on a non-continuous basis. In contrast, some embodiments of the present invention use a fast access communication link that transmits a smaller bursts of data (e.g., single or small number of EEG sample at a time) on a substantially continuous basis.

The frequencies used to illuminate and transfer data between the implantable devices 62 and external device 64 are typically between 13.56 MHz and 10 GHz, preferably between 402 MHz and 2.4 GHz, more preferably between 900 MHz and 2.4 GHz. While it is possible to use frequencies above 2.4 GHz, Applicants have found that it is preferred to use a frequency below 2.4 GHz in order to limit attenuation effects caused by tissue. As can be appreciated, while the aforementioned frequencies are the preferred frequencies, the present invention is not limited to such frequencies and other frequencies that are higher and lower may also be used. For example, it may be desirable us use the MICS (Medical Implant Communication Service band) that is between 402-405 MHz to facilitate the communication link. In Europe, it may be desirable to use ETSI RFID allocation 869.4-869.65 MHz.

While not illustrated in FIG. 14, the system 60 of the present invention may also make use of conventional or proprietary forward error correction ("FEC") methods to control errors and ensure the integrity of the data transmitted from the implantable device 62 to the external device 64. Such forward error correction methods may include such conventional implementations such as cyclic redundancy check ("CRC"), checksums, or the like.

If desired, the data signals that are wirelessly transmitted from implantable device 62 may be encrypted prior to transmission to the control module 66. Alternatively, the data signals may be transmitted to the control module 66 as unencrypted data, and at some point prior to the storage of the data signals in the control module 66 or prior to transfer of the data signals to the physician's office, the EEG data may be encrypted so as to help ensure the privacy of the subject data.

FIGS. 16A and 16B illustrate two embodiments of the externally powered leadless, implantable device 62 that may be used with the system 60 of the present invention. The implantable devices 62 of the present invention are preferably passive or semi-passive and are "slaves" to the "master" external device 64. The implantable devices will typically remain dormant until they are interrogated and possibly energized by an appropriate RF signal from the external device 64. As will be described below, the implantable device 64 may have minimal electronic components and computing power, so as to enable a small package size for the implantable device.

Advantageously, the embodiment illustrated in FIGS. 16A and 16B are minimally invasive and may be implanted with an introducer, trocar or syringe-like device under local anesthesia by a physician or potentially even a physician's assistant. Typically, the implanted device of FIG. 16A may have a longitudinal dimension 1620 of less than about 3 cm, and preferably between about 1 cm and about 10 cm, and a lateral dimension 1622 of less than about 2 mm, and preferably between about 0.5 mm and about 10 mm. As can be appreciated, such dimensions are merely illustrative, and other embodiments of implanted device may have larger or smaller dimensions.

FIG. 16A illustrates an embodiment that comprises a first electrode 1624 and a second electrode 1626 that are disposed on opposing ends of housing 1628. The first and second electrodes 1624, 1626 may be composed of platinum, platinum-iridium alloy, stainless steel, or any other conventional material. The electrodes may include a coating or surface treatment such as platinum-iridium or platinum-black in order to reduce electrical impedance. The first and second electrodes 1624, 1626 will typically have a smooth or rounded shape in order to reduce tissue erosion and may have a surface area of about 3 $mm^2$, but other embodiments may be smaller or larger. Since electrodes 1624, 1626 are typically adapted to only sense physiological signals and are not used to deliver stimulation, the surface area of the electrodes may be smaller than conventional implantable devices. The smaller electrodes have the advantage of reducing the overall device size which can be beneficial for improving subject comfort and reducing the risk of tissue erosion.

Housing 1628 is typically in the form of a radially symmetrical, substantially cylindrical body that hermetically seals electronic components 1630 disposed within a cavity 1632. Housing 1628 may be composed of a biocompatible material, such as glass, ceramic, liquid crystal polymer, or other materials that are inert and biocompatible to the human body and able to hermetically seal electronic components. Housing 1628 may have embedded within or disposed thereon one or more x-ray visible markers 33 that allow for x-ray localization of the implantable device. Alternatively, one or more x-ray visible markers may be disposed within the cavity 1632. Cavity 1632 may be filled with an inert gas or liquid, such as an inert helium nitrogen mixture which may also be used to facilitate package leakage testing. Alternatively, it may be desirable to fill the cavity 1632 with a liquid encapsulant (not shown) that hardens around the electronic components. The liquid encapsulant may comprise silicone, urethane, or other similar materials.

While housing 1628 is illustrated as a substantially cylindrical body with the electrodes 1624, 1626 on opposing ends, housing may take any desired shape and the electrodes may be positioned at any position/orientation on the housing 1628. For example, housing 1628 may taper in one direction, be substantially spherical, substantially oval, substantially flat, or the like. Additionally or alternatively, the body may have one or more substantially planar surfaces so as to enhance the conformity to the subject's skull and to prevent rotation of the implantable device 62. While not shown, housing 1628 may optionally include a conductive electromagnetic interference shield (EMI) that is configured to shield the electronic components 1630 in housing 1628. The EMI shield may be disposed on an inner surface of the housing, outer surface of the housing, or impregnated within the housing.

If desired, housing 1628 may optionally comprise an anchoring assembly (not shown) that improves the anchoring of the implantable device 62 to the skull or the layers within the scalp. Such anchoring may be carried out with adhesive, spikes, barbs, protuberances, suture holes, sutures, screws or the like.

In the illustrated embodiment, first electrode 1624 is disposed on a first end of housing 1628 and is in electrical communication with the electronic components 1630 through a hermetic feedthrough 1634. Feedthrough 1634 may be the same material as the first electrode 1624 or it may be composed of a material that has a similar coefficient of thermal expansion as the housing 1628 and/or the first electrode 1624. Feedthrough 1634 may make direct contact with a pad (not shown) on a printed circuit board 1636, or any other type of conventional connection may be used (e.g., solder ball, bond wire, wire lead, or the like) to make an electrical connection to the printed circuit board 1636.

Second electrode 1626 may be spaced from a second, opposing end of the housing 1628 via an elongated coil member 1638. In the illustrated embodiment, the second electrode 1626 typically comprises a protuberance 1639 that is disposed within and attached to a distal end of the coil member 1638. Coil member 1638 acts as an electrical connection between second electrode and the electronic components 1630 disposed within housing 1628.

Coil member 1638 will typically be composed of stainless steel, a high strength alloy such as MP35N, or a combination of materials such as a MP35N outer layer with silver core.

The illustrated embodiment shows that coil member 1638 has a largest lateral dimension (e.g., diameter) that is less than the largest lateral dimension (e.g., diameter) of housing 1628, but in other embodiments, the coil may have the same lateral dimension or larger lateral dimension from housing 1628.

Coil member 1638 may also be used as an antenna to facilitate the wireless transmission of power and data between the implantable device 62 and the external device 64 (or other device). In preferred embodiments, coil member 1638 may be used to receive and transmit radiofrequency signals. In alternative embodiments, however, coil member 1638 may be inductively coupled to an external coil to receive energy from a modulating, alternating magnetic field. Unlike other conventional implantable devices, the RF antenna is disposed outside of the housing 1628 and extends from one end of housing 1628. It should be appreciated, however, that the present invention is not limited to a substantially cylindrical antenna extending from an end of the housing 1628 and various other configurations are possible. For example, it may be desirable to wind the antenna around or within the housing 1628. Furthermore, it may be desirable to use a substantially flat antenna (similar to RFID tags) to facilitate the transmission of power and data. To facilitate implantation, such antennas may be rolled into a cylindrical shape and biased to take the flat shape upon release from the introducer.

While not shown, it may also be desirable to provide a second antenna between the first electrode 1624 and the housing 1628. The second antenna may be used for power and downlink using a first frequency, e.g., 13.56 MHz, while the first antenna may be used for uplink using a second frequency, e.g., 902-928 MHz. In such embodiments, however, the implantable devices would need to have an internal timebase (e.g., oscillator and a frequency synthesizer). For the embodiments that use only a single frequency for the downlink and uplink, an internal timebase or frequency synthesizer is not needed—and the timebase established by the master (e.g., external device 64) can be used.

Coil member 1638 may be in electrical communication with the electronic components 1630 with a hermetic feedthrough 1642 that extends through a via 1644 in housing 1628. Feedthrough 1642 is typically composed of a material that has a coefficient of thermal expansion that is substantially similar to the material of housing 1640. Because the coil member 1638 is outside of the housing 1628 the length of the implantable device 62 will be increased, but the flexible coil will be better exposed to the RF signals and will be allowed to conform to the shape of the subject's skull.

Coil member 1638 is typically disposed outside of the housing 1628 and disposed within an elongate, substantially flexible housing 1640. Compared to the more rigid housing 1628, the flexible housing 1640 is better able to conform to the shape of an outer surface of the subject's skull, more comfortable for the subject and reduces the chance of tissue erosion. Flexible housing 1640 may comprise silicone, polyurethane, or the like In the illustrated embodiment, flexible housing 1640 extends along the entire length of coil member 1638, but in other embodiments, flexible housing 1640 may extend less than or longer than the longitudinal length of coil member 1638. Flexible housing 1640 will typically have a substantially cylindrical shape, but if desired a proximal end 1646 of the cylindrical housing may be enlarged or otherwise shaped to substantially conform to a shape of the housing 1628. The shaped proximal end 1646 may be adhered or otherwise attached to the end of the housing 1640 to improve the hermetic seal of the housing and may reduce any potential sharp edge or transition between the housings 1628, 1640. While FIG. 16A only illustrates a single layered flexible housing, if desired, the flexible housing 1640 may comprise a plurality of layers, and the different layers may comprise different types of materials, have embedded x-ray markers, or the like.

A longitudinal length of flexible housing 1640 and the longitudinal length of the rigid housing 1628 may vary depending on the specific embodiment, but a ratio of the longitudinal length of the flexible housing 1640: the longitudinal length of the more rigid housing 1628 is typically between about 0.5:1 and about 3:1, and preferably between about 1:1 and about 2:1. By having the longitudinal length of the flexible housing longer than the longitudinal length of the rigid housing, advantageously the implantable device will be more comfortable and better able to conform to the outer surface of the subject's skull. In alternative embodiments, it may also be desirable to have a longitudinal length of the rigid housing 1628 be longer than the longitudinal length of the flexible housing 1640, or in any other desired configuration.

Because the implantable devices 62 of the present invention consume a minimal amount of energy and use a high frequency RF coupling to power the device and communicate the EEG signals to the external device, unlike other conventional devices, some of the implantable devices 62 of the present invention will not need a ferrite core to store energy, and the electronic components 1630 of the present invention will typically include aluminum or other MRI-safe material. Consequently, the subject's implanted with the implantable device 62 may safely undergo MRI imaging.

FIG. 16B illustrates another embodiment of implantable device 62 that is encompassed by the present invention. The embodiment of FIG. 16B shares many of the same components as the embodiment of FIG. 16A, and such components are noted with the same reference numbers as FIG. 16A. There are, however, a few notable exceptions. Specifically, instead of having a hermetically sealed housing, the embodiment of FIG. 16B provides a conductive body 48 that acts as both the housing for the electronic components 1630 and as the second electrode. Conductive body 48 may be composed of a metalized polymer, one or more metal or metal alloys, or other conductive material. Because body 48 is conductive, it may act as an electromagnetic interference (EMI) shield to the electronic components disposed within the cavity 1632. Electrical connections to the printed circuit board 1636 may be carried out with one or more conductive spring conductors 1650 or other conventional lead connectors.

Feedthrough 1642 that is connected to the coil member 1638 extends from the end of coil member 1638 and makes an electrical connection with a lead on the printed circuit board 1636. The feedthrough 1642 works in conjunction with one or more dielectric seals or spacers 52 to hermetically seal the cavity 1632. Similar to above, the cavity 1632 may be filled with an inert gas or an encapsulant. The proximal end 1646 of flexible body 1640 may be coupled to the seals 52 and/or coupled to the conductive body 48.

As shown in the embodiment of FIG. 16B, the surface area of conductive body 48 (e.g., the first electrode) may be larger than the surface area of the second electrode 1626. In other embodiments, however, the surface area of the second electrode 1626 may have the substantially same surface area and/or shape as the conductive body 48.

In most embodiments, the implantable devices shown in FIGS. 16A and 16B function completely independent of the other implantable devices 62 and there is no physical connection or communication between the various devices. If desired, however, the implantable devices 62 may be physically coupled to each other with a connecting wire or tether and/or in communication with each other. If the plurality of implanted devices 62 are in communication with one another, it may be desired to use a communication frequency between the implanted devices 62 that is different from the frequency to communicate between the implanted devices and the external device 64. Of course, the communication frequency between the implanted devices 62 may also be the same frequency as the communication frequency with the external device 64.

Figure 16C:
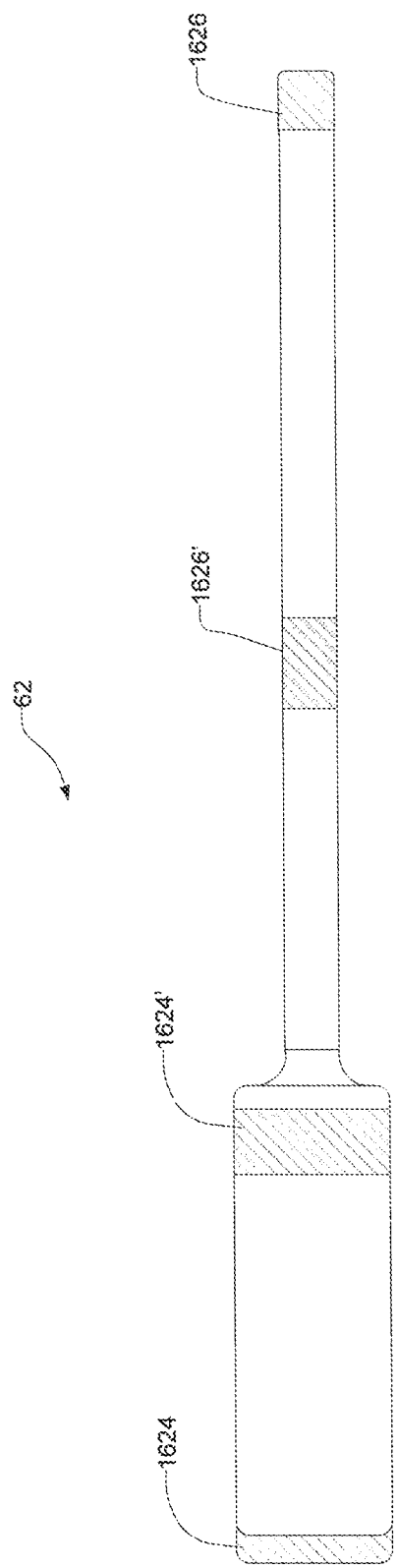
FIG. 16C illustrates a simplified plan view of an embodiment that comprises four electrodes disposed on the implanted device.

While FIGS. 16A and 16B illustrate a first and second electrode 1624, 1626, the implantable devices 62 of the present invention are not limited to only two electrodes. Any number of electrodes may be coupled to the implantable device in any orientation. For example, the electrodes do not have to extend from ends of the housing, but may be positioned anywhere along a portion of the housings 1628, 1640. Furthermore, a plurality of electrodes and their leads may be disposed along the length of the flexible housing 1640 and/or rigid housing 1628 so as to provide more than two electrodes per implantable device. For example, FIG. 16C illustrates a simplified embodiment in which there are two additional electrode 1624', 1626' positioned on the rigid housing 1628 and flexible housing 1640, respectively. The spacing between the various contacts 1624, 1624', 1626, 1626' may vary or be the same distance between each other. The spacing between electrodes will likely depend on the overall length of the implantable device, but will typically be between about 2 mm and about 20 mm and preferably be between about 5 mm and about 10 mm. In addition to the embodiment shown in FIG. 16C, it may be desirable to have the additional electrodes only on the flexible housing 1640 or only on the rigid housing 1628. While only four electrodes are shown on the implanted device, it should be appreciated that any desirable number of electrodes (e.g., anywhere between about two electrodes and about sixteen electrodes) may coupled to the implanted device.

While FIGS. 16A-16B illustrate some currently preferred embodiments of the implantable device 62, the present invention further encompasses other types of minimally invasive implantable devices 62 that can monitor the brain activity and other physiological signals from the subject. For example, a plurality of electrodes might reside on a single lead that could be tunneled under the scalp from a single point of entry. Examples of such embodiments are shown in FIGS. 15A-15E.

Such implantable devices 62 include an active electrode contact 400 that is in communication with one or more passive electrode contacts 401. The active electrode contact 400 may be used to facilitate monitoring of the physiological signals using the array of active and passive electrode contacts. The arrays of electrode contacts may be arranged in a linear orientation (FIG. 15C) or in a grid pattern (FIG. 15E), or any other desired pattern (e.g., circular, star pattern, customized asymmetric pattern, etc.) For example, if the implantable device comprises two electrode contacts (e.g., one active contact and one passive contact), such an embodiment would have a similar configuration as the embodiment of FIG. 16A. Similarly, if the implantable device were to have four substantially linearly positioned electrode contacts (e.g., one active contact and three passive contacts), such an embodiment would be substantially similar to the configuration shown in FIG. 16C.

Figure 15A:
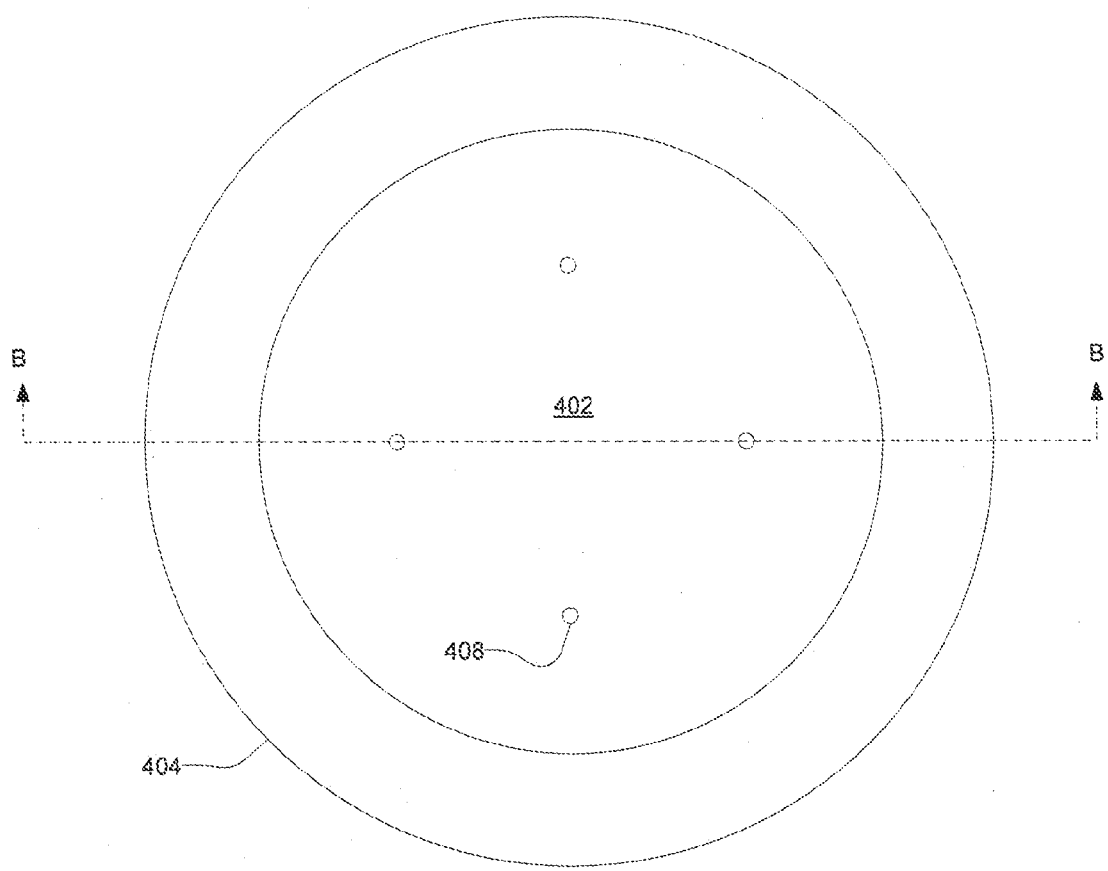
FIG. 15A illustrates a bottom view of one embodiment of an active implantable device that is encompassed by the present invention.

FIG. 15A illustrates a bottom view of an active electrode contact 400 that may be part of the implantable device 62 of the present invention. The active electrode contact comprises a base 402 that is coupled to a contact portion 404. The base 402 and contact portion may be composed of any number of different types of materials, such as platinum, platinum-iridium alloy, stainless steel, or any other conventional material. In preferred embodiments, both the base 402 and contact portion 404 are formed to their desired shape. The base 402 may comprise a plurality of hermetic feedthroughs 413 that is implemented using conventional glass metal seal technology (e.g., pins 408, glass seal 414, and vias 406). The hermetic feedthroughs 413 may be used to connect to an antenna (not shown) for communication with the external device 64 or to make an electrical connection with an adjacent passive electrode contact 401 in the implanted device 62. In the illustrated embodiment, base 402 comprises four hermetic feedthroughs 413. But as can be appreciated the base 402 may comprise any desired number of feedthroughs 413 (e.g., anywhere between two and sixty four feedthroughs).

Figure 15B:
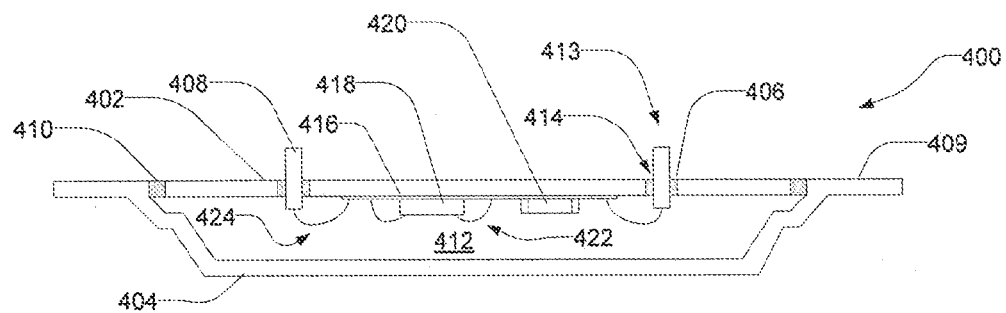
FIG. 15B illustrates a cross-sectional view of the active implantable device of FIG. 15A along lines B-B.

FIG. 15B illustrates a cross-sectional view of the active electrode contact 400 along lines B-B in FIG. 15A. As shown in FIG. 15B, the contact portion 404 is shaped to as to align the base 402 along a bottom surface defined by flanges 409. Base 402 may be coupled to the contact portion 404 with a laser weld, glass metal seal, or other conventional connector 410 along an outer perimeter of the base 402 to hermetically seal components of the active electrode contact within a cavity 412 defined by the base 402 and contact portion 404. If desired, the cavity 412 may be backfilled with nitrogen and/or helium to facilitate package leak testing.

A thin or thick filmed microcircuit or a printed circuit board ("PCB") 416 may be mounted onto an inner surface of the base 402. PCB 416 may have active components 418 (e.g., integrated circuits, ASIC, memory, etc.) and passive components 420 (e.g., resistors, capacitors, etc.) mounted thereto. Leads or bond wires 422 from the active and passive components may be electrically attached to pads on the PCB (not shown) which make electrical connections to leads or bond wires 424 that are attached to the hermetic feedthroughs 413. While not shown in FIG. 15B, the active electrode contact 400 may comprise a rechargeable or non-rechargeable power supply (e.g., batteries), and/or x-ray visible markers (not shown).

Figure 15C:
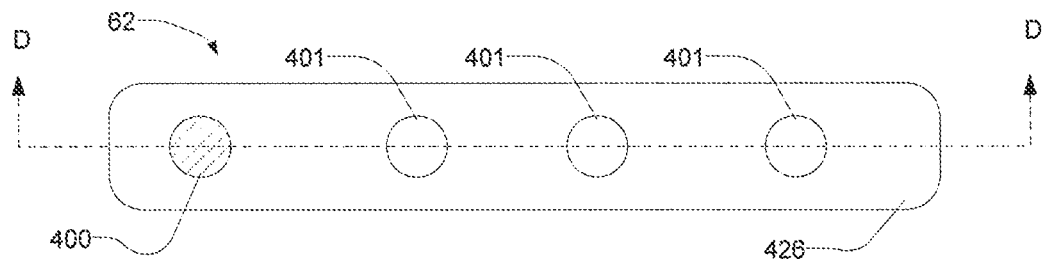
FIG. 15C is a linear implantable device that comprises a plurality of electrode contacts in which at least one electrode contact comprises the active implantable device of FIG. 15A.
Figure 15D:
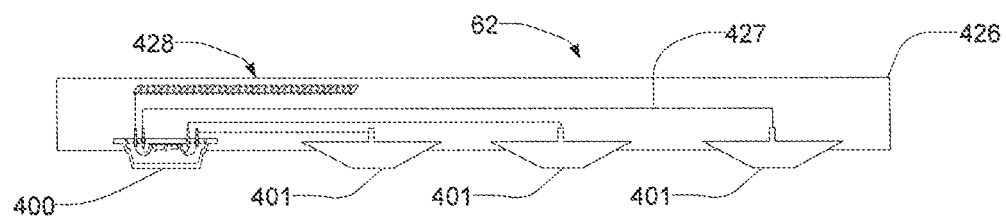
FIG. 15D is a cross sectional view of the implantable device of FIG. 15C along lines D-D.

As noted above, the active contacts may be used in conjunction with one or more passive contacts to form an active implantable device 62 to facilitate monitoring of the subject's physiological signals and to communicate with the external device 64. FIGS. 15C and 15D illustrate an embodiment of the implantable device 62 in which one active contact 400 is housed in a body 426 along with a plurality of passive contacts 401 to form a multiple contact implantable device 62. The contact portion of the active contact 400 is exposed through an opening in the body 426 to allow for sampling of the physiological signals (e.g., EEG) from the subject. The body 426 may be substantially flexible or rigid and may have similar dimensions and/or shapes as the embodiments shown in FIGS. 16A-16C. Body 426 may be composed of a biocompatible material such as silicone, polyurethane, or other materials that are inert and biocompatible to the human body. Body 426 may also be composed of a rigid material such as polycarbonate. The implantable device may be injected into the subject using the introducer assembly shown in FIG. 19 and methods shown in FIG. 20.

As shown in FIG. 15D wire leads 427 may extend from the passive contacts 401 and be electrically and physically coupled to one of the hermetic feedthroughs 413 of the active contact 400 to facilitate sampling of the physiological signals using all four electrode contacts. For embodiments which use a wireless link (e.g., RF) to wirelessly transmit data to the external device 64 and optionally to power the device, one of the feedthroughs may be coupled to an antenna 428 that is configured to wirelessly communicate with the external device. It should be appreciated, that while not described herein, the embodiments of FIGS. 15C-15E may have any of the components or variations as described above in relation to FIGS. 16A-16B.

Figure 15E:
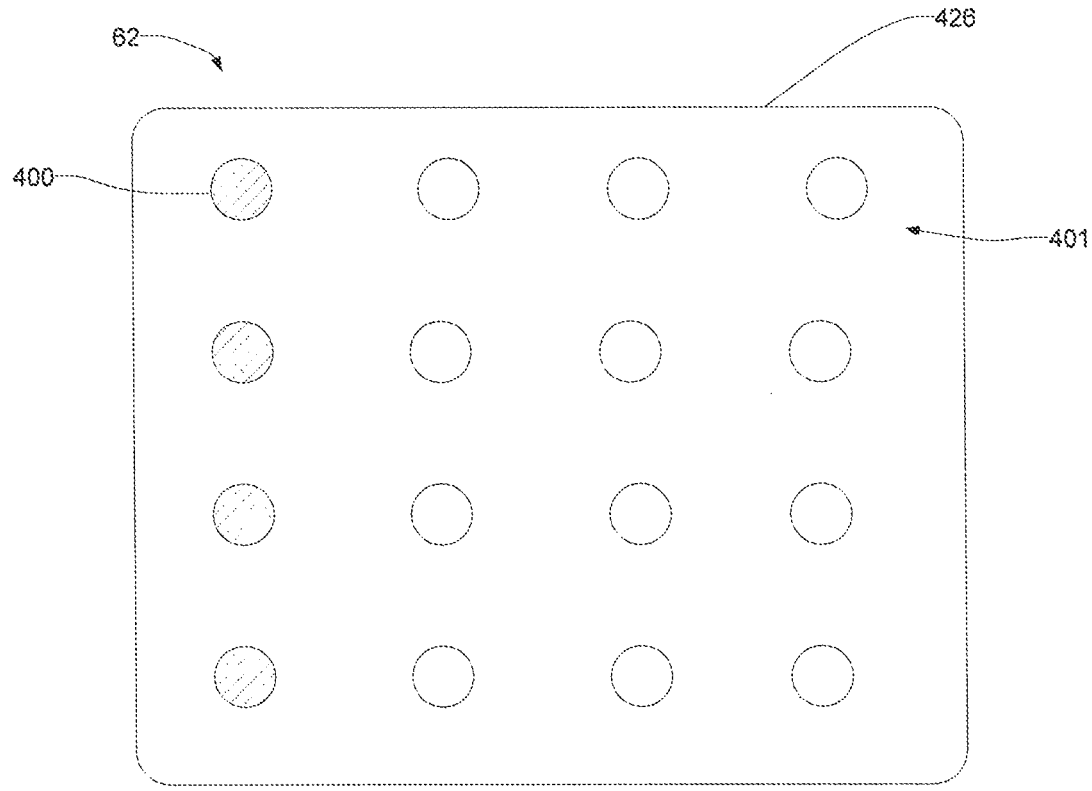
FIG. 15E is a 4×4 electrode array that comprises a plurality of electrode contacts in which at least one electrode contact comprises the active implantable contact of FIG. 15A.

FIG. 15E illustrates an alternative embodiment of the implantable device 62 in which the implantable device 62 is in the form of a 4×4 grid array of active and passive contacts. At least one of the electrode contacts may be an active contact 400 so as to facilitate monitoring of the subject's physiological signals with the array. In the illustrated embodiment, the contacts in the leftmost column (highlighted with cross-hatching) are active electrode contacts 400, and the contacts in remaining column are electrically connected to one of the active contacts 400. Of course, any number of active contacts 400 and passive contacts 401 may be in the grid array and the active contact(s) 400 may be positioned anywhere desired. For example, if the active electrode contact 400 has sixteen or more hermetic feedthroughs, only one of the contacts in the array needs to be active and the remaining fifteen contacts could be passive contacts.

Figure 17:
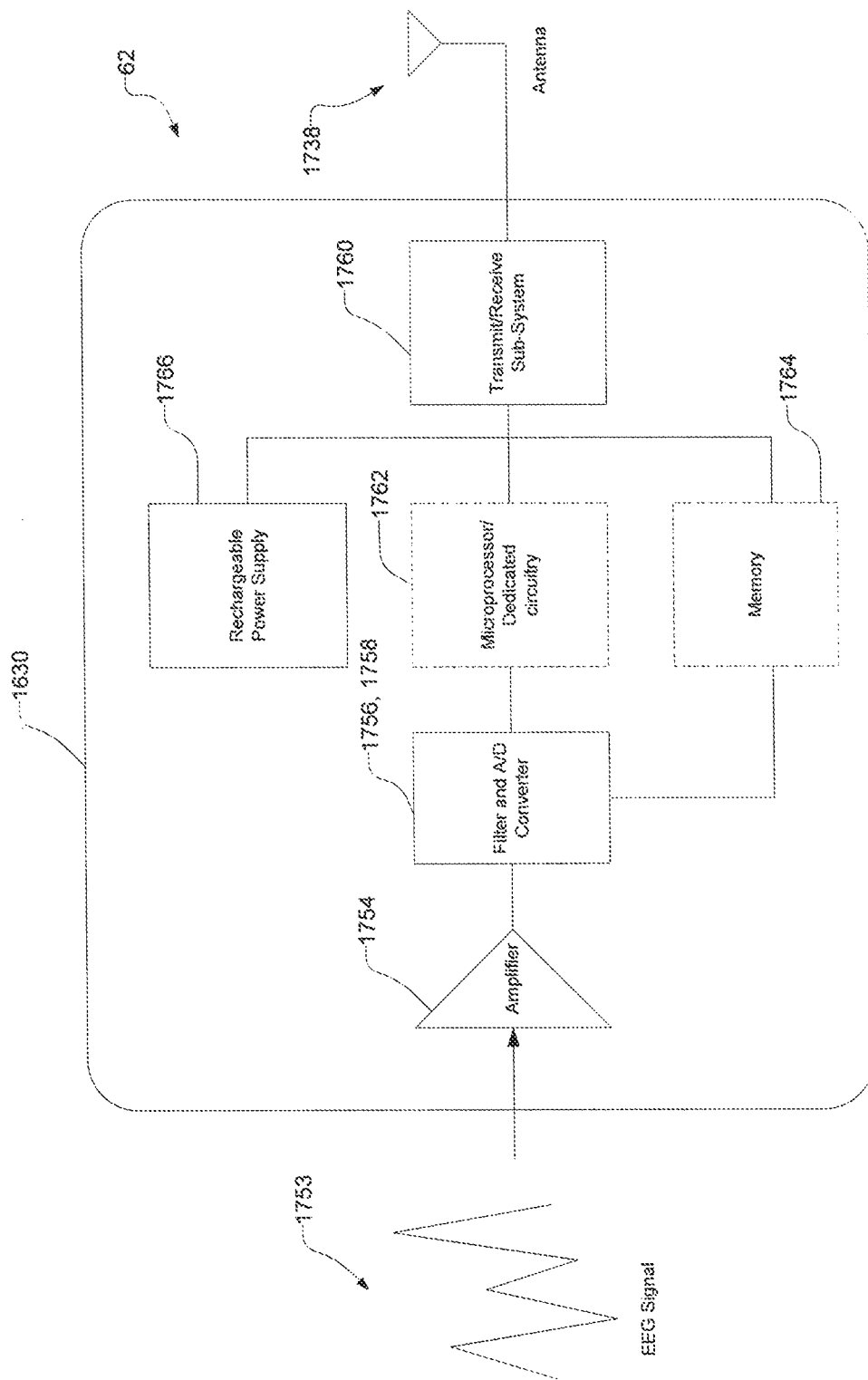
FIG. 17 illustrates one embodiment of the electronic components that may be disposed within the implantable device.

FIG. 17 illustrates one simplified embodiment of the electronic components 1630 (e.g., active components 418 and passive components 420 in FIG. 15B) that may be disposed in the implantable devices 62 as shown in FIGS. 15A-16C. It should be appreciated, however, that the electronic components 1630 of the implantable device 62 may include any combination of conventional hardware, software and/or firmware to carry out the functionality described herein. For example, the electronic components 1630 may include many of the components that are used in passive RF integrated circuits.

The first and second electrodes will be used to sample a physiological signal from the subject—typically an EEG signal 1753, and transmit the sampled signal to the electronic components 1630. While it may be possible to record and transmit the analog EEG signal to the external device, the analog EEG signal will typically undergo processing before transmission to the external device 64. The electronic components typically include a printed circuit board that has, among others, an amplifier 1754, one or more filters 1756 (e.g., bandpass, notch, lowpass, and/or highpass) and an analog-to-digital converter 1758. In some embodiments, the processed EEG signals may be sent to a transmit/receive sub-system 60 for wireless transmission to the external device via an antenna (e.g., coil member 1638). Additional electronic components that might be useful in implantable device 62 may be found in U.S. Pat. Nos. 5,193,539, 5,193,540, 5,312,439, 5,324,316, 5,405,367 and 6,051,017.

In some alternative embodiments of the present invention, the electronic components 1630 may include a memory 1764 (e.g., RAM, EEPROM, Flash, etc.) for permanently or temporarily storing or buffering the processed EEG signal. For example, memory 1764 may be used as a buffer to temporarily store the processed EEG signal if there are problems with transmitting the data to the external device. For example, if the external device's power supply is low, the memory in the external device is removed, or if the external device is out of communication range with the implantable device, the EEG signals may be temporarily buffered in memory 1764 and the buffered EEG signals and the current sampled EEG signals may be transmitted to the external device when the problem has been corrected. If there are problems with the transmission of the data from the implantable device, the external device may be configured to provide a warning or other output signal to the subject to inform them to correct the problem. Upon correction of the problems, the implantable device may automatically continue the transfer the temporarily buffered data and the real-time EEG data to the memory in the external device.

The electronic components 1630 may optionally comprise dedicated circuitry and/or a microprocessor 1762 (referred to herein collectively as "microprocessor") for further processing of the EEG signals prior to transmission to the external device. The microprocessor 1762 may execute EEG analysis software, such as a seizure prediction algorithm, a seizure detection algorithm, safety algorithm, or portions of such algorithms, or portions thereof. For example, in some configurations, the microprocessor may run one or more feature extractors that extract features from the EEG signal that are relevant to the purpose of monitoring. Thus, if the system is being used for diagnosing or monitoring epileptic subjects, the extracted features (either alone or in combination with other features) may be indicative of the subject's susceptibility to or protection from a neurological event (e.g., pro-ictal or contra-ictal). Once the feature(s) are extracted, the microprocessor 1762 may send the extracted feature(s) to the transmit/receive sub-system 1760 for the wireless transmission to the external device and/or store the extracted feature(s) in memory 1764. Because the transmission of the extracted features is likely to include less data than the EEG signal itself, such a configuration will likely reduce the bandwidth requirements for the communication link between the implantable device 62 and the external device 64. Since the extracted features do not add a large amount of data to the data signal, in some embodiments, it may also be desirable to concurrently transmit both the extracted feature and the EEG signal. A detailed discussion of various embodiments of the internal/external placement of such algorithms are described in commonly-owned U.S.

patent application Ser. No. 11/322,150, filed Dec. 28, 2005 to Bland et al., the complete disclosure of which is incorporated herein by reference.

While most embodiments of the implantable device 62 are passive and do not need an internal power source or internal clock, in some embodiments, the electronic components 1630 may include a rechargeable or non-rechargeable power supply 1766 and an internal clock (not shown). The rechargeable or non-rechargeable power supply may be a battery, a capacitor, or the like. The rechargeable power supply 1766 may also be in communication with the transmit/receive sub-system 1760 so as to receive power from outside the body by inductive coupling, radiofrequency (RF) coupling, etc. Power supply 1766 will generally be used to provide power to the other components of the implantable device 62. In such embodiments, the implanted device may generate and transmit its own signal with the sampled EEG signal for transmission back to the external device. Consequently, as used herein "transmit" includes both passive transmission of a signal back to the external device (e.g., backscattering of the RF signal) and internal generation of a separate signal for transmission back to the external device.

Figure 18:
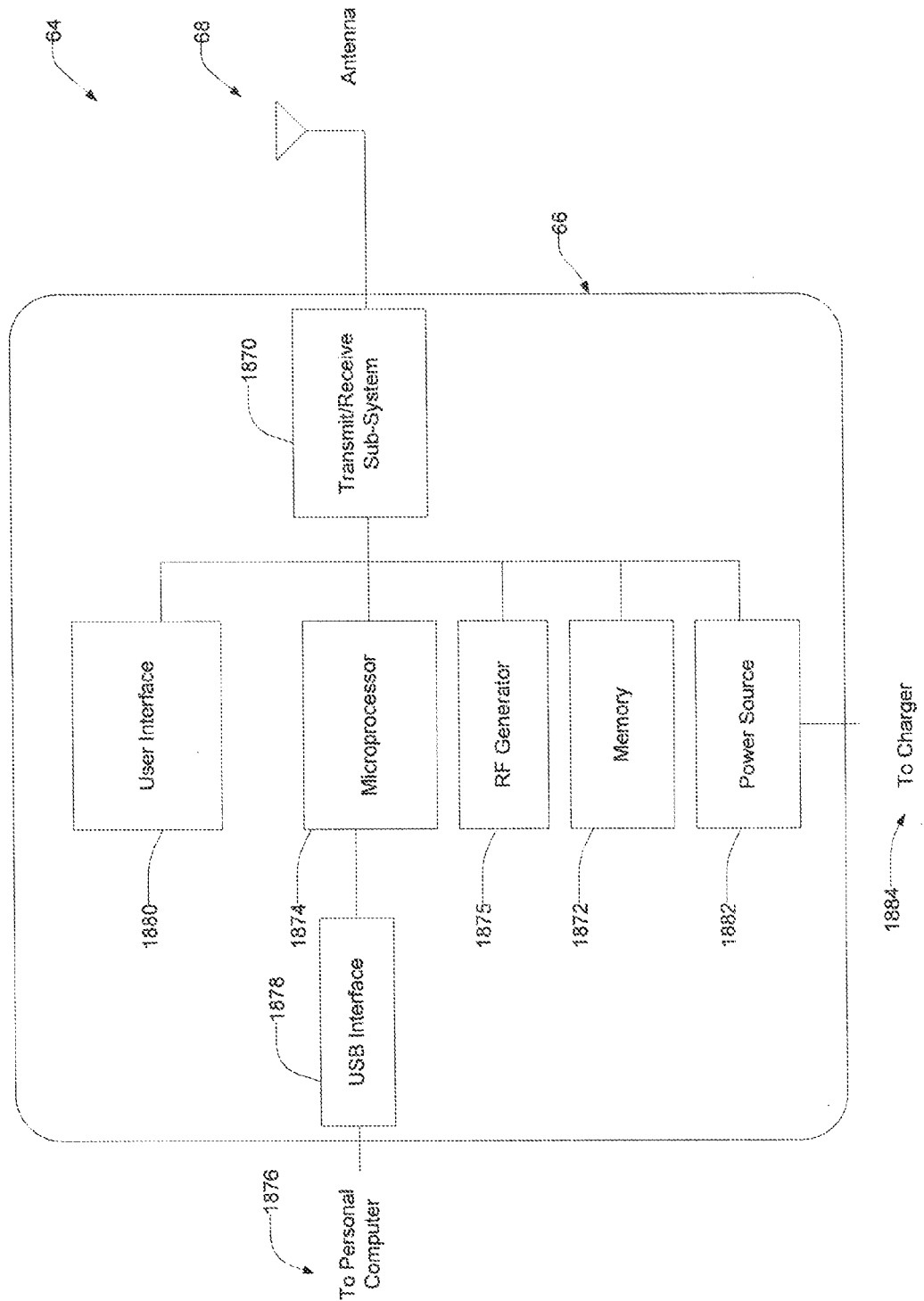
FIG. 18 is a block diagram illustrating one embodiment of electronic components that may be in the external device.

FIG. 18 is a simplified illustration of some of the components that may be included in external device 64. Antenna 68 and a transmit/receive subsystem 70 will receive a data signal that is encoded with the EEG data (or other physiological data) from the antenna 1738 of the implantable device 62 (FIG. 17). As used herein, "EEG data" may include a raw EEG signal, a processed EEG signal, extracted features from the EEG signal, an answer from an implanted EEG analysis software (e.g., safety, prediction and/or detection algorithm), or any combination thereof.

The EEG data may thereafter be stored in memory 1872, such as a hard drive, RAM, permanent or removable Flash Memory, or the like and/or processed by a microprocessor 1874 or other dedicated circuitry. Microprocessor 1874 may be configured to request that the implantable device perform an impedance check between the first and second electrodes and/or other calibrations prior to EEG recording and/or during predetermined times during the recording period to ensure the proper function of the system.

The EEG data may be transmitted from memory 1872 to microprocessor 1874 where the data may optionally undergo additional processing. For example, if the EEG data is encrypted, it may be decrypted. The microprocessor 1874 may also comprise one or more filters that filter out high-frequency artifacts (e.g., muscle movement artifacts, eye-blink artifacts, chewing, etc.) so as to prevent contamination of the high frequency components of the sampled EEG signals. In some embodiments, the microprocessor may process the EEG data to measure the subject's brain state, detect seizures, predict the onset of a future seizure, generate metrics/measurements of seizure activity, or the like. A more complete description of seizure detection algorithms, seizure prediction algorithms, and related components that may be implemented in the external device 64 may be found in pending, commonly-owned U.S. patent application Ser. Nos. 11/321,897 and 11/321,898, filed on Dec. 28, 2005, to Leyde et al. and DiLorenzo et al., and Ser. No. 12/020,450, filed on Jan. 25, 2008, to Snyder et al., the complete disclosures of which are incorporated herein by reference.

It should be appreciated, however, that in some embodiments some or all of the computing power of the system of the present invention may be performed in a computer system or workstation 1876 that is separate from the system 60, and the external device 64 may simply be used as a data collection device. In such embodiments, the personal computer 1876 may be located at the physician's office or at the subject's home and the EEG data stored in memory 1872 may be uploaded to the personal computer 1876 via a USB interface 1878, removal of the memory (e.g., Flash Memory stick), or other conventional communication protocols, and minimal processing may be performed in the external device 64. In such embodiments, the personal computer 1876 may contain the filters, decryption algorithm, EEG analysis software, such as the contra-ictal algorithm, pro-ictal algorithm, and/or detection algorithm, report generation software, or the like. Some embodiments of the present invention may take advantage of a web-based data monitoring/data transfer system, such as those described in U.S. Pat. Nos. 6,471,645 and 6,824,512, the complete disclosures of which are incorporated herein by reference.

External device 64 may also comprise an RF signal generator 1875 that is configured to generate the RF field for interrogating and optionally powering the implanted devices 62. RF generator 1875 will be under control of the microprocessor 1874 and generate the appropriate RF field to facilitate monitoring and transmission of the sampled EEG signals to the external device.

External device 64 will typically include a user interface 1880 for displaying outputs to the subject and for receiving inputs from the subject. The user interface may comprise outputs such as auditory devices (e.g., speakers) visual devices (e.g., LCD display, LEDs to indicate brain state or propensity to seizure), tactile devices (e.g., vibratory mechanisms), or the like, and inputs, such as a plurality of buttons, a touch screen, and/or a scroll wheel.

The user interface may be adapted to allow the subject to indicate and record certain events. For example, the subject may indicate that medication has been taken, the dosage, the type of medication, meal intake, sleep, drowsiness, occurrence of an aura, occurrence of a neurological event, or the like. Such inputs may be used in conjunction with the recorded EEG data to improve the analysis of the subject's condition and determine the efficacy of the medications taken by the subject.

The LCD display of the user interface 80 may be used to output a variety of different communications to the subject including, status of the device (e.g., memory capacity remaining), battery state of one or more components of system, whether or not the external device 64 is within communication range of the implantable devices 62, brain state indicators (e.g., a warning (e.g., seizure warning), a prediction (e.g., seizure prediction), unknown brain state, safety indication, a recommendation (e.g., "take drugs"), or the like). Of course, it may be desirable to provide an audio output or vibratory output to the subject in addition to or as an alternative to the visual display on the LCD. In other embodiments, the brain state indicators may be separate from the LCD display to as to provide a clear separation between the device status outputs and the brain state indicators. In such embodiments, the external device may comprise different colored LEDs to indicate different brain states. For example, a green LED may indicate a safe brain state, a yellow light may indicate an unknown brain state, and a red light may indicate either a seizure detection or seizure prediction.

As noted above and illustrated in FIG. 9, the external device 64 may comprise a plurality of LEDs to provide a substantially continuous, real-time indication to the subject of their condition. In the illustrated embodiment, the LEDs may include three LEDs—a green LED, a yellow LED, and a red LED. While not shown, it may also be desirable to provide additional LEDs of different colors or additional LEDs in each color to indicate a graded condition. As stated above, the period of time associated with a contra-ictal state can be a predetermined time period. There can also be multiple predetermined periods of varying duration. The external device could therefore comprise a plurality of outputs which indicate one of the multiple predetermined contra-ictal periods of time. For example, it may be desirable to illuminate two or more green lights when the subject is in a condition that is determined to be even more unlikely to experience a seizure. More specifically, one green light illuminated could indicate a contra-ictal period duration of 10 minutes, whereas two green lights illuminated could indicate a contra-ictal period of 20 minutes. Or a slowly blinking green light could indicate a longer contra-ictal period than a rapidly blinking green light. On the other extreme, but similarly, it may be desirable to provide, and illuminate, two or more red lights when a seizure is detected or is imminent.

The external device 64 may also include a medical grade power source 1882 or other conventional power supply that is in communication with at least one other component of external device 64. The power source 1882 may be rechargeable. If the power source 1882 is rechargeable, the power source may optionally have an interface for communication with a charger 1884. While not shown in FIG. 18, external device 64 will typically comprise a clock circuit (e.g., oscillator and frequency synthesizer) to provide the time base for synchronizing external device 64 and the implantable device(s) 62. In preferred embodiments, the implantable device(s) 62 are slaves to the external device and the implantable devices 62 will not have to have an individual oscillator and a frequency synthesizer, and the implantable device(s) 62 will use the "master" clock as its time base. Consequently, it may be possible to further reduce the size of the implantable devices 62.

In use, one or more of the implantable devices 62 are implanted in the subject. The implanted device 62 is interrogated and powered so that the EEG signals are sampled from the subject's brain. The EEG signals are processed by the implanted device and the processed EEG signals are wirelessly transmitted from the implanted device(s) to an external device. The EEG signals are stored for future or substantially real-time analysis.

The EEG analysis systems shown in FIG. 2, however, may be embodied in a device that is implanted in the subject's body, external to the subject's body, or a combination thereof. For example, in one embodiment the algorithm system may be fully stored in and processed by the device 62 that is implanted in the subject's body. In such embodiments, the subject's propensity for neurological event characterization (or whatever output is generated by the classifiers) is calculated in the implantable device 62 and a data signal is transmitted to the external device. The external processor performs any remaining processing to generate and provide the communication output to the subject. Such embodiments have the benefit of maintaining processing within the subject, while reducing the communications demands on the implantable device 62.

In other embodiments, the signals 103 sampled from the subject may be partially processed in the implantable device 62 before transmitting data to the external device 64 so as to reduce the total amount of data to be transmitted, thereby reducing the power demands of the transmit/receive subsystem 120. Examples include: digitally compressing the signals before transmitting them; encrypting the signals; selecting only a subset of the measured signals for transmission; selecting a limited segment of time and transmitting signals only from that time segment; extracting salient characteristics of the signals, transmitting data representative of those characteristics rather than the signals themselves, and transmitting only the result of classification. Further processing and analysis of the transmitted data may take place in the external device 64.

In yet other embodiments, it may be possible to perform some of the signal processing in the implantable device 62 and some of the signal processing in the external device 64. For example, one or more characteristics from the one or more signals may be extracted with feature extractors in the implantable device 62. Some or all of the extracted characteristics may be transmitted to the external device 64 where the characteristics may be classified to assess the subject's susceptibility for a neurological event. If desired, external device 64 may be tailored to the individual subject. Consequently, the classifier may be adapted to allow for transmission or receipt of only the characteristics from the implantable device 62 that are useful for that individual subject. Advantageously, by performing feature extraction in the implantable device 62 and classification in an external device at least two benefits may be realized. First, the amount of wireless data transmitted from the implantable device 62 to the external device 64 is reduced (versus transmitting pre-processed data). Second, classification, which embodies the decision or judgment component, may be easily reprogrammed or custom tailored to the subject without having to reprogram the implantable device 62.

In yet another embodiment, feature extraction may be performed external to the body. Pre-processed signals (e.g., filtered, amplified, converted to digital) may be transcutaneously transmitted from implantable device 62 to the external device 64 where one or more characteristics are extracted from the one or more signals with feature extractors. Some or all of the extracted characteristics may be transcutaneously transmitted back into the implantable device 62, where a second stage of processing may be performed on the characteristics, such as classifying of the characteristics (and other signals) to characterize the subject's propensity for the onset of a future neurological event. If desired, to improve bandwidth, the classifier may be adapted to allow for transmission or receipt of only the characteristics from the subject communication assembly that are predictive for that individual subject. Advantageously, because feature extractors may be computationally expensive and energy hungry, it may be desirable to have the feature extractors external to the body, where it is easier to provide more processing and larger power sources.

Other details of devices useful for practicing the invention may be found in co-pending and commonly-owned U.S. patent application Ser. No. 12/020,507, filed Jan. 25, 2008, titled "METHODS AND SYSTEMS FOR MEASURING A PATIENT'S SUSCEPTIBILITY TO A SEIZURE," the disclosure of which is incorporated herein by reference.

One particular advantage of some of the embodiments of the present invention is the ability to provide a substantially continuous, substantially real-time indication to the subject of their neurological condition. In other embodiments of the present invention, the subject may be provided with an indication of their neurological condition on a non-continuous basis. For example, in some embodiments it may be desirable to only provide an output to the subject when there is a change in their condition or if the subject enters a high susceptibility or low susceptibility condition. The ability to inform the subject that they are unlikely to transition to an ictal condition within a period of time will reduce the uncertainty that effects every aspect of their day to day life and opens up the possibility for the subject to perform tasks that most people take for granted.

Such a system would further enable use of novel therapies to prevent the occurrence of the neurological event. Therapies include automatic or manual delivery of anti-epileptic drugs, vagus nerve stimulation, brain stimulation, etc. Some potential therapies are described in commonly-owned U.S. patent application Ser. No. 10/889,844 filed Jul. 12, 2004 to DiLorenzo and Ser. No. 11/321,898, filed Dec. 28, 2005 to Leyde et al., the complete disclosure of which is incorporated herein by reference.

Figure 19:
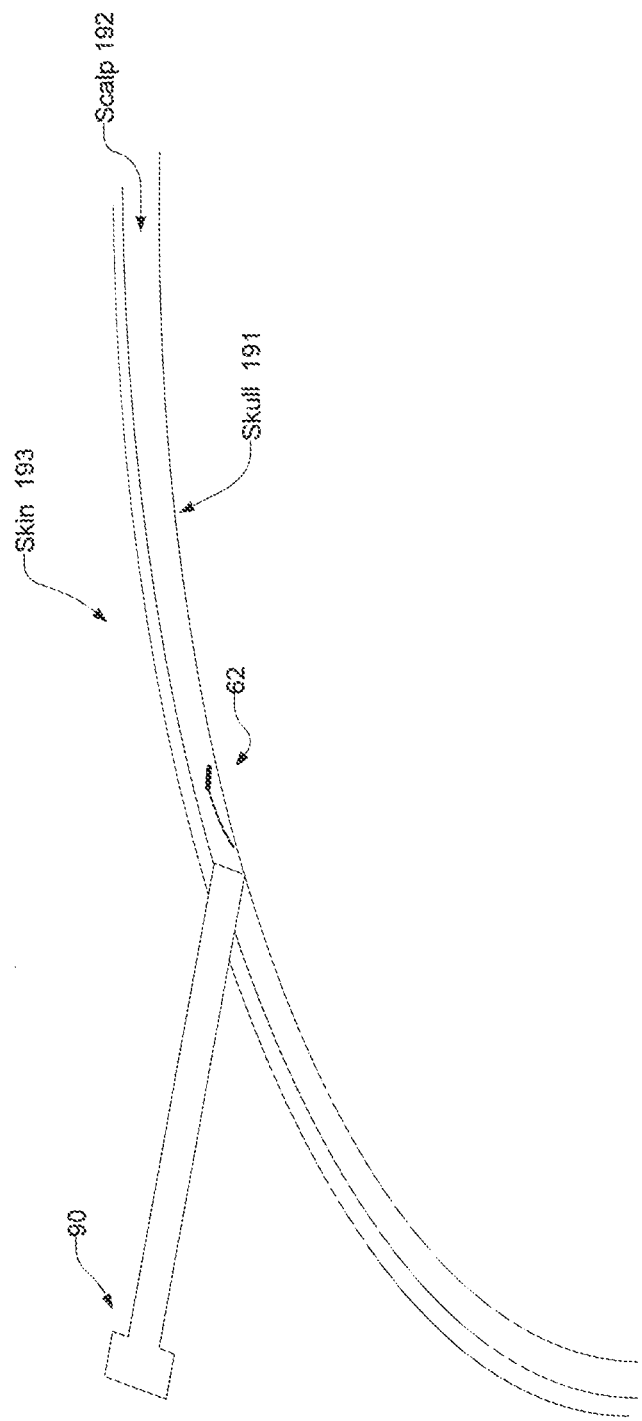
FIG. 19 illustrates a simplified trocar or needle-like device that may be used to implant the implantable device beneath the subject's skin.

As noted above, in preferred embodiments, the implantable devices are implanted in a minimally invasive fashion under the subject's scalp 192 and above an outer surface of the skull 191. FIG. 19 illustrates a simplified introducer assembly 90 that may be used to introduce the implantable devices into the subject. The introducer assembly 90 is typically in the form of a cannula and stylet or a syringe-like device that can access the target area and inject the implanted device under the skin 193 of the subject. As noted above, the implantable devices 62 are preferably implanted beneath at least one layer of the subject's scalp 192 and above the subject's skull 191. Because of the small size of the implantable devices 62, the devices may be injected into the subject under local anesthesia in an out-subject procedure by the physician or neurologist. Because the implantable devices are implanted entirely beneath the skin 193 infection risk would be reduced and there would be minimal cosmetic implications. Due to the small size of the implantable devices 62, it may be desirable to have a plurality of implantable devices pre-loaded into a sterile introducer assembly 90 or into a sterile cartridge (not shown) so as to minimize the risk of contamination of the implantable devices 62 prior to implantation.

While FIG. 19 illustrates one system for implanting the implantable devices in the subject and using the implantable devices to monitor the subject's EEG, a variety of other non-invasive and invasive implantation and monitoring methods may be used. For example, while minimally invasive monitoring may be preferred, the systems and methods disclosed herein may also be applicable to more invasive monitoring. Thus, if it is desired to monitor and record intracranial EEG signals (e.g., ECoG), then it may be possible to implant one or more of the implantable devices inside the subject's skull 191 (e.g., in the brain, above or below the dura mater, or a combination thereof) through a burr hole created in the subject's skull.

Figure 20:
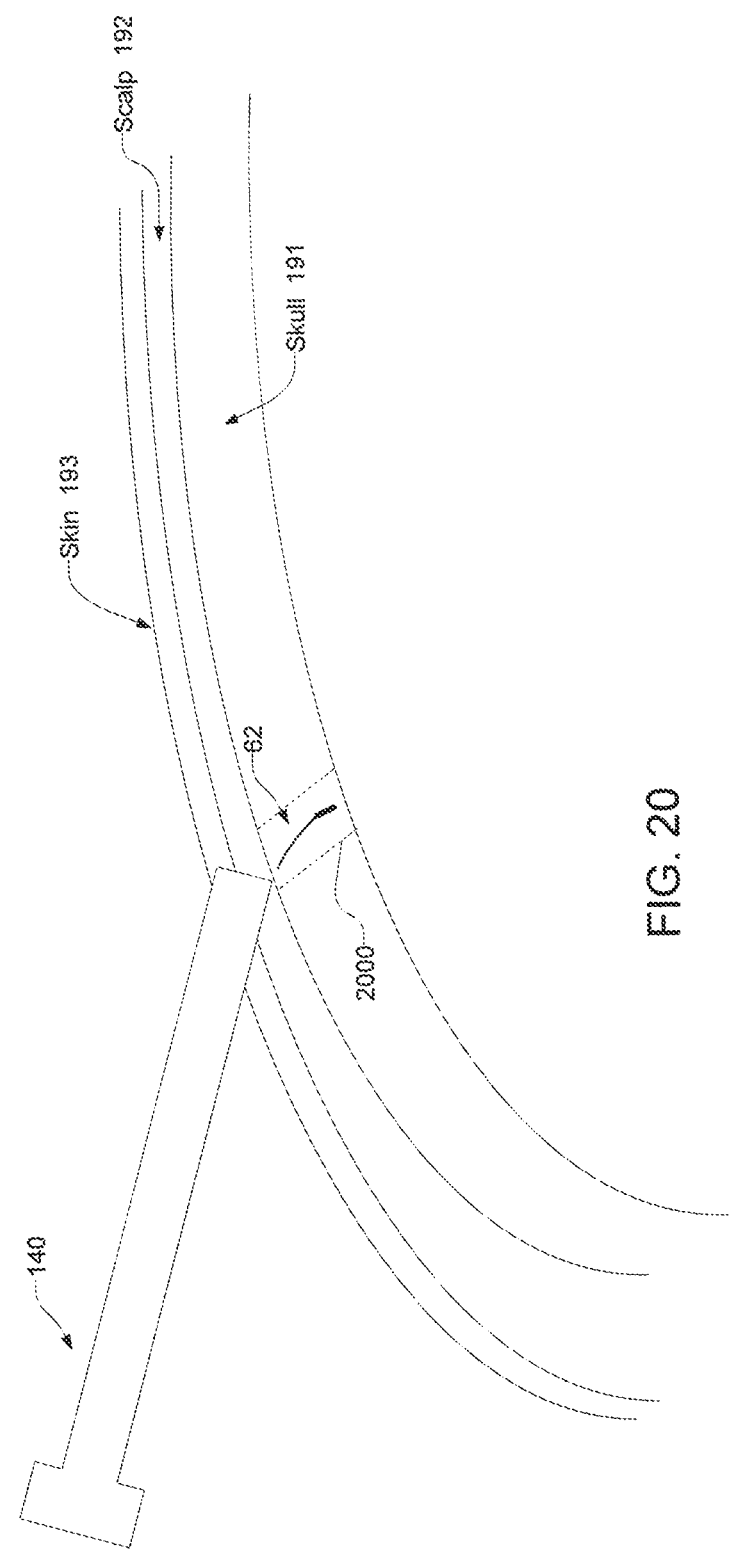
FIG. 20 illustrates a simplified trocar or needle-like device that may be used to implant the implantable device within a burr hole in the subject's skull.

In a more invasive system shown in FIG. 20, the implantable devices 62 may be placed in a burr hole 2000 or groove that extends partially through the skull 191 or completely through the skull 191 to monitor the subject's brain activity. In such embodiments, the implantable devices 62 may use the anchoring assembly (not shown) to mount itself to the subject's skull 191 within the burr hole 2000. While not shown in FIG. 20, it may also be desirable to place the implantable devices 62 underneath the skull 191 in an epidural or subdural space.

Figure 21:
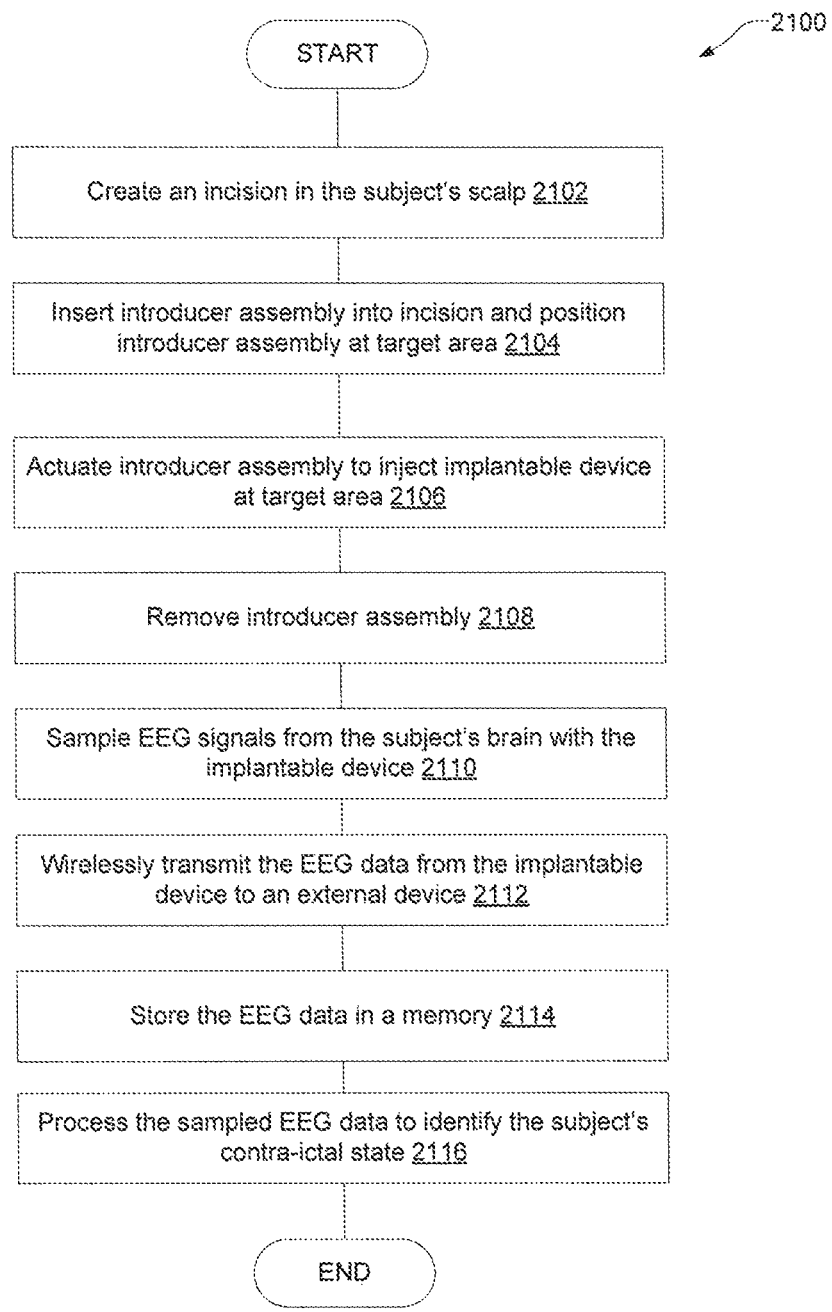
FIG. 21 illustrates a method of inserting an implantable device in the subject and wirelessly sampling EEG signals from a subject.

FIG. 21 schematically illustrates one example of a minimally invasive method 2100 of implanting the implantable devices for ambulatory monitoring of a subject's EEG signals. At step 2102, an incision is made in the subject's scalp. At step 2104, an introducer assembly is inserted into the incision and a distal tip of the introducer assembly is positioned at or near the target site. Of course, the introducer assembly itself may be used to create the incision. For example, if the introducer assembly is in the form of a syringe, the syringe tip may be made to create the incision and steps 2102 and 2104 may be consolidated into a single step. At step 2106, the introducer assembly is actuated to inject the implantable device 62 to the target site. If desired, the introducer may be repositioned to additional target sites underneath the subject's skin and above the skull. If needed, additional incisions may be created in the subject's skin to allow for injection of the implantable device 62 at the additional target sites. After a desired number of implantable devices are placed in the subject, at step 2108 the introducer assembly is removed from the target site. At step 2110, the implantable devices are activated and used to perform long term monitoring of the subject's EEG signals from each of the target sites. At step 2112, the sampled EEG signals are then wirelessly transmitted to an external device. At step 2114, the sampled EEG signals may then be stored in a memory in the external device or in another device (e.g., personal computer). If desired, the EEG signals may then be processed in the external device or in a personal computer of the physician. In one exemplary embodiment, the EEG data collected from the subject may be used to identify the subject's contra-ictal state, step 2116 (FIG. 1).

While not shown in FIG. 20, it may also be desirable to anchor the implantable devices to the subject to reduce the likelihood that the implantable devices are dislodged from their desired position. Anchoring may be performed with tissue adhesive, barbs or other protrusions, sutures, or the like.

Advantageously, the implantable devices in accordance with some embodiments are able to monitor EEG signals from the subject without the use of burr holes in the skull or implantation within the brain—which significantly reduces the risk of infection for the subject and makes the implantation process easier. While there is some attenuation of the EEG signals and movement artifacts in the signals, because the implantable devices are below the skin, it is believed that there will be much lower impedance than scalp electrodes. Furthermore, having a compact implantable device 62 below the skin reduces common-mode interference signals which can cause a differential signal to appear due to any imbalance in electrode impedance and the skin provides some protection from interference caused by stray electric charges (static).

Figure 22:
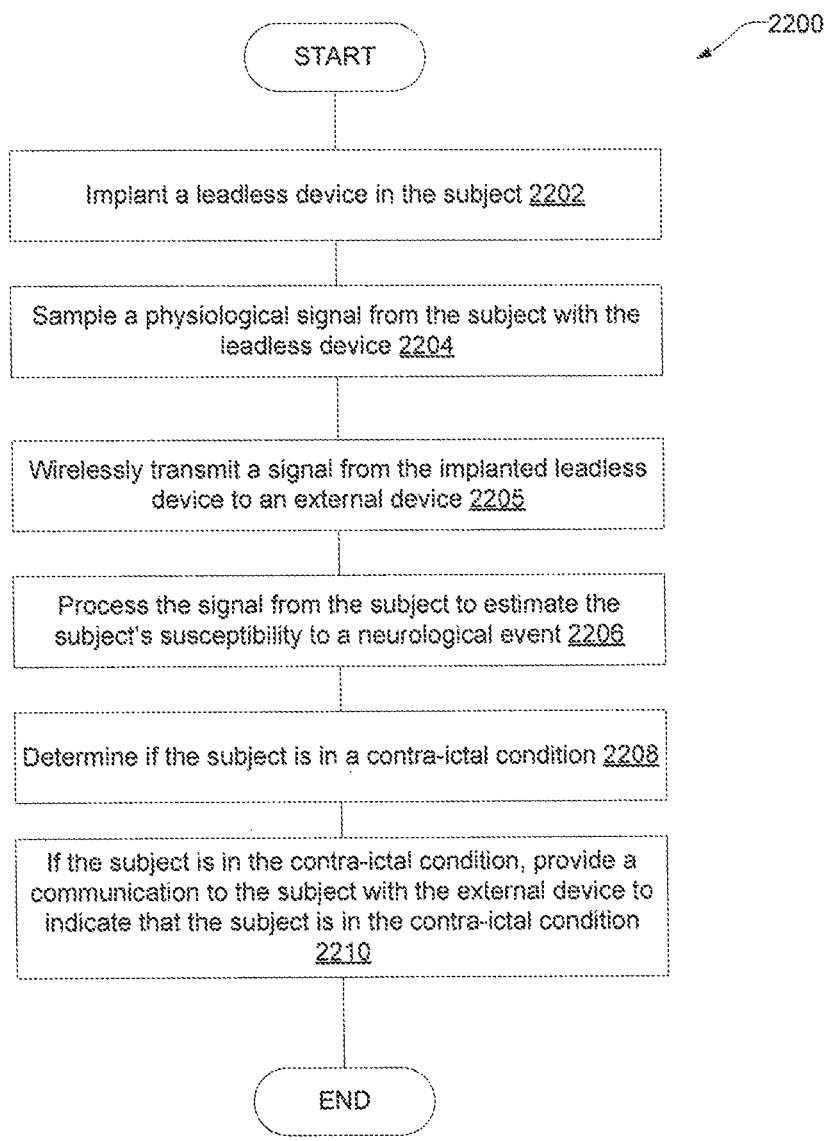
FIG. 22 illustrates a method of using an implantable device in the subject to determine if the subject is in a contra-ictal condition.

As shown in FIG. 22, once implanted in the subject (step 2202), the monitoring systems 60 may be used to monitor the subject's susceptibility to a seizure (or other neurological event). To monitor the subject's susceptibility to a seizure, the implanted leadless devices are activated to sample physiological signals (e.g., EEG) from the subject using the methods described above, step 2204. A signal is transmitted from the implanted leadless devices to the external device, step 2205. The signal may comprise the EEG data or other similar data. Such a signal may include the EEG signal, features extracted from the EEG signal, a classification output, or the like.

The EEG signal from the subject may be processed (either in the implanted devices and/or in the external device) to estimate the subject's susceptibility to a seizure, step 2206. As described above in FIGS. 2 to 8, the EEG signals may be processed to determine if the subject is in a pro-ictal condition, inter-ictal condition, contra-ictal condition, or the like.

While FIG. 22 illustrates using the external device to provide an output to the subject, in some embodiments, the seizure advisory system may be completely implanted, and a transponder or other implanted device may be used to provide an audio or tactile feedback to the subject that indicates that they are in the contra-ictal condition. In preferred embodiments, the processing determines if the subject is in the contra-ictal condition, step 2208. If the subject is in the contra-ictal condition, a communication is provided to the subject with the external device to indicate that the subject is in the contra-ictal condition, step 2210. The communication may be in the form of LEDS (e.g., green LED) or other visual output, an audio output, a tactile output, or some combination thereof.

While not shown in FIG. 22, the methods of the present invention may also be configured to provide a substantially continuous output of the subject's susceptibility to a seizure, and if the subject is at an increased susceptibility to a seizure or normal susceptibility, the methods of the present invention will provide such a communication to the subject and/or initiate therapy.

Figure 23:
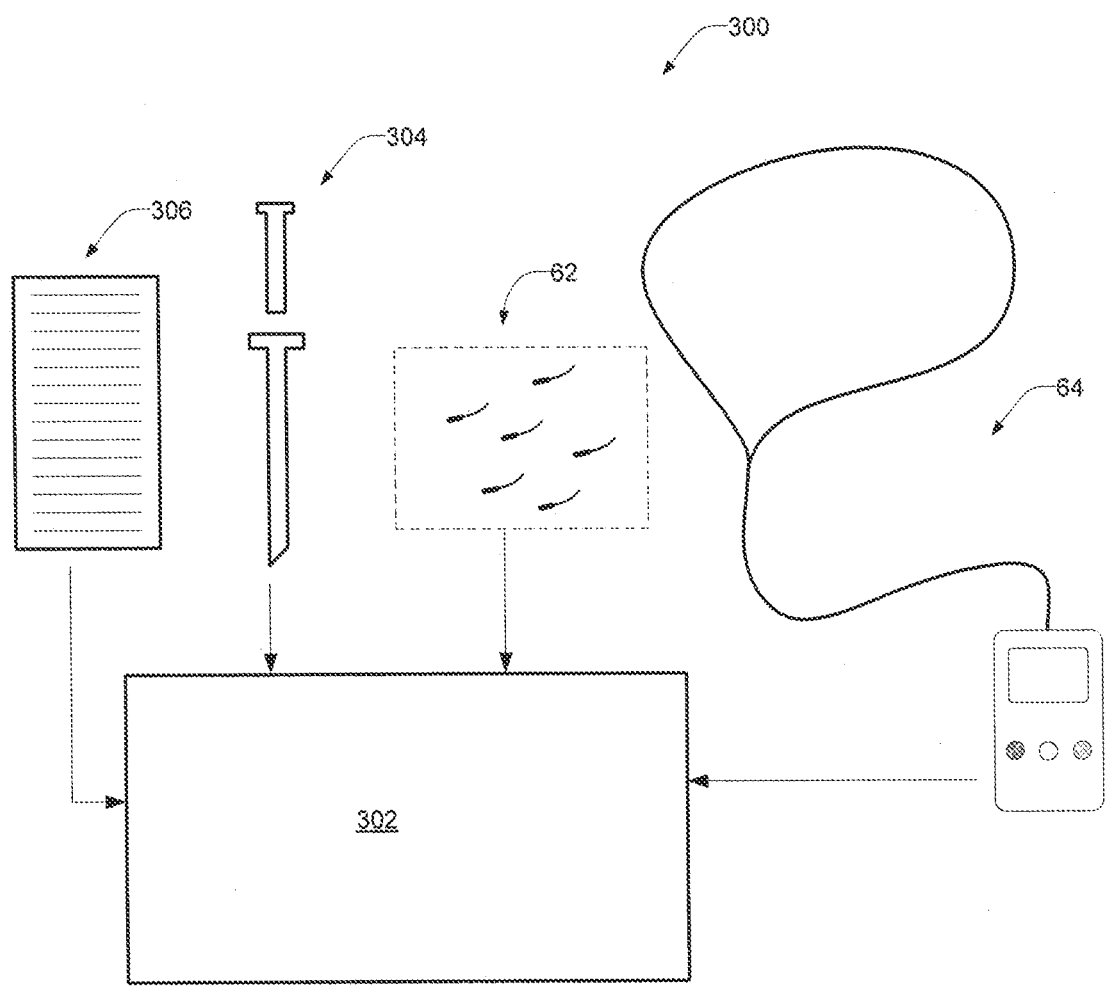
FIG. 23 is a kit in accordance with embodiments of the present invention.

FIG. 23 illustrates a packaged system or kit 300 that is encompassed by the present invention. The packaged system 300 may include a package 302 that has one or more compartments for receiving an introducer assembly 304, one or more implantable devices 62, and an external device 64. The introducer assembly 304 may be provided in the form of a syringe-like device or a cannula and stylet, as described above with respect to FIGS. 15A-15B. The implantable device 62 may include any of the embodiments described herein. One or more of the implantable devices 62 may be pre-loaded within the introducer assembly 304. In other embodiments, the implantable devices 62 may be loaded in its separate sterile packaging (shown in dotted lines) for easy loading into the introducer assembly 304. The packaged system 300 may include instructions for use ("IFU") 306 that describe any of the methods described herein.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. For example, the present invention also encompasses other more invasive embodiments which may be used to monitor the subject's neurological system.

Alternative embodiments of the implantable device of the present invention may require a neurosurgeon to create a more invasive incision in the subject's scalp. For example, it may be desirable to use a low profile device that is not substantially cylindrical, but instead is substantially planar or concave so as to conform to the curvature of the subject's skull. Such embodiments would likely not be able to be implanted without general anesthesia and may require a surgeon to implant the device.

On the other hand, in some embodiments it may be desirable to be completely non-invasive. Such embodiments include "implantable" devices 62 that are not actually implanted, but instead are "wearable" and may be attached to the outer surface of the skin with adhesive or a bandage so as to maintain contact with the subject's skin. For example, it may be possible to surface mount the device 62 behind the ears, in the scalp, on the forehead, along the jaw, or the like. Because the electrodes are wireless and are such a small size, unlike conventional electrodes, the visual appearance of the electrodes will be minimal.

Furthermore, in some embodiments, it may be desirable to modify the implantable device 62 to provide stimulation to the subject. In such embodiments, the implantable device 62 will include a pulse generator and associated hardware and software for delivering stimulation to the subject through the first and second electrodes 1624, 1626 (or other electrodes coupled to the device). In such embodiments, the external device 64 may include the hardware and software to generate the control signals for delivering the electrical stimulation to the subject.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. For example, while embodiments described above indicate that power to the implanted devices may be derived wirelessly from an external device and/or from a battery in the implanted device, it should be appreciated that the internal devices may derive or otherwise "scavenge" power from other types of conventional or proprietary assemblies. Such scavenging methods may be used in conjunction with the external power source and/or the internal power source, or it may be used by itself to provide the necessary power for the implanted devices. For example, the implanted devices may include circuitry and other assemblies (e.g., a microgenerator) that derive and store power from subject-based energy sources such as kinetic movement/vibrations (e.g., gross body movements), movement of organs or other bodily fluids (e.g., heart, lungs, blood flow), and thermal sources in the body (e.g., temperature differences and variations across tissue). As can be imagined, such technology could reduce or eliminate the need for recharging of an implanted battery, replacement of a depleted battery, and/or the creation of an external RF field—and would improve the ease of use of the devices by the subjects.

Some embodiments of the monitoring system may include an integral patient diary functionality. The patient diary may be a module in the external device and inputs by the subject may be used to provide secondary inputs to provide background information for the sampled EEG signals. For example, if a seizure is recorded, the seizure diary may provide insight regarding a trigger to the seizure, or the like. The diary may automatically record the time and date of the entry by the subject. Entries by the subject may be a voice recording, or through activation of user inputs on the external device. The diary may be used to indicate the occurrence of an aura, occurrence of a seizure, the consumption of a meal, missed meal, delayed meal, activities being performed, consumption of alcohol, the subject's sleep state (drowsy, going to sleep, waking up, etc.), mental state (e.g., depressed, excited, stressed), intake of their AEDs, medication changes, missed dosage of medication, menstrual cycle, illness, or the like. Thereafter, the subject inputs recorded in the diary may also be used by the physician in assessing the subject's epilepsy state and/or determine the efficacy of the current treatment. Furthermore, the physician may be able to compare the number of seizures logged by the subject to the number of seizures detected by the seizure detection algorithm.

It is intended that the following claims define the scope of the invention and that methods and structures within the scope of these claims and their equivalents be covered thereby.

What is claimed is:

1. A physiological monitoring system comprising:
    an electrode configured to detect a physiological signal from a subject;
    a processing assembly for sampling the physiological signal, the processing assembly being configured to process the physiological signal to determine whether the subject is in a contra-ictal state and generate an output indicating the determination, said contra-ictal state being a neurological state in which the subject is unlikely to transition into an ictal state within a time period; and
    a therapy device that receives the output and selectively applies therapy in response to the output.

2. The physiological monitoring system of claim 1, further comprising:
    a user interface configured to provide an output to the subject regarding the contra-ictal state of the subject.

3. The physiological monitoring system of claim 1, the processing assembly being further configured to process the physiological signal to determine whether the subject transitions into or from the contra-ictal state.

4. The physiological monitoring system of claim 1, the processing assembly being further configured to process the physiological signal to determine whether the subject transitions from the contra-ictal state to an inter-ictal state different than the contra-ictal state.

5. The physiological monitoring system of claim 1, the processing assembly being further configured to process the physiological signal to determine whether the subject transitions from the contra-ictal state to the ictal state.

6. The physiological monitoring system of claim 1, wherein the processing assembly is adapted to determine if the subject is in a contra-ictal condition by:
    extracting N features from the sampled physiological signal;
    generating an N-dimensional feature vector of the extracted N features for time points of the sampled physiological signal; and
    determining if the N-dimensional feature vector is within a contra-ictal cluster or region in an N-dimensional space.

7. The physiological monitoring system of claim 1, wherein the physiological signal is at least one of an EEG signal, a heart rate signal, and a respiratory signal.

8. The physiological monitoring system of claim 1, wherein the physiological signal corresponds to at least one of a blood pressure, a blood oxygenation, a temperature, a blood flow, an ECG, an EKG, a chemical concentration of a neurotransmitter, a chemical concentration of a medication, and a pH in the blood.

9. The physiological monitoring system of claim 1, wherein the electrode is configured to detect the physiological signal through the skin of the subject.

10. The physiological monitoring system of claim 1, wherein the therapy device comprises an implanted stimulator.

11. A method of monitoring physiological signals from a subject, said method comprising:
    detecting a physiological signal from the subject with an electrode;
    analyzing the physiological signal from the subject using a processor to determine whether the subject is in a contra-ictal state and generate an output indicating the determination, said contra-ictal state being a neurological state in which the subject is unlikely to transition into an ictal state within a time period; and
    selectively applying therapy in response to the output using a therapy device.

12. The method of claim 11, further comprising:
    reporting an output to the subject regarding the contra-ictal state of the subject.

13. The method of claim 11, further comprising:
    analyzing the physiological signal to determine whether the subject transitions into or from the contra-ictal state.

14. The method of claim 11, further comprising:
    analyzing the physiological signal to determine whether the subject transitions from the contra-ictal state to an inter-ictal state different than the contra-ictal state.

15. The method of claim 11, further comprising:
    analyzing the physiological signal to determine whether the subject transitions from the contra-ictal state to the ictal state.

16. The method of claim 11, wherein the analyzing the physiological signal comprises:
    extracting N features from the sampled physiological signal;
    generating an N-dimensional feature vector of the extracted N features for time points of the sampled physiological signal; and
    determining if the N-dimensional feature vector is within a contra-ictal cluster or region in an N-dimensional space.

17. The method of claim 11, wherein the physiological signal is at least one of an EEG signal, a heart rate signal, and a respiratory signal.

18. The method of claim 11, wherein the physiological signal corresponds to at least one of a blood pressure, a blood oxygenation, a temperature, a blood flow, an ECG, an EKG, a chemical concentration of a neurotransmitter, a chemical concentration of a medication, and a pH in the blood.

19. The method of claim 11, wherein the electrode is configured to detect the physiological signal through the skin of the subject.

20. The method of claim 11, wherein selectively applying therapy in response to the output using a therapy device comprises applying the therapy using an implanted stimulator.

21. A physiological monitoring system comprising:
    an electrode configured to detect a physiological signal from a subject;
    a processing assembly for sampling the physiological signal, the processing assembly being configured to process the physiological signal to determine whether the subject is in a contra-ictal state and generate an output indicating the determination, said contra-ictal state being a neurological state in which the subject is unlikely to transition into an ictal state within a time period;
    a therapy device that receives the output and selectively applies therapy in response to the output; and
    a user interface in communication with the processing assembly, the user interface generating an output based on the physiological signal, the output indicating whether the subject is in a contra-ictal state.

22. The physiological monitoring system of claim 21, the output further indicating at least one of whether the subject transitions into the contra-ictal state, the subject transitions from the contra-ictal state, the subject transitions from the contra-ictal state to an inter-ictal state different than the contra-ictal state, and the subject transitions from the contra-ictal state to the ictal state.

23. The physiological monitoring system of claim 21, wherein the therapy device comprises an implanted stimulator.

* * * * *